(12) United States Patent
Crawford et al.

(10) Patent No.: US 9,919,309 B2
(45) Date of Patent: *Mar. 20, 2018

(54) DENSITY PHASE SEPARATION DEVICE

(71) Applicant: Becton, Dickinson and Company, Franklin Lakes, NJ (US)

(72) Inventors: Jamieson W. Crawford, Hagerten (SE); Ravi Attri, Budd Lake, NJ (US); Christopher A. Battles, Seymour, CT (US); Benjamin R. Bartfeld, Ringwood, NJ (US); Gregory R. Hires, Fairfield, CT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 274 days.

This patent is subject to a terminal disclaimer.

(21) Appl. No.: 14/629,657

(22) Filed: Feb. 24, 2015

(65) Prior Publication Data
US 2015/0168280 A1    Jun. 18, 2015

Related U.S. Application Data

(62) Division of application No. 12/780,432, filed on May 14, 2010, now Pat. No. 8,998,000.
(Continued)

(51) Int. Cl.
*G01N 1/40* (2006.01)
*B01L 3/00* (2006.01)
(Continued)

(52) U.S. Cl.
CPC ...... *B01L 3/50215* (2013.01); *B01D 17/0217* (2013.01); *B01D 21/2405* (2013.01);
(Continued)

(58) Field of Classification Search
CPC ............ B01D 17/0217; B01D 21/2405; B01D 21/262; B01L 3/50215; G01N 1/34;
(Continued)

(56) References Cited

U.S. PATENT DOCUMENTS 2,577,780 A    12/1951  Lockhart
2,693,049 A    11/1954  Atton
(Continued)

FOREIGN PATENT DOCUMENTS

AT         414209 B     10/2006
DE         2749130 A1    5/1979
(Continued)

*Primary Examiner* — Terry K Cecil
(74) *Attorney, Agent, or Firm* — The Webb Law Firm

(57) ABSTRACT

A mechanical separator for separating a fluid sample into first and second phases within a collection container is disclosed. The mechanical separator may have a separator body having a through-hole defined therein, with the through-hole adapted for allowing fluid to pass therethrough. The separator body includes a float, having a first density, and a ballast, having a second density greater than the first density. A portion of the float is connected to a portion of the ballast. Optionally, the float may include a first extended tab adjacent a first opening of the through-hole and a second extended tab adjacent the second opening of the through-hole. In certain configurations, the separator body also includes an extended tab band disposed about an outer surface of the float. The separator body may also include an engagement band circumferentially disposed about at least a portion of the separator body.

33 Claims, 43 Drawing Sheets

Related U.S. Application Data

(60) Provisional application No. 61/178,599, filed on May 15, 2009.

(51) Int. Cl.
  *B01D 21/24* (2006.01)
  *B01D 17/02* (2006.01)
  *G01N 1/34* (2006.01)
  *B01D 21/26* (2006.01)
  *G01N 33/49* (2006.01)

(52) U.S. Cl.
  CPC .......... *G01N 1/34* (2013.01); *G01N 1/4077* (2013.01); *B01D 21/262* (2013.01); *G01N 33/491* (2013.01); *G01N 2001/4083* (2013.01); *Y10T 436/25375* (2015.01)

(58) Field of Classification Search
  CPC ......... G01N 1/4077; G01N 2001/4083; G01N 33/491; Y10T 436/25375
  See application file for complete search history.

(56) References Cited

U.S. PATENT DOCUMENTS

| | | |
|---|---|---|
| 2,910,798 A | 11/1959 | Bias |
| 3,300,051 A | 1/1967 | Mitchell |
| 3,326,215 A | 6/1967 | Sarnoff et al. |
| 3,508,653 A | 4/1970 | Coleman |
| 3,543,338 A | 12/1970 | Cooper |
| 3,647,070 A | 3/1972 | Adler |
| 3,654,925 A | 4/1972 | Holderith |
| 3,661,265 A | 5/1972 | Greenspan |
| 3,741,400 A | 6/1973 | Dick |
| 3,747,257 A | 7/1973 | Olsen |
| 3,771,965 A | 11/1973 | Grams |
| 3,773,450 A | 11/1973 | Svanfos |
| 3,779,383 A | 12/1973 | Ayres |
| 3,780,935 A | 12/1973 | Lukacs et al. |
| 3,786,985 A | 1/1974 | Blaivas |
| 3,800,947 A | 4/1974 | Smith |
| 3,809,733 A | 5/1974 | Sandiford et al. |
| 3,814,248 A | 6/1974 | Lawhead |
| 3,814,258 A | 6/1974 | Ayres |
| 3,832,110 A | 8/1974 | Hehl |
| 3,849,072 A | 11/1974 | Ayres |
| 3,850,174 A | 11/1974 | Ayres |
| 3,852,194 A | 12/1974 | Zine, Jr. |
| 3,862,042 A | 1/1975 | Ayres |
| 3,879,295 A | 4/1975 | Glover et al. |
| 3,882,021 A | 5/1975 | Ayres |
| 3,886,928 A | 6/1975 | Sarstedt |
| 3,887,464 A | 6/1975 | Ayres |
| 3,887,465 A | 6/1975 | Ayres |
| 3,887,466 A | 6/1975 | Ayres |
| 3,890,237 A | 6/1975 | Welch |
| 3,890,954 A | 6/1975 | Greenspan |
| 3,891,553 A | 6/1975 | Ayres |
| 3,894,950 A | 7/1975 | Ayres et al. |
| 3,894,951 A | 7/1975 | Ayres |
| 3,894,952 A | 7/1975 | Ayres |
| 3,897,337 A | 7/1975 | Ayres |
| 3,897,340 A | 7/1975 | Ayres |
| 3,897,343 A | 7/1975 | Ayres |
| 3,901,219 A | 8/1975 | Kay |
| 3,909,419 A | 9/1975 | Ayres |
| 3,919,085 A | 11/1975 | Ayres |
| 3,920,549 A | 11/1975 | Gigliello et al. |
| 3,920,557 A | 11/1975 | Ayres |
| 3,929,646 A | 12/1975 | Adler |
| 3,931,018 A | 1/1976 | North, Jr. |
| 3,932,277 A | 1/1976 | McDermott et al. |
| 3,935,113 A | 1/1976 | Ayres |
| 3,941,699 A | 3/1976 | Ayres |
| 3,945,928 A | 3/1976 | Ayres |
| 3,947,176 A | 3/1976 | Rainville |
| 3,951,801 A | 4/1976 | Ayres |
| 3,957,654 A | 5/1976 | Ayres |
| 3,960,727 A | 6/1976 | Hochstrasser |
| 3,969,250 A | 7/1976 | Farr |
| 3,970,565 A | 7/1976 | Ahlstrand et al. |
| 3,972,812 A | 8/1976 | Gresl, Jr. |
| 3,981,804 A | 9/1976 | Gigliello |
| 4,001,122 A | 1/1977 | Griffin |
| 4,004,868 A | 1/1977 | Ohdate |
| 4,021,340 A | 5/1977 | Zine, Jr. |
| 4,021,352 A | 5/1977 | Sarstedt |
| 4,027,660 A | 6/1977 | Wardlaw et al. |
| 4,055,501 A | 10/1977 | Cornell |
| 4,057,499 A | 11/1977 | Buono |
| 4,077,396 A | 3/1978 | Wardlaw et al. |
| 4,082,085 A | 4/1978 | Wardlaw et al. |
| 4,083,788 A | 4/1978 | Ferrara |
| 4,088,582 A | 5/1978 | Murty et al. |
| 4,119,125 A | 10/1978 | Elkins |
| 4,131,549 A | 12/1978 | Ferrara |
| 4,134,832 A | 1/1979 | Heimreid |
| 4,142,668 A | 3/1979 | Lee |
| 4,152,270 A | 5/1979 | Cornell |
| 4,154,690 A | 5/1979 | Ballies |
| 4,159,896 A | 7/1979 | Levine et al. |
| 4,169,060 A | 9/1979 | Columbus |
| 4,189,385 A | 2/1980 | Greenspan |
| 4,201,209 A | 5/1980 | LeVeen et al. |
| 4,202,769 A | 5/1980 | Greenspan |
| 4,243,362 A | 1/1981 | Rees et al. |
| 4,246,123 A | 1/1981 | Cornell et al. |
| 4,257,886 A | 3/1981 | Kessler |
| 4,275,030 A | 6/1981 | Mares |
| 4,279,863 A | 7/1981 | Friehler |
| 4,294,707 A | 10/1981 | Ikeda et al. |
| 4,315,892 A | 2/1982 | Stone et al. |
| 4,364,832 A | 12/1982 | Ballies |
| 4,369,117 A | 1/1983 | White |
| 4,379,849 A | 4/1983 | Heimreid |
| 4,381,275 A | 4/1983 | Sorensen |
| 4,396,381 A | 8/1983 | Fanger et al. |
| 4,409,988 A | 10/1983 | Greenspan |
| 4,417,981 A | 11/1983 | Nugent |
| 4,425,235 A | 1/1984 | Cornell et al. |
| 4,426,290 A | 1/1984 | Ichikawa et al. |
| 4,443,345 A | 4/1984 | Wells |
| 4,444,711 A | 4/1984 | Schad |
| 4,448,741 A | 5/1984 | Schad |
| 4,464,254 A | 8/1984 | Dojki et al. |
| 4,470,936 A | 9/1984 | Potter |
| 4,492,634 A | 1/1985 | Villa-Real |
| 4,508,676 A | 4/1985 | Sorensen |
| 4,517,090 A | 5/1985 | Kersten et al. |
| 4,522,713 A | 6/1985 | Nussbaumer et al. |
| 4,533,474 A | 8/1985 | Arnaudeau |
| 4,535,014 A | 8/1985 | Wright |
| 4,567,754 A | 2/1986 | Wardlaw et al. |
| 4,569,764 A | 2/1986 | Satchell |
| 4,602,995 A | 7/1986 | Cassaday et al. |
| 4,701,292 A | 10/1987 | Valyi |
| 4,707,276 A | 11/1987 | Dodge et al. |
| 4,717,324 A | 1/1988 | Schad et al. |
| 4,726,758 A | 2/1988 | Sekine et al. |
| 4,770,779 A | 9/1988 | Ichikawa et al. |
| 4,803,031 A | 2/1989 | Ochs et al. |
| 4,818,386 A | 4/1989 | Burns |
| 4,828,716 A | 5/1989 | McEwen et al. |
| 4,832,851 A | 5/1989 | Bowers et al. |
| 4,843,869 A | 7/1989 | Levine et al. |
| 4,853,137 A | 8/1989 | Ersson |
| 4,877,520 A | 10/1989 | Burns |
| 4,917,801 A | 4/1990 | Luderer et al. |
| 4,935,184 A | 6/1990 | Sorensen |
| 4,957,637 A | 9/1990 | Cornell |
| 4,957,682 A | 9/1990 | Kobayashi et al. |
| 5,007,892 A | 4/1991 | Columbus |
| 5,019,243 A | 5/1991 | McEwen et al. |
| 5,028,226 A | 7/1991 | De'ath et al. |

(56) References Cited

U.S. PATENT DOCUMENTS

| | | |
|---|---|---|
| 5,030,341 A | 7/1991 | McEwen et al. |
| 5,086,784 A | 2/1992 | Levine et al. |
| 5,112,490 A | 5/1992 | Turpen |
| 5,171,533 A | 12/1992 | Fine et al. |
| 5,236,604 A | 8/1993 | Fiehler |
| 5,251,474 A | 10/1993 | Wardlaw et al. |
| 5,269,927 A | 12/1993 | Fiehler |
| 5,271,852 A | 12/1993 | Luoma, II |
| 5,282,981 A | 2/1994 | Adams et al. |
| 5,308,506 A | 5/1994 | McEwen et al. |
| 5,325,977 A | 7/1994 | Haynes et al. |
| 5,354,483 A | 10/1994 | Furse |
| 5,389,265 A | 2/1995 | Luoma, II |
| 5,393,494 A | 2/1995 | Greenfield et al. |
| 5,419,835 A | 5/1995 | Adams et al. |
| 5,422,018 A | 6/1995 | Saunders et al. |
| 5,454,958 A | 10/1995 | Fiehler |
| 5,455,009 A | 10/1995 | Vogler et al. |
| 5,456,885 A | 10/1995 | Coleman et al. |
| 5,462,716 A | 10/1995 | Holm |
| 5,474,687 A | 12/1995 | Van Vlasselaer |
| 5,511,558 A | 4/1996 | Shepard et al. |
| 5,533,518 A | 7/1996 | Vogler |
| 5,552,325 A | 9/1996 | Nochumson et al. |
| 5,556,541 A | 9/1996 | Ruschke |
| 5,560,830 A | 10/1996 | Coleman et al. |
| 5,575,778 A | 11/1996 | Hardt et al. |
| 5,577,513 A | 11/1996 | Van Vlasselaer |
| 5,632,895 A | 5/1997 | Tsukagoshi et al. |
| 5,632,905 A | 5/1997 | Haynes |
| 5,646,004 A | 7/1997 | Van Vlasselaer |
| 5,648,223 A | 7/1997 | Van Vlasselaer |
| 5,651,998 A | 7/1997 | Bertschi et al. |
| 5,707,876 A | 1/1998 | Levine |
| 5,736,033 A | 4/1998 | Coleman et al. |
| 5,755,360 A | 5/1998 | Elliott |
| 5,785,925 A | 7/1998 | U'Ren |
| 5,789,033 A | 8/1998 | Bertschi et al. |
| 5,798,069 A | 8/1998 | Bertschi et al. |
| 5,840,502 A | 11/1998 | Van Vlasselaer |
| 5,853,600 A | 12/1998 | McNeal et al. |
| 5,860,937 A | 1/1999 | Cohen |
| 5,902,276 A | 5/1999 | Namey, Jr. |
| 5,955,009 A | 9/1999 | Kazuma |
| 6,001,087 A | 12/1999 | Zurcher |
| 6,074,613 A | 6/2000 | Harness et al. |
| 6,074,883 A | 6/2000 | Kelly et al. |
| 6,106,261 A | 8/2000 | von Holdt |
| 6,161,712 A | 12/2000 | Savitz et al. |
| 6,174,447 B1 | 1/2001 | Spindler |
| 6,225,123 B1 | 5/2001 | Cohen et al. |
| 6,277,331 B1 | 8/2001 | Konrad |
| 6,280,400 B1 | 8/2001 | Niermann |
| 6,296,796 B1 | 10/2001 | Gordon |
| 6,302,919 B1 | 10/2001 | Chambers et al. |
| 6,379,139 B1 | 4/2002 | Boucherie |
| 6,390,966 B2 | 5/2002 | Anderson |
| 6,406,671 B1 | 6/2002 | DiCesare et al. |
| 6,409,528 B1 | 6/2002 | Bodnar |
| 6,464,921 B1 | 10/2002 | Armbruster |
| 6,465,256 B1 | 10/2002 | Iskra |
| 6,471,069 B2 | 10/2002 | Lin et al. |
| 6,479,298 B1 | 11/2002 | Miller et al. |
| 6,497,325 B1 | 12/2002 | DiCesare et al. |
| 6,516,953 B1 | 2/2003 | DiCesare et al. |
| 6,537,503 B1 | 3/2003 | Conway |
| 6,558,149 B1 | 5/2003 | Bodmer et al. |
| 6,582,904 B2 | 6/2003 | Dahm |
| 6,593,145 B2 | 7/2003 | Macfarlane et al. |
| 6,607,685 B2 | 8/2003 | Naritomi et al. |
| 6,623,688 B2 | 9/2003 | Gedritis et al. |
| 6,740,240 B2 | 5/2004 | Coville et al. |
| 6,758,804 B2 | 7/2004 | Anderson |
| 6,783,346 B2 | 8/2004 | Bodmer et al. |
| 6,793,892 B1 | 9/2004 | Niermann |
| 6,803,022 B2 | 10/2004 | DiCesare et al. |
| 6,817,256 B2 | 11/2004 | Mehra et al. |
| 6,866,811 B2 | 3/2005 | Kayano et al. |
| 6,933,148 B2 | 8/2005 | Collins et al. |
| 6,976,509 B1 | 12/2005 | Kirvan |
| 6,979,307 B2 | 12/2005 | Beretta et al. |
| 7,074,577 B2 | 7/2006 | Haubert et al. |
| 7,077,273 B2 | 7/2006 | Ellsworth et al. |
| 7,153,477 B2 | 12/2006 | DiCesare et al. |
| 7,158,854 B1 | 1/2007 | Kolander |
| 7,166,218 B2 | 1/2007 | Trapy et al. |
| 7,179,391 B2 | 2/2007 | Leach et al. |
| 7,188,734 B2 | 3/2007 | Konrad |
| 7,205,157 B2 | 4/2007 | Jurgensen et al. |
| 7,211,433 B1 | 5/2007 | Dahm et al. |
| 7,220,593 B2 | 5/2007 | Haubert et al. |
| 7,223,346 B2 | 5/2007 | Dorian et al. |
| 7,282,168 B2 | 10/2007 | Downer et al. |
| 7,294,311 B2 | 11/2007 | Coville |
| 7,309,468 B2 | 12/2007 | Stevens et al. |
| 7,329,534 B2 | 2/2008 | Haubert et al. |
| 7,358,095 B2 | 4/2008 | Haubert et al. |
| 7,374,678 B2 | 5/2008 | Leach et al. |
| 7,445,125 B2 | 11/2008 | Ellsworth et al. |
| 7,470,371 B2 | 12/2008 | Dorian et al. |
| 7,547,272 B2 | 6/2009 | Ellsworth et al. |
| 7,578,975 B2 | 8/2009 | DiCesare et al. |
| 7,629,176 B2 | 12/2009 | Haubert et al. |
| 7,645,425 B2 | 1/2010 | Haywood et al. |
| 7,736,593 B2 | 6/2010 | Dastane et al. |
| 7,745,106 B2 | 6/2010 | Beretta et al. |
| 7,767,087 B2 | 8/2010 | Wilson |
| 7,771,590 B2 | 8/2010 | Leach et al. |
| 7,780,860 B2 | 8/2010 | Higgins et al. |
| 7,806,276 B2 | 10/2010 | Leach et al. |
| 7,832,566 B2 | 11/2010 | Leach et al. |
| 7,837,884 B2 | 11/2010 | Dorian et al. |
| 7,845,499 B2 | 12/2010 | Higgins et al. |
| 7,901,584 B2 | 3/2011 | Dorian et al. |
| 7,914,689 B2 | 3/2011 | Higgins et al. |
| 7,915,029 B2 | 3/2011 | Haubert et al. |
| 7,919,049 B2 | 4/2011 | Haubert et al. |
| 7,922,972 B2 | 4/2011 | Ellsworth et al. |
| 7,927,563 B1 | 4/2011 | Lavi |
| 7,947,186 B2 | 5/2011 | Soares et al. |
| 7,947,236 B2 | 5/2011 | Losada et al. |
| 7,954,646 B2 | 6/2011 | Leach et al. |
| 7,955,501 B2 | 6/2011 | Wilson |
| 7,972,578 B2 | 7/2011 | DiCesare et al. |
| 7,992,725 B2 | 8/2011 | Leach et al. |
| 8,012,077 B2 | 9/2011 | Hoeppner |
| 8,012,742 B2 | 9/2011 | Haubert et al. |
| 8,048,297 B2 | 11/2011 | Leach et al. |
| 8,048,320 B2 | 11/2011 | Leach et al. |
| 8,048,321 B2 | 11/2011 | Leach et al. |
| 8,062,534 B2 | 11/2011 | Higgins et al. |
| 8,092,692 B2 | 1/2012 | Nilsen et al. |
| 8,114,680 B2 | 2/2012 | Haubert et al. |
| 8,119,013 B2 | 2/2012 | Leach et al. |
| 8,133,389 B2 | 3/2012 | Dorian et al. |
| 8,206,648 B2 | 6/2012 | Sattler |
| RE43,547 E | 7/2012 | Ellsworth et al. |
| 8,236,258 B2 | 8/2012 | Leach et al. |
| 8,241,592 B2 | 8/2012 | Duffy, Jr. et al. |
| 8,282,839 B2 | 10/2012 | Ellsworth |
| 8,313,954 B2 | 11/2012 | Leach et al. |
| 8,348,066 B2 | 1/2013 | Ellsworth |
| 8,394,342 B2 | 3/2013 | Felix et al. |
| 8,474,630 B2 | 7/2013 | Dorian et al. |
| 8,518,272 B2 | 8/2013 | Hoeppner |
| 8,801,586 B2 | 8/2014 | Dorian et al. |
| 9,079,123 B2 * | 7/2015 | Crawford ............ B01L 3/50215 |
| 9,162,232 B2 | 10/2015 | Ellsworth |
| 2002/0023884 A1 | 2/2002 | Anderson |
| 2002/0094305 A1 | 7/2002 | Dicesare et al. |
| 2002/0098137 A1 | 7/2002 | Hommeltoft |
| 2002/0132367 A1 | 9/2002 | Miller et al. |
| 2002/0156439 A1 | 10/2002 | Iskra |
| 2002/0185778 A1 | 12/2002 | Armbruster |

(56) References Cited

U.S. PATENT DOCUMENTS

| | | |
|---|---|---|
| 2003/0028154 A1 | 2/2003 | Ross |
| 2003/0039717 A1 | 2/2003 | Hwang et al. |
| 2003/0205538 A1 | 11/2003 | Dorian et al. |
| 2004/0013575 A1 | 1/2004 | Stevens et al. |
| 2004/0043505 A1 | 3/2004 | Walenciak et al. |
| 2004/0059255 A1 | 3/2004 | Manoussakis et al. |
| 2004/0129631 A1 | 7/2004 | Anraku et al. |
| 2004/0149287 A1 | 8/2004 | Namey, Jr. |
| 2004/0166029 A1 | 8/2004 | Losada et al. |
| 2004/0210196 A1 | 10/2004 | Bush, Jr. et al. |
| 2004/0241364 A1 | 12/2004 | Zihlmann |
| 2004/0256331 A1 | 12/2004 | Arking et al. |
| 2005/0033237 A1 | 2/2005 | Fentress et al. |
| 2005/0037165 A1 | 2/2005 | Ahern et al. |
| 2005/0059163 A1 | 3/2005 | Dastane et al. |
| 2005/0124965 A1 | 6/2005 | Haywood |
| 2005/0170114 A1 | 8/2005 | Hill |
| 2005/0186120 A1 | 8/2005 | Dorian et al. |
| 2005/0261620 A1 | 11/2005 | Ballin |
| 2006/0032825 A1 | 2/2006 | Ellsworth et al. |
| 2006/0036231 A1 | 2/2006 | Conard et al. |
| 2006/0068206 A1 | 3/2006 | Hala et al. |
| 2006/0089602 A1 | 4/2006 | Boucherie |
| 2006/0116270 A1 | 6/2006 | Hatamian et al. |
| 2006/0212020 A1 | 9/2006 | Rainen et al. |
| 2006/0263266 A1 | 11/2006 | DiCesare et al. |
| 2006/0278588 A1 | 12/2006 | Woodell-May |
| 2007/0020629 A1 | 1/2007 | Ross et al. |
| 2007/0034579 A1 | 2/2007 | Dorian et al. |
| 2007/0096364 A1 | 5/2007 | Hahn et al. |
| 2007/0102344 A1 | 5/2007 | Konrad |
| 2007/0191775 A1 | 8/2007 | Diep et al. |
| 2007/0267776 A1 | 11/2007 | Conard et al. |
| 2008/0023414 A1 | 1/2008 | Konrad |
| 2008/0290048 A1 | 11/2008 | Jaeggi et al. |
| 2010/0120596 A1 | 5/2010 | Froman et al. |
| 2010/0155343 A1 | 6/2010 | Battles et al. |
| 2010/0160135 A1 | 6/2010 | Bartfeld et al. |
| 2010/0288694 A1 | 11/2010 | Crawford et al. |
| 2011/0014705 A1 | 1/2011 | Leach et al. |
| 2011/0100919 A1 | 5/2011 | Dorian et al. |
| 2011/0266206 A1 | 11/2011 | Coleman |
| 2012/0015796 A1 | 1/2012 | Leach et al. |
| 2012/0045424 A1 | 2/2012 | Esteron |
| 2012/0129676 A1 | 5/2012 | Duffy et al. |
| 2013/0017130 A1 | 1/2013 | Haubert |
| 2013/0095007 A1 | 4/2013 | Haubert et al. |

FOREIGN PATENT DOCUMENTS

| | | |
|---|---|---|
| DE | 19513453 C2 | 3/1997 |
| DE | 102010000645 A1 | 9/2011 |
| EP | 0017127 B1 | 10/1980 |
| EP | 0056609 B1 | 7/1982 |
| EP | 0119692 B1 | 9/1984 |
| EP | 0137292 B1 | 3/1990 |
| EP | 0392377 A2 | 10/1990 |
| EP | 0184274 B1 | 5/1992 |
| EP | 0385953 B1 | 4/1993 |
| EP | 0537507 A1 | 4/1993 |
| EP | 0399151 B1 | 8/1994 |
| EP | 0638804 A1 | 2/1995 |
| EP | 0520184 B1 | 1/1996 |
| EP | 0520185 B1 | 2/1996 |
| EP | 0638171 B1 | 6/1996 |
| EP | 0753741 A1 | 1/1997 |
| EP | 0494079 B1 | 3/1997 |
| EP | 0766973 A1 | 4/1997 |
| EP | 0493838 B1 | 5/1997 |
| EP | 0627261 B1 | 5/1998 |
| EP | 0640215 B1 | 11/1998 |
| EP | 0817680 B1 | 12/1999 |
| EP | 0678557 B1 | 6/2000 |
| EP | 1005910 A2 | 6/2000 |
| EP | 1016460 A2 | 7/2000 |
| EP | 0688606 B1 | 12/2000 |
| EP | 1106252 A2 | 6/2001 |
| EP | 0739229 B1 | 10/2001 |
| EP | 0744026 B1 | 11/2001 |
| EP | 1205250 A1 | 5/2002 |
| EP | 1221342 A2 | 7/2002 |
| EP | 0875757 B1 | 6/2003 |
| EP | 0928301 B1 | 1/2004 |
| EP | 1005909 B1 | 5/2004 |
| EP | 1107002 B1 | 8/2004 |
| EP | 1192996 B1 | 8/2004 |
| EP | 1106250 B1 | 4/2005 |
| EP | 1106251 B1 | 11/2005 |
| EP | 1106253 B1 | 11/2005 |
| EP | 1014088 B1 | 3/2006 |
| EP | 1006360 B1 | 5/2006 |
| EP | 1693109 A1 | 8/2006 |
| EP | 1189967 B1 | 3/2007 |
| EP | 1772191 A1 | 4/2007 |
| EP | 1509326 B1 | 6/2007 |
| EP | 1289618 B1 | 1/2008 |
| GB | 2293986 A | 4/1996 |
| JP | 56118669 A | 9/1981 |
| JP | 3270701 A | 12/1991 |
| JP | 581712 U | 11/1993 |
| JP | 9292393 A | 11/1997 |
| JP | 2000199760 A | 7/2000 |
| JP | 2003185653 A | 7/2003 |
| RU | 2062465 C1 | 6/1996 |
| WO | 9322673 A1 | 11/1993 |
| WO | 9520675 A1 | 8/1995 |
| WO | 9605770 A1 | 2/1996 |
| WO | 9607097 A1 | 3/1996 |
| WO | 9609308 A1 | 3/1996 |
| WO | 9712679 A1 | 4/1997 |
| WO | 9851411 A2 | 11/1998 |
| WO | 0114850 A1 | 3/2001 |
| WO | 0181002 A1 | 11/2001 |
| WO | 0209840 A1 | 2/2002 |
| WO | 02073190 A1 | 9/2002 |
| WO | 03035888 A1 | 5/2003 |
| WO | 03099412 A1 | 12/2003 |
| WO | 2004030826 A2 | 4/2004 |
| WO | 2004031770 A1 | 4/2004 |
| WO | 2005014173 A1 | 2/2005 |
| WO | 2005080965 A1 | 9/2005 |
| WO | 2006104636 A1 | 10/2006 |
| WO | 2006121728 A2 | 11/2006 |
| WO | 2006135856 A2 | 12/2006 |
| WO | 2007000986 A1 | 1/2007 |
| WO | 2007095450 A2 | 8/2007 |
| WO | 2008038012 A1 | 4/2008 |
| WO | 2008049359 A1 | 5/2008 |
| WO | 2008097091 A1 | 8/2008 |
| WO | 2008114998 A1 | 9/2008 |
| WO | 2008127639 A1 | 10/2008 |
| WO | 2009021257 A1 | 2/2009 |
| WO | 2011069145 A2 | 6/2011 |
| WO | 2011126867 A1 | 10/2011 |
| WO | 2012003873 A1 | 1/2012 |

* cited by examiner

FIG.35C1

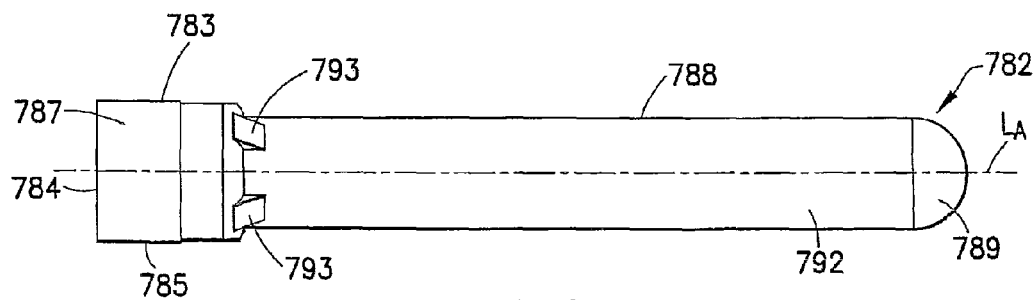
FIG.45
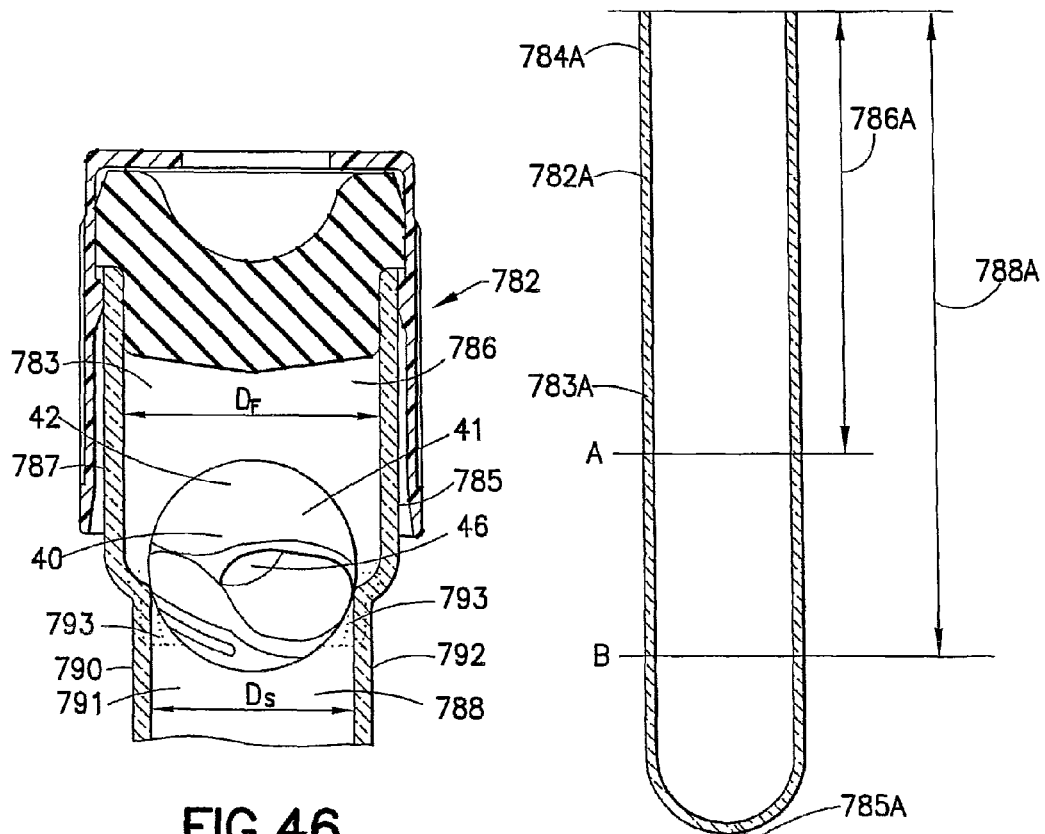
FIG.46
FIG.46A

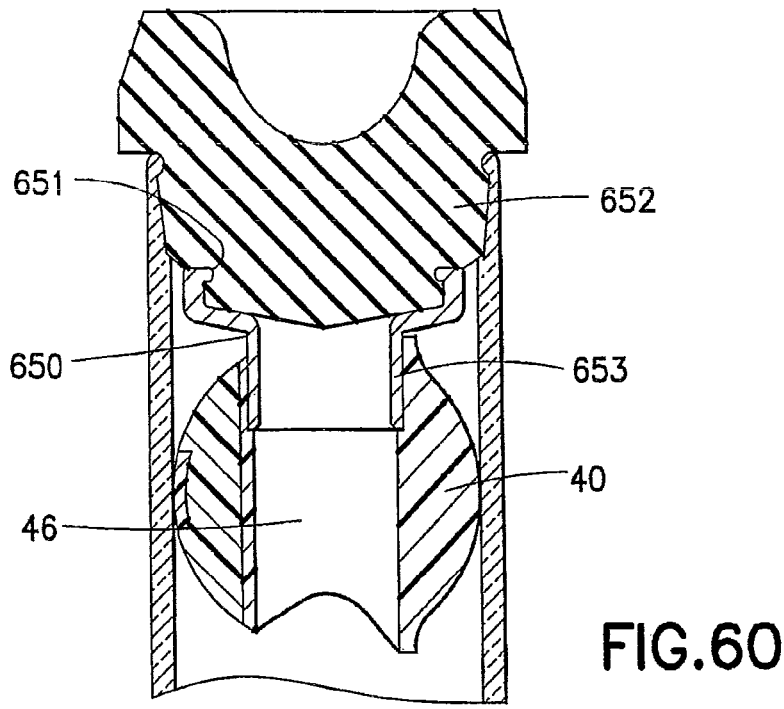
FIG.60
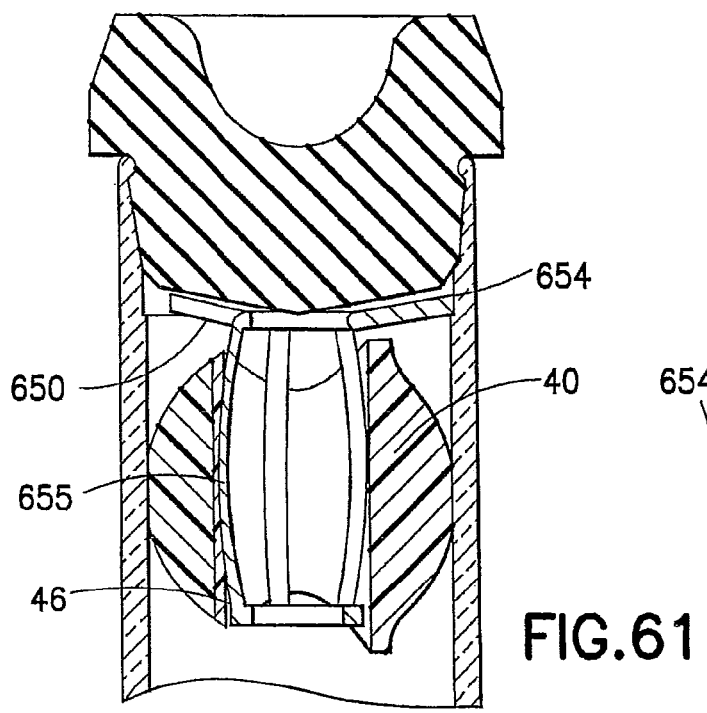 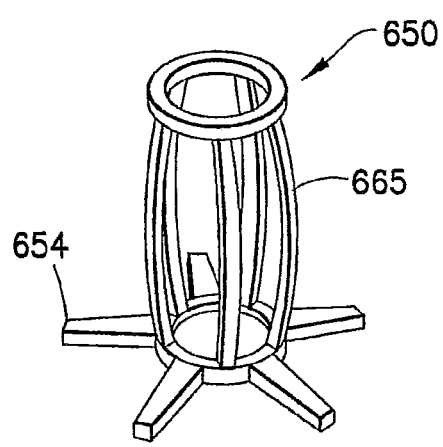
FIG.61  FIG.62

DENSITY PHASE SEPARATION DEVICE

CROSS REFERENCE TO RELATED APPLICATIONS

This application is a divisional of U.S. application Ser. No. 12/780,432, filed May 14, 2010, entitled "Density Phase Separation Device", which claims priority to U.S. Provisional Patent Application Ser. No. 61/178,599 filed May 15, 2009, the entire disclosures of each of which are hereby incorporated by reference.

BACKGROUND OF THE INVENTION

Field of the Invention

The subject invention relates to a device for separating higher and lower density fractions of a fluid sample. More particularly, this invention relates to a device for collecting and transporting fluid samples whereby the device and fluid sample are subjected to centrifugation in order to cause separation of the higher density fraction from the lower density fraction of the fluid sample.

Description of Related Art

Diagnostic tests may require separation of a patient's whole blood sample into components, such as serum or plasma (the lower density phase components), and red blood cells (the higher density phase components). Samples of whole blood are typically collected by venipuncture through a cannula or needle attached to a syringe or an evacuated blood collection tube. After collection, separation of the blood into serum or plasma and red blood cells is accomplished by rotation of the syringe or tube in a centrifuge. In order to maintain the separation, a barrier must be positioned between the higher density and lower density phase components. This allows the separated components to be subsequently examined.

A variety of separation barriers have been used in collection devices to divide the area between the higher density and lower density phases of a fluid sample. The most widely used devices include thixotropic gel materials, such as polyester gels. However, current polyester gel serum separation tubes require special manufacturing equipment to both prepare the gel and fill the tubes. Moreover, the shelf-life of the gel-based separator product is limited. Over time, globules may be released from the gel mass and enter one or both of the separated phase components. Furthermore, commercially available gel barriers may react chemically with the analytes. Accordingly, if certain drugs are present in the blood sample when it is taken, an adverse chemical reaction with the gel interface can occur. Furthermore, if an instrument probe is inserted too deeply into a collection container, then the instrument probe may become clogged if it contacts the gel.

Certain mechanical separators have also been proposed in which a mechanical barrier can be employed between the higher and lower density phases of the fluid sample. Conventional mechanical barriers are positioned between higher and lower density phase components utilizing elevated gravitational forces applied during centrifugation. For proper orientation with respect to plasma and serum specimens, conventional mechanical separators are typically positioned above the collected whole blood specimen prior to centrifugation. This typically requires that the mechanical separator be affixed to the underside of the tube closure in such a manner that blood fill occurs through or around the device when engaged with a blood collection set or phlebotomy needle. This attachment is required to prevent the premature movement of the separator during shipment, handling, and blood draw. Conventional mechanical separators are typically affixed to the tube closure by a mechanical interlock between the bellows component and the closure.

Conventional mechanical separators have some significant drawbacks. As shown in FIG. 1, conventional separators include a bellows 34 for providing a seal with the tube or syringe wall 38. Typically, at least a portion of the bellows 34 is housed within, or in contact with a closure 32. As shown in FIG. 1, as the needle 30 enters through the closure 32, the bellows 34 is depressed. This creates a void 36 in which blood may pool during insertion or removal of the needle. This can result in sample pooling under the closure, device pre-launch in which the mechanical separator prematurely releases during blood collection, trapping of a significant quantity of fluid phases, such as serum and plasma, poor sample quality, and/or barrier failure under certain circumstances. Furthermore, previous mechanical separators are costly and complicated to manufacture due to the complicated multi-part fabrication techniques.

Accordingly, a need exists for a separator device that is compatible with standard sampling equipment and reduces or eliminates the aforementioned problems of conventional separators. A need also exists for a separator device that is easily used to separate a blood sample, minimizes cross-contamination of the higher and lower density phases of the sample during centrifugation, is independent of temperature during storage and shipping, and is stable to radiation sterilization. A need further exists for a unitary separation device that requires fewer relative moving parts and that allows for enhanced ease of introducing a specimen into a collection container.

SUMMARY OF THE INVENTION

The present invention is directed to an assembly for separating a fluid sample into a higher density and a lower density phase. Desirably, the mechanical separator of the present invention may be used with a collection container, such as a tube, and is structured to move within the tube under the action of applied centrifugal force in order to separate the portions of a fluid sample. In certain configurations, the tube is a specimen collection tube including an open end, a closed end, and a sidewall extending between the open end and closed end. The sidewall includes an outer surface and an inner surface and the tube further includes a closure disposed to fit in the open end of the tube with a resealable septum. Alternatively, both ends of the tube may be open, and both ends of the tube may be sealed by elastomeric closures. At least one of the closures of the tube may include a needle pierceable resealable septum.

The mechanical separator may be disposed within the tube at a location between the top closure and the bottom of the tube. The components of the separator are dimensioned and configured to achieve an overall density for the separator that lies between the densities of the phases of a fluid sample, such as the higher and lower density phases of a blood sample.

In accordance with an embodiment of the present invention, a mechanical separator for separating a fluid sample into first and second phases within a collection container includes a separator body having a through-hole defined therein. The through-hole is adapted for allowing fluid to pass therethrough. The separator body includes a float, having a first density, and a ballast, having a second density greater than the first density. A portion of the float is connected to a portion of the ballast.

The mechanical separator may have a spheroid shape. Optionally, the float may include an exterior surface and a joining surface, and the ballast may include a contact surface connected to the joining surface of the float and an exterior surface. The exterior surface of the float and the exterior surface of the ballast taken together may form the spheroid shape.

In certain configurations, the float defines the through-hole adapted for allowing fluid to pass therethrough. The through-hole may have a circular cross-section. In other configurations, the through-hole may have an elliptical cross-section. The through-hole may be defined along a through-axis, and the float may be adapted for deformation in a direction perpendicular to the through-axis upon applied rotational force.

In another configuration, the float further includes a first extended tab adjacent a first opening of the through-hole and a second extended tab adjacent the second opening of the through-hole. At least a portion of the first extended tab and at least a portion of the second extended tab may be provided above and about the through-hole and extend radially outwardly from the float in a direction parallel to the through-axis of the separator body. Optionally, the first extended tab, an upper surface of the float, and the second extended tab may form a convex upper float surface.

In another configuration, the separator body further includes an extended tab band disposed about a portion of an outer surface of the float. Optionally, a first portion of the extended tab band is disposed adjacent a first opening of the through-hole, and a second portion of the extended tab band is disposed adjacent a second opening of the through-hole. In a further configuration, at least one of the first portion and the second portion of the extended tab band have a concave downwardly-directed orientation. Optionally, at least one of the first portion and the second portion of the extended tab band are oriented in an outwardly-extending arcuate shape about an upper portion of at least one of the first opening and second opening of the through-hole. At least one of the first portion and the second portion of the extended tab band may extend outwardly from the float in a direction parallel to the through-axis. At least a portion of the first extended portion and at least a portion of the second extended portion of the extended tab band may have the same shape and curvature. In certain configurations, the extended tab band may further include a joining portion disposed between and connecting the first extended portion and the second extended portion disposed on each connecting side of the separator body. The first extended portion and the second extended portion of the extended tab band have a concave downwardly-directed orientation, and the joining portions of the extended tab band have a concave upwardly-directed orientation. In certain configurations, the float may include the extended tab band. Optionally, the float and the extended tab band may be formed of TPE and the ballast is formed of PET.

The mechanical separator may also include an initial engagement band circumferentially disposed about the separator body. The initial engagement band may be continuous or at least partially segmented. The initial engagement band and the float may be formed of the same material. The initial engagement band may bisect at least a portion of the ballast.

In another configuration, the ballast may include a base portion and a joining structure for engaging a portion of the float. The joining structure may include a plurality of arms for engaging a portion of the float, and the joining structure may provide flexure between the float and the ballast.

Optionally, at least a portion of the float may have a circular outer perimeter having a curved cross-section perpendicular to the through-hole. In certain configurations, the float may include a joining structure for engaging a portion of the ballast. The joining structure may include a plurality of arms for engaging a portion of the ballast, and the joining structure may provide flexure between the float and the ballast.

In accordance with another embodiment of the present invention, a separation assembly for enabling separation of a fluid sample into first and second phases includes a collection container having a first end, a second end, and a sidewall extending therebetween. The collection container defines a longitudinal axis between the first end and the second end. The separation assembly further includes a mechanical separator having a separator body having a through-hole defined therein. The separator body is adapted to transition from a first initial position in which the through-hole is oriented in an open position for allowing fluid to pass therethrough, to a second sealing position in which the through-hole is oriented in a closed position for preventing fluid from being received therethrough, upon applied rotational force.

In one configuration, the separation assembly further includes a closure adapted for sealing engagement with the first end of the collection container, with the mechanical separator releasably engaged with a portion of the closure. The mechanical separator may be engaged with a portion of the closure in the first initial position, and the mechanical separator may be engaged with a portion of the sidewall of the collection container in the second sealing position. The closure may include an engagement boss disposed within a portion of the through-hole when the separator body is in the first initial position for forming a fluid seal between a portion of the separator body and the closure. Optionally, at least a portion of the through-hole of the mechanical separator is oriented along the longitudinal axis of the collection container in the first initial position, and the through-hole is oriented perpendicular to the longitudinal axis of the collection container in the second sealing position. Transition of the through-hole from the open position to the closed position may coincide with rotation of the mechanical separator from the first initial position to the second sealing position. The mechanical separator may sealingly engage a portion of the collection container wall in the second sealing position to prevent flow of fluid therethrough or thereacround.

In certain configurations, the separator body further includes a first extended tab adjacent a first opening of the through-hole and a second extended tab adjacent the second opening of the through-hole. The first extended tab and the second extended tab may engage a portion of the sidewall of the collection container in the second sealing position. In other configurations, the separator body further includes an extended tab band disposed about a portion of an outer surface of the float. The extended tab band may engage a portion of the sidewall of the collection container in the second sealing position, and the extended tab band may form a continuous seal with the sidewall of the collection container in the second sealing position.

In other configurations, the ballast includes a joining structure for engaging a portion of the float, and at least a portion of the float includes a circular outer perimeter having a curved cross-section perpendicular to the through-hole. The outer perimeter of the float may form a continuous seal with the sidewall of the collection container in the second sealing position. Optionally, the float includes a joining structure for engaging a portion of the ballast, and at least a portion of the float includes a circular outer perimeter having a curved cross-section perpendicular to the through-hole, with the outer perimeter of the float forming a continuous seal with the sidewall of the collection container in the second sealing position.

In accordance with another embodiment of the present invention, a separation assembly for enabling separation of a fluid sample into first and second phases includes a collection container having a first end, a second end, and a sidewall extending therebetween. The separation assembly further includes a mechanical separator having a separator body having a through-hole defined therein. The separator body includes a first sealing perimeter for providing sealing engagement with a first portion of a collection container while allowing a sample to pass through the through-hole into the collection container, and a second sealing perimeter for providing sealing engagement with a second portion of the collection container while maintaining a barrier for separation between the first and second phases.

The separation assembly may include a closure adapted for sealing engagement with the open end of the collection container, in which the mechanical separator is releasably engaged with a portion of the closure.

In accordance with another embodiment of the present invention, a separation assembly for enabling separation of a fluid sample into first and second phases includes a collection container having an open end, a closed end, and a sidewall extending therebetween defining an interior. The collection container further defines a longitudinal axis between the open end and the closed end. The separation assembly further includes a closure adapted for sealing engagement with the open end of the collection container, and a post engaged with the closure and adapted for positioning within the interior of the collection container. The post includes a post through-hole aligned along the longitudinal axis of the collection container. The separation assembly also includes a mechanical separator releasably engaged with the post. The mechanical separator includes a separator body having a through-hole defined therein along a through-axis, with the through-hole adapted for allowing fluid to pass therethrough. The separator body includes a float, having a first density, and a ballast, having a second density greater than the first density. A portion of the float is connected to a portion of the ballast, and a portion of the post is received within the through-hole of the separator forming a fluid path through the post and the mechanical separator in an initial first position.

The separator body may further include an initial engagement band circumferentially disposed about a portion of the separator body. The initial engagement band and the float may be formed of the same material, and the initial engagement band may bisect at least a portion of the ballast. Optionally, the separator body is adapted to transition from a first initial position in which a portion of the post is disposed within the through-hole and the separator body is oriented in an open position for allowing fluid to pass therethrough, to a second sealing position in which the separator body is disengaged from the post and the through-hole is oriented in a closed position for preventing fluid from being received therethrough, upon applied rotational force. Transition of the separator body from the open position to the closed position may include an axial movement of the separator body to disengage from the post, and a rotational movement of the separator body from an initial first position to a second sealing position.

In accordance with yet another embodiment of the present invention, a separation assembly for enabling separation of a fluid sample into first and second phases includes a collection container having an open end, a closed end, and a sidewall extending therebetween defining an interior. The collection container further defines a longitudinal axis between the open end and the closed end. The separation assembly further includes a closure adapted for sealing engagement with the open end of the collection container. The closure includes a receiving end for positioning within the open end of the collection container, with the receiving end defining an interior cavity and including an undercut protrusion extending into the interior cavity. The separation assembly further includes a mechanical separator releasably engaged with the closure. The mechanical separator includes a separator body having a through-hole defined therein along a through-axis, with the through-hole adapted for allowing fluid to pass therethrough. The separator body includes a float, having a first density, and a ballast, having a second density greater than the first density, with a portion of the float connected to a portion of the ballast. The undercut protrusion of the closure may be disposed within the through-hole of the separator, and at least a portion of the separator body may be disposed within the interior cavity of the closure in an initial first position.

In accordance with yet another embodiment of the present invention, a collection container includes a first region having an open top end and a first sidewall defining a first interior and a first exterior. The collection container also includes a second region having a closed bottom end and a second sidewall defining a second interior and a second exterior. The first region and the second region may be aligned along a longitudinal axis such that the first interior and the second interior are provided in fluid communication. A diameter of the first interior may be greater than a diameter of the second interior, and at least one fluid flute may extend between the first region and the second region to allow passage of fluid therethrough from the first region to the second region.

In certain configurations, the first exterior has a 16 mm profile and the second exterior has a 13 mm profile. The first interior may be dimensioned to accommodate a mechanical separator therein, and the second interior may be dimensioned to at least partially restrain a portion of the mechanical separator from passing therein absent applied rotational force.

In accordance with yet another embodiment of the present invention, a separation assembly for enabling separation of a fluid sample into first and second phases includes a collection container having a first region having an open top end and a first sidewall defining a first interior and a first exterior, and a second region having a closed bottom end and a second sidewall defining a second interior and a second exterior. The first region and the second region may be aligned along a longitudinal axis such that the first interior and the second interior are provided in fluid communication, with a diameter of the first interior being greater than a diameter of the second interior. The separation assembly further includes at least one fluid flute extending between the first region and the second region to allow passage of fluid therethrough from the first region to the second region. The separation assembly may also include a mechanical separator having a float, having a first density, and a ballast, having a second density greater than the first density, with a portion of the float connected to a portion of the ballast. At least a portion of the mechanical separator is prevented from entering the second region in an initial first position, and the mechanical separator is transitioned into the second region upon application of rotational force to a second sealing position.

The mechanical separator may include a separator body having a through-hole defined therein and adapted for allowing fluid to pass therethrough.

In accordance with still a further embodiment of the present invention, a separation assembly for enabling separation of a fluid sample into first and second phases includes a collection container having a first end, a second end, and a sidewall extending therebetween defining an interior. The separation assembly further includes a closure adapted for sealing engagement with the open end of the collection container. The separation assembly also includes a mechanical separator releasably restrained by at least one of the closure and the sidewall of the collection container in an initial first position. The mechanical separator includes a separator body having a through-hole defined therein along a through-axis, with the through-hole adapted for allowing fluid to pass therethrough. The separator body includes a float, having a first density, and a ballast, having a second density greater than the first density, with a portion of the float connected to a portion of the ballast. The separation assembly further includes a carrier releasably engaged with a portion of the mechanical separator in the initial position such that, upon application of rotational force, the separator body transitions from an initial position in which fluid may pass through the through-hole, to a sealing position in which the mechanical separator prevents passage of fluid therethrough or therearound. Also upon application of rotational force, the carrier disengages from the mechanical separator.

In still a further embodiment of the present invention, a separation assembly includes a separation assembly including a collection container having a first end, a second end, and a sidewall extending therebetween defining an interior. The separation assembly also includes a mechanical separator including a float and a ballast and capable of movement from a first position to a sealing position. In the sealing position, a sealing perimeter is established between at least a portion of the interior and the separator, the sealing perimeter having a varying position about a portion of the interior, with the varying position defining an average sealing height. The mechanical separator also has a maximum height and a minimum height within the collection container, such that the average sealing height is less than the maximum height minus the minimum height.

The assembly of the present invention is advantageous over existing separation products that utilize separation gel. In particular, the assembly of the present invention will not interfere with analytes, whereas many gels interact with bodily fluids and/or analytes present within a collection container. The assembly of the present invention is also advantageous over existing mechanical separators in that the separator does not require piercing of the separator body to introduce a specimen into the collection container thereby minimizing pre-launch and sample pooling under the closure. The structure of the present mechanical separator also minimizes the loss of trapped fluid phases, such as serum and plasma within the separator body. Additionally, the assembly of the present invention does not require complicated extrusion techniques during fabrication, and may optimally employ two-shot molding techniques.

Further details and advantages of the invention will become clear from the following detailed description when read in conjunction with the accompanying drawings.

BRIEF DESCRIPTION OF THE DRAWINGS

FIG. 35C1 is a cross-sectional view of the mechanical separator of FIG. 35A taken along line 35C1-35C1 of FIG. 35B.

FIG. 45 is a side view of a collection container having a first region, a second region, and a plurality of fluid flutes in accordance with an embodiment of the present invention.

FIG. 46 is a cross-sectional partial side view of a separation assembly having a mechanical separator disposed within the collection container of FIG. 45 in accordance with an embodiment of the present invention.

FIG. 46A is a cross-sectional side view of an alternative collection container for use with a mechanical separator in accordance with an embodiment of the present invention.

FIG. 60 is a cross-sectional side view of an alternative separation assembly having a mechanical separator engaged with a carrier engaged with a portion of the closure in accordance with an embodiment of the present invention.

FIG. 61 is a cross-sectional side view of an alternative separation assembly having a mechanical separator engaged with an alternative carrier engaged with a portion of the closure in accordance with an embodiment of the present invention.

FIG. 62 is a perspective view of the carrier of FIG. 61.

DESCRIPTION OF THE PREFERRED EMBODIMENTS

Figure 1:
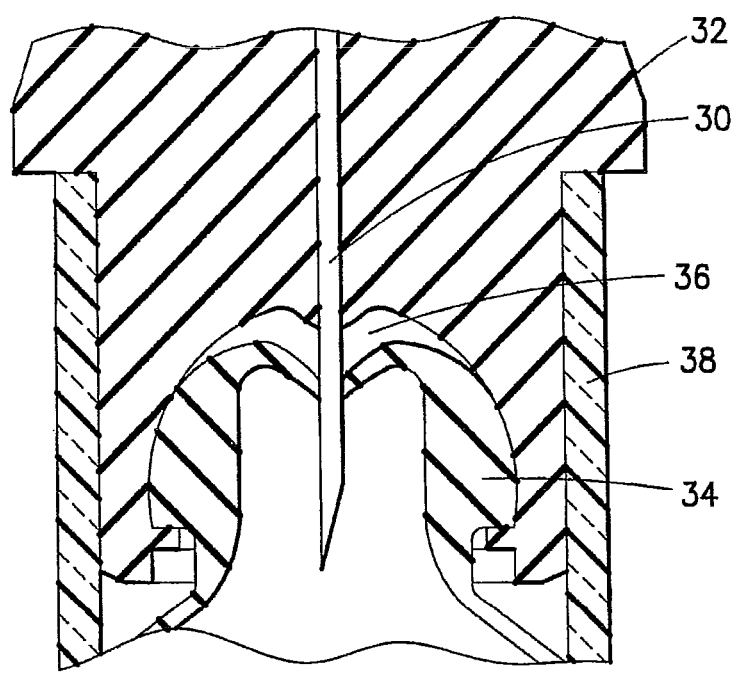
FIG. 1 is a partial cross-sectional side view of a conventional mechanical separator.
Figure 2:
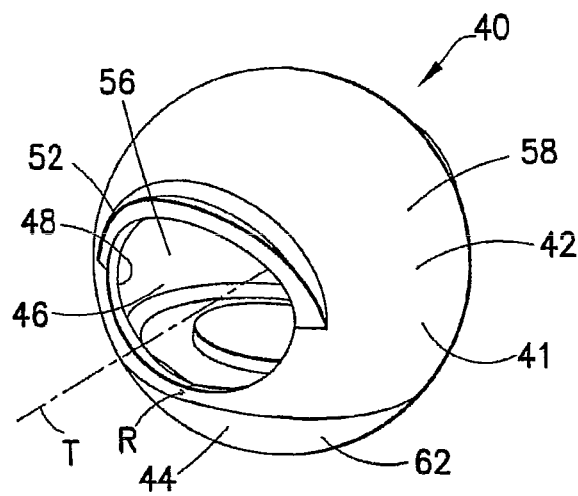
FIG. 2 is a perspective view of a mechanical separator assembly having a float defining a through-hole and a ballast in accordance with an embodiment of the present invention.

For purposes of the description hereinafter, the words "upper", "lower", "right", "left", "vertical", "horizontal", "top", "bottom", "lateral", "longitudinal", and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

The mechanical separator of the present invention is intended for use with a collection container for providing separation of a sample into higher and lower density phase components, as will be discussed herein. For example, the present mechanical separator can be used to provide a separation of serum or plasma from whole blood through the use of differential buoyancy to cause a sealing area to contract when submerged in a specimen exposed to elevated gravitational forces through applied rotational force or centrifugation. In one embodiment, the elevated gravitational forces can be provided at a rate of at least 2,000 revolutions/minute, such as at least 3,400 revolutions/minute.

Referring to FIGS. 2-8, the mechanical separator 40 of the present invention includes a separator body 41 including a float 42 and a ballast 44 connected to the float 42. In one embodiment, the float 42 has a first density and the ballast 44 has a second density, with the second density being greater than the first density. In another embodiment, the float 42 has a first buoyancy and the ballast 44 has a second buoyancy, with the first buoyancy being greater than the second buoyancy. In one embodiment, it is desirable that the float 42 of the mechanical separator 40 be made from a material having a density that is lighter than the liquid or specimen intended to be separated into two phases. For example, if it is desired to separate human blood into serum and plasma, then it is desirable that the float 42 have a density of no more than about 1.020 g/cc. In one configuration, the float 42 of the mechanical separator 40 may be extruded and/or molded of a resiliently deformable and self-sealable material, such as a thermoplastic elastomer (TPE). In yet another embodiment, the float 42 may be extruded and/or molded of a resiliently deformable material that exhibits good sealing characteristics when contact is established with a collection container, as will be discussed herein. Maintenance of the float density within the specified tolerances is more easily obtained by using a standard material that does not require compounding with, for example, glass micro-spheres in order to reduce the material density.

Figure 3:
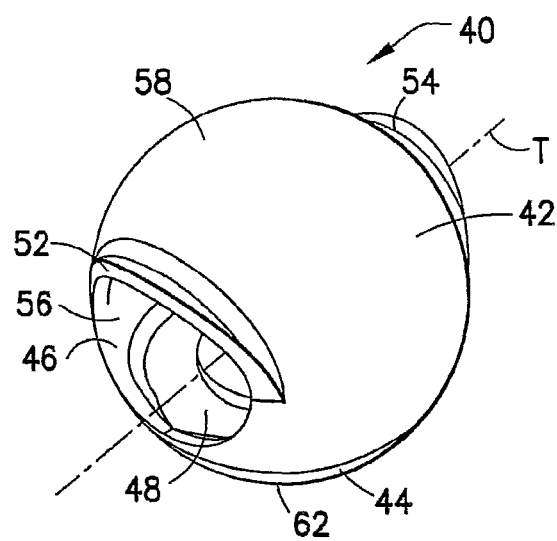
FIG. 3 is an alternative perspective view of the mechanical separator assembly of FIG. 2.
Figure 4:
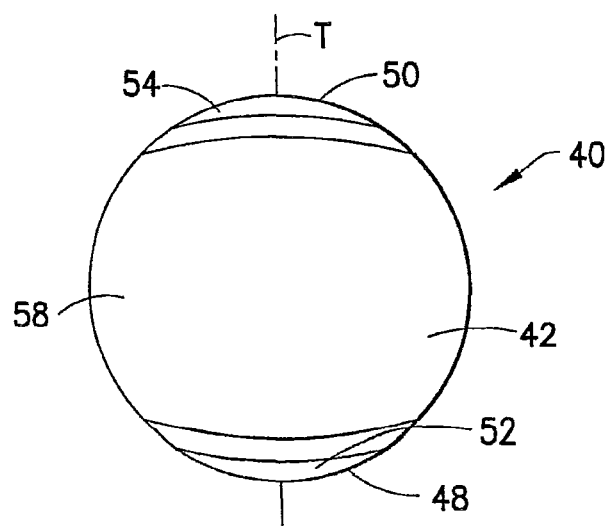
FIG. 4 is a top view of the mechanical separator of FIG. 2.
Figure 5:
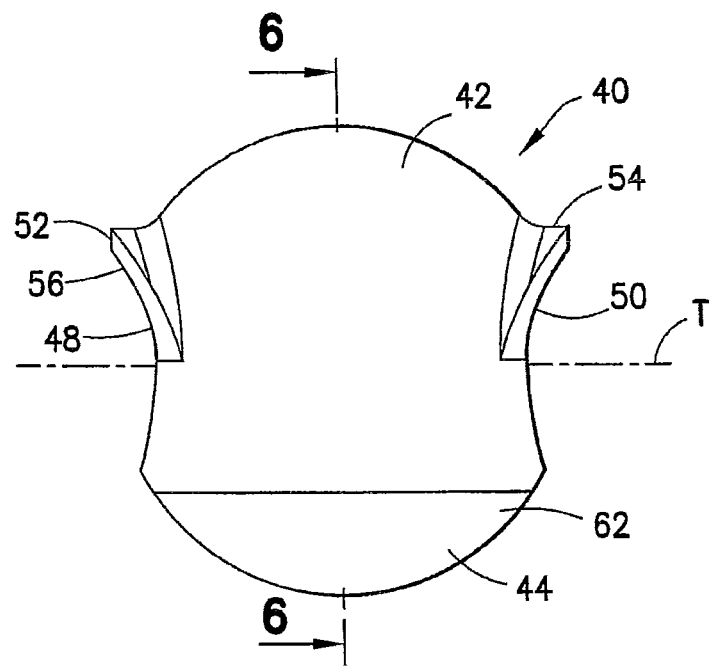
FIG. 5 is a side view of the mechanical separator of FIG. 2.
Figure 8:
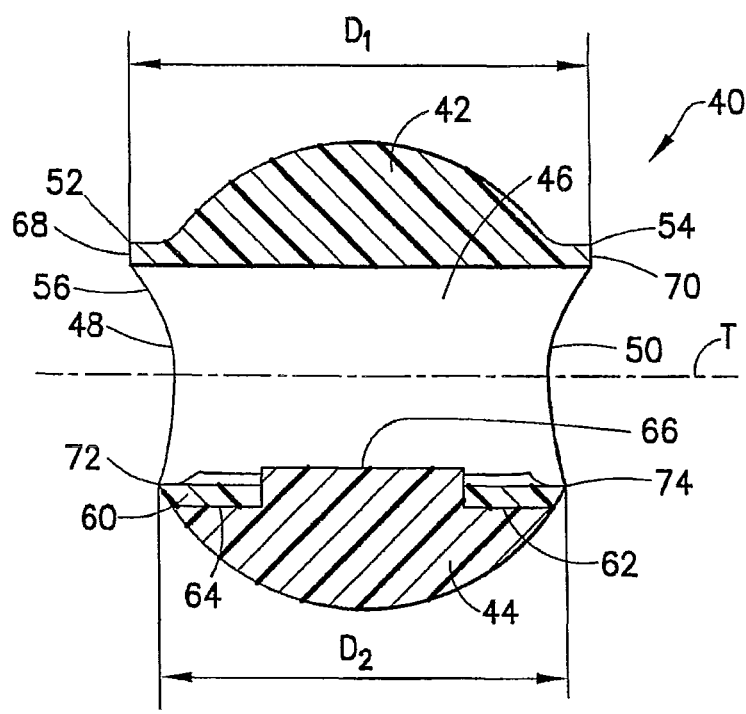
FIG. 8 is a cross-sectional view of the mechanical separator of FIG. 2 taken along line B-B of FIG. 7.

The mechanical separator 40 also includes a through-hole 46 defined therein, such as along a through-axis T of the separator body 41. As shown in FIGS. 3, 5, and 8, the through-hole 46 may extend through the entire separator body 41 and includes a first opening 48 and a second opening 50 aligned along the through-axis T. In one configuration, the through-hole 46 bisects or substantially bisects the volumetric center of the separator body 41. In one embodiment, the through-hole 46 is disposed entirely within the float 42. In a further embodiment, the float 42 may further include a first extended tab 52 adjacent the first opening 48 of the through-hole 46, and a second extended tab 54 adjacent the second opening 50 of the through-hole 46. The first extended tab 52 and/or the second extended tab 54 may be co-formed with the float 42, forming a portion of the float 42 itself. In another configuration, the first extended tab 52 and/or the second extended tab 54 may be separately formed and subsequently joined with the float 42. The first extended tab 52 and the second extended tab 54 may be provided above, such as substantially above, the through-axis T of the separator body 41. The first extended tab 52 and the second extended tab 54 may also be provided about, such as substantially about, a portion of the through-hole 46, such as in an outwardly-extending arcuate shape about an upper portion 56 of the through-hole 46. The first extended tab 52 and the second extended tab 54 may extend outwardly from the float 42 in a direction parallel or substantially parallel to the through axis T of the separator body 41, such that the first extended tab 52 and the second extended tab 54 may have the same shape and curvature or substantially the same shape and curvature. In yet another embodiment, as shown in FIG. 8, the first extended tab 52 includes a first outermost edge 68 at the upper outermost portion of a first side of the through-hole 46, and the second extended tab 54 includes a second outermost edge 70 at the corresponding upper outermost portion of a second side of the through-hole 46. In one configuration, the first outermost edge 68 extends outwardly a distance that is greater than the lower outermost portion 72 of the first side of the through-hole 46. The second outermost edge 70 also extends outwardly a distance that is greater than the corresponding lower outermost portion 74 of the second side of the through-hole 46. Accordingly, the diameter $D_1$ of the separator body 41 taken about the first extended tab 52 and the second extended tab 54 about an upper portion of the through-hole 46 is slightly greater than the diameter $D_2$ of the separator body 41 taken about the lower portion of the through-hole 46 defined by the lower outermost portions 72, 74.

Figure 6:
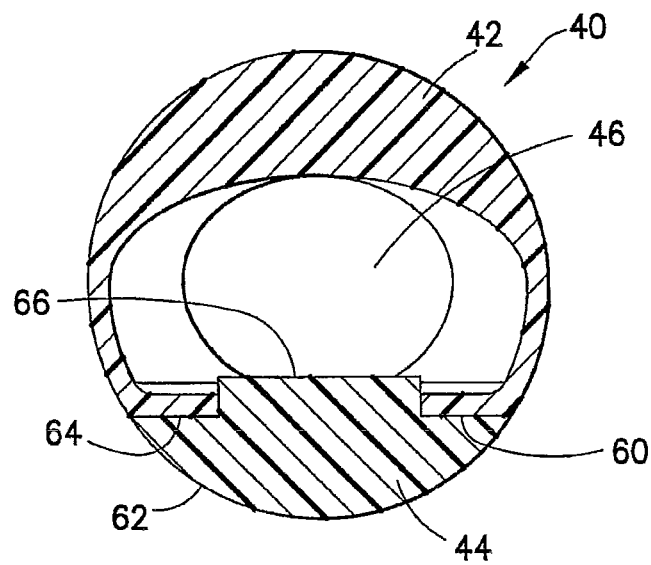
FIG. 6 is a cross-sectional view of the mechanical separator of FIG. 2 taken along line A-A of FIG. 5.
Figure 7:
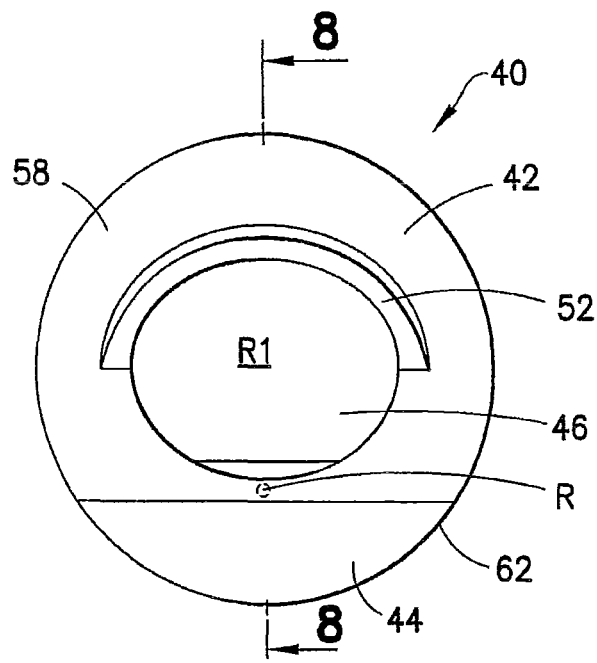
FIG. 7 is a front view of the mechanical separator of FIG. 2.

In one embodiment, the float 42 has an exterior surface 58 that is generally arcuate in shape, such as at least partially rounded or substantially rounded, and a joining surface 60, shown in FIGS. 6 and 8, adapted for engagement with a portion of the ballast 44. The ballast 44 also includes an exterior surface 62 that is generally arcuate in shape, such as at least partially rounded or substantially rounded, and a contact surface 64, also shown in FIGS. 6 and 8, that is adapted for joining with the joining surface 60 of the float 42. In one embodiment, when taken together, the exterior surface 58 of the float 42 and the exterior surface 62 of the ballast 44 form a generally round exterior, such as a spheroid shape. It is understood herein that the term "spheroid shape" may include other configurations, in addition to a perfect sphere, that are aspects of the invention which may provide slightly non-uniform diameters taken through the mid-point. For example, different planes taken through the float 42 and ballast 44 which bisect the midpoint of the mechanical separator 40 may have varying diameter and still give rise to a generally rounded or ball-like mechanical separator 40 having a spheroid shape. In one embodiment, the float 42 and the ballast 44 may be separately formed and subsequently assembled. In another embodiment, the float 42 and the ballast 44 may be co-formed, such as co-extruded and/or co-molded, such as by a two-shot or multi-shot molding process such that both components are integrally linked together to form a complete separator body 41. In another configuration, this integral linkage between the float 42 and the ballast 44 may be created by a material bond between the two components, by a mechanical interlock, or by a combination of a material bond and a mechanical interlock. In addition, the float 42 and the ballast 44 may be linked together by a separate post-molding operation, such as adhesive, heat-staking, and/or ultrasonic welding. As shown in FIGS. 6 and 8, the ballast 44 may include an attachment protrusion 66 which assists in the engagement of the ballast 44 and the float 42.

In one embodiment, it is desirable that the ballast 44 of the mechanical separator 40 be made from a material having a higher density than the liquid intended to be separated into two phases. For example, if it is desired to separate human blood into serum and plasma, then it is desirable that the ballast 44 have a density of at least 1.029 g/cc. In one embodiment, the ballast 44 can be formed from mineral filled polypropylene. It is anticipated herein that both the float 42 and the ballast 44 could be formed of various other materials with sufficient biocompatibility, density stability, additive compatibility, and neutrality to analyte interactions, adsorption, and leachability.

Due to the differential densities of the float 42 and the ballast 44, the mechanical separator 40 includes a center of mass R that is offset from the center of volume R1 of the separator body 41. Specifically, the volume of the separator body 41 accounted for by the float 42 may be significantly greater than the volume of the separator body 41 accounted for by the ballast 44. Accordingly, in certain embodiments, the center of mass R of the separator body 41 may be offset from the through-hole 46.

Figure 9:
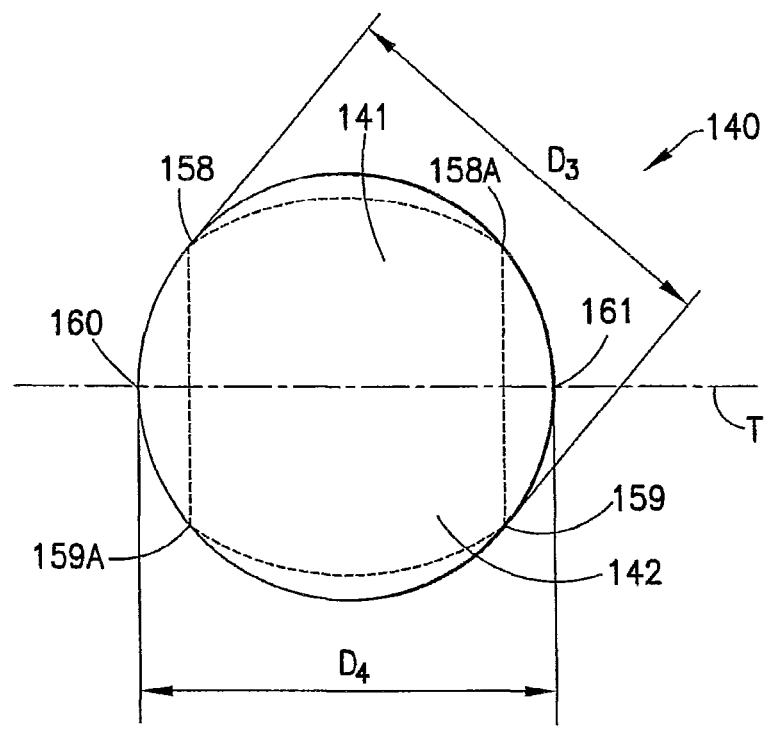
FIG. 9 is a top view of an alternative mechanical separator having a float defining a through-hole and a ballast, with first and second extended tabs forming a substantially convex upper float surface in accordance with an embodiment of the present invention.
Figure 10:
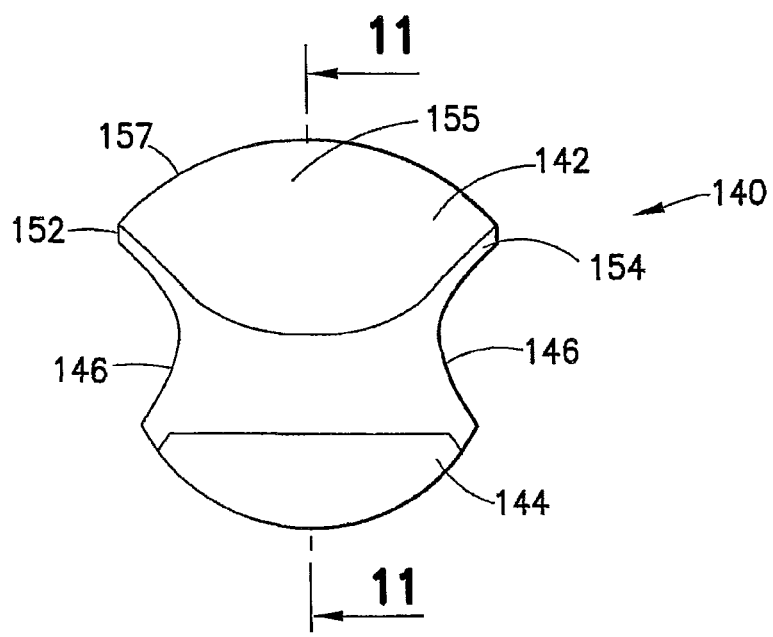
FIG. 10 is a side view of the mechanical separator of FIG. 9.
Figure 11:
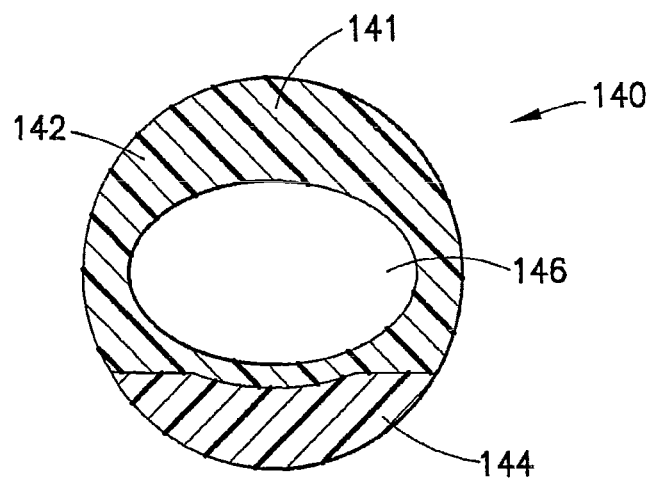
FIG. 11 is a cross-sectional view of the mechanical separator of FIG. 9 taken along line C-C of FIG. 10.
Figure 12:
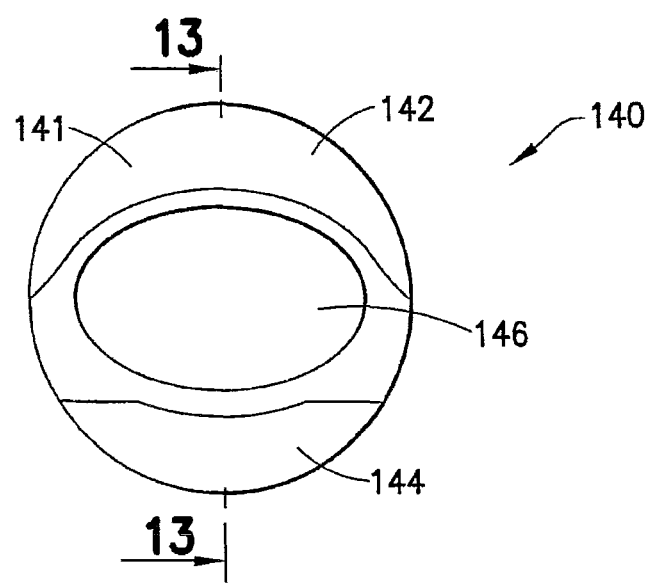
FIG. 12 is a front view of the mechanical separator of FIG. 9.
Figure 13:
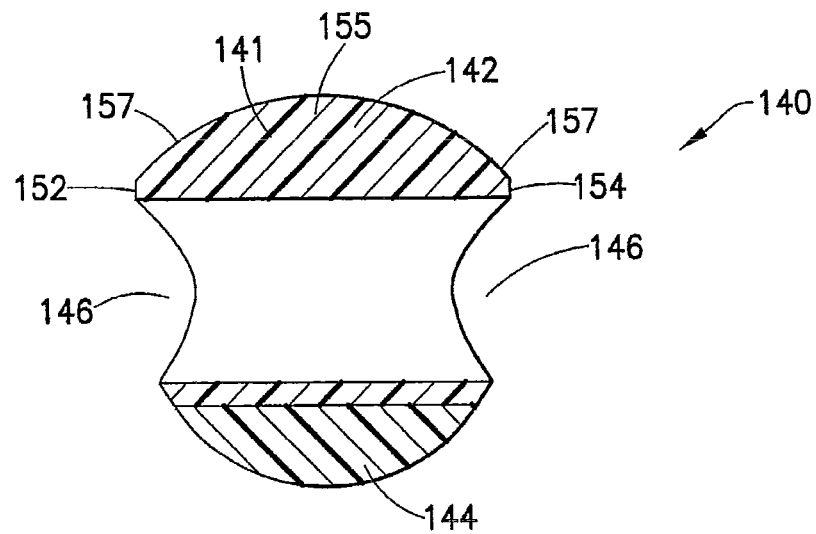
FIG. 13 is a cross-sectional view of the mechanical separator of FIG. 9 taken along line D-D of FIG. 12.
Figure 14:
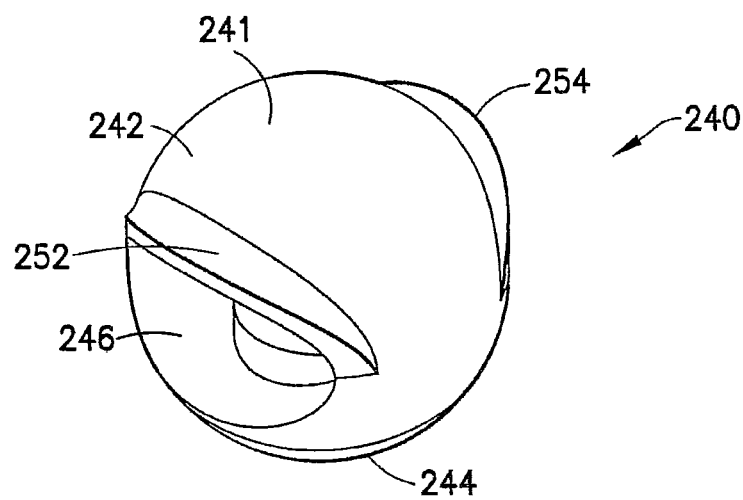
FIG. 14 is a perspective view of an alternative mechanical separator having a float defining an elliptical through-hole and a ballast in accordance with an embodiment of the present invention.
Figure 15:
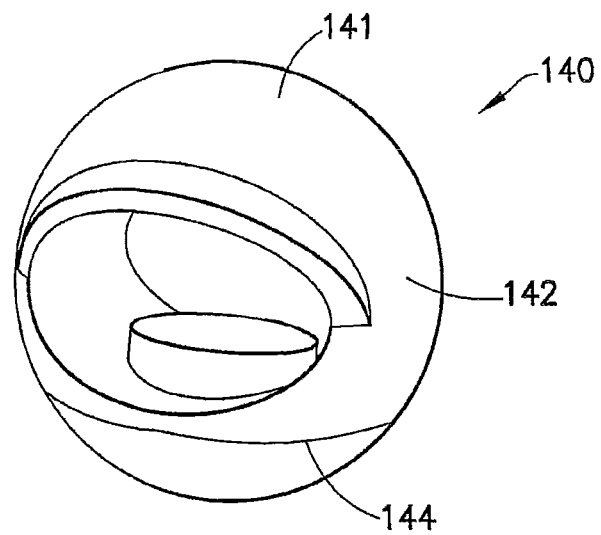
FIG. 15 is an alternative perspective view of the mechanical separator of FIG. 14.
Figure 16:
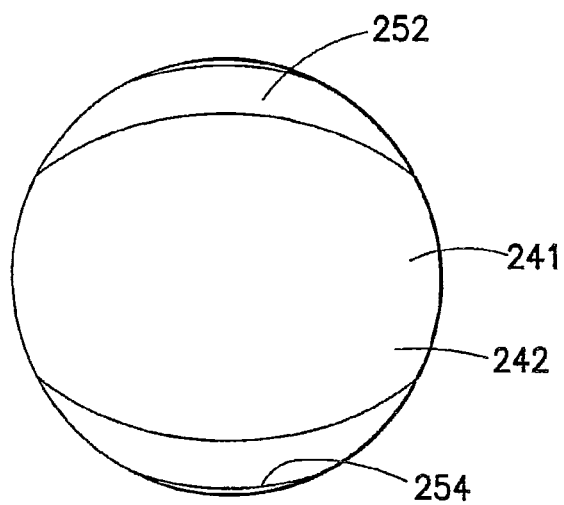
FIG. 16 is a top view of the mechanical separator of FIG. 15.
Figure 17:
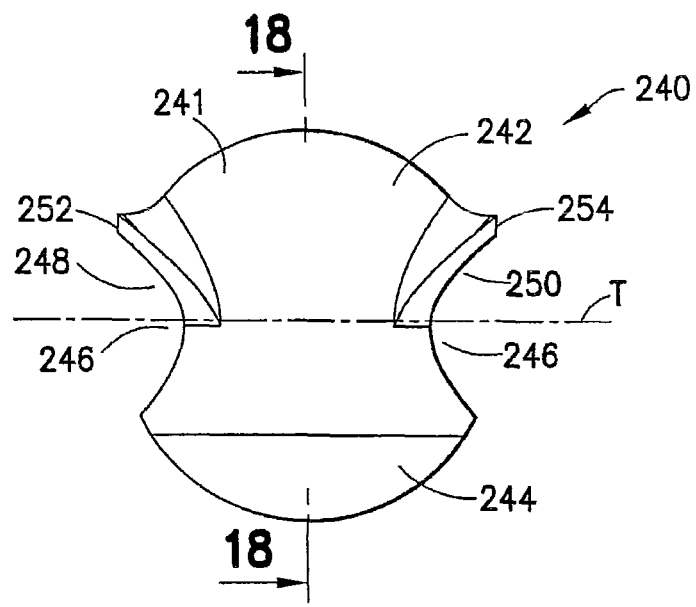
FIG. 17 is a side view of the mechanical separator of FIG. 15.

In accordance with another embodiment of the present invention, as shown in FIGS. 9-13, the mechanical separator 140 includes a separator body 141 having a float 142 and a ballast 144 with a through-hole 146 defined within the float 142, as discussed above. In this configuration, shown specifically in FIGS. 10 and 13, the first extended tab 152 and the second extended tab 154, taken with an upper portion 155 of the float 142, form a substantially convex upper float surface 157. As shown in FIG. 9, the profile of the separator body 141 is slightly off-spherical such that a diameter $D_3$ of the separator body extending between diagonally off-set endpoints 158, 159 of the through-hole 146 extending along the through-axis T, is slightly larger than a diameter $D_4$ of the separator body extending between outermost opposing endpoints 160, 161 tangent to the perimeter of the separator body 141 and perpendicular to the through-hole 146. Accordingly, the endpoints (diagonally off-set endpoints 158, 159, and second diagonally off-set endpoints 158A, 159A) may each include a thickened area of material, such as TPE.

Figure 18:
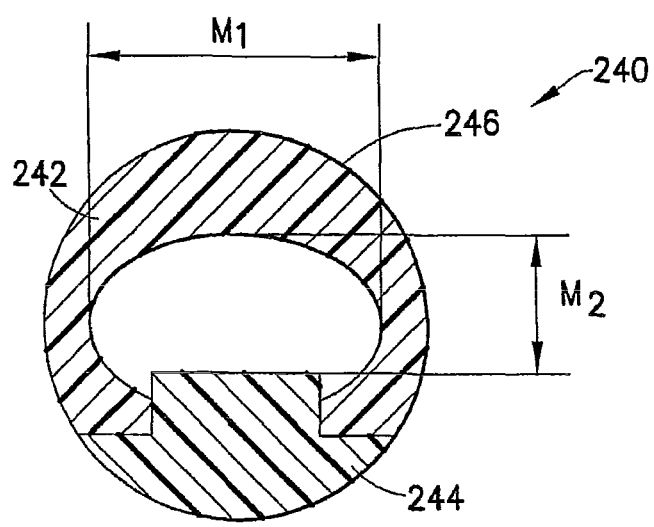
FIG. 18 is a cross-sectional view of the mechanical separator of FIG. 15 taken along line E-E of FIG. 17.
Figure 19:
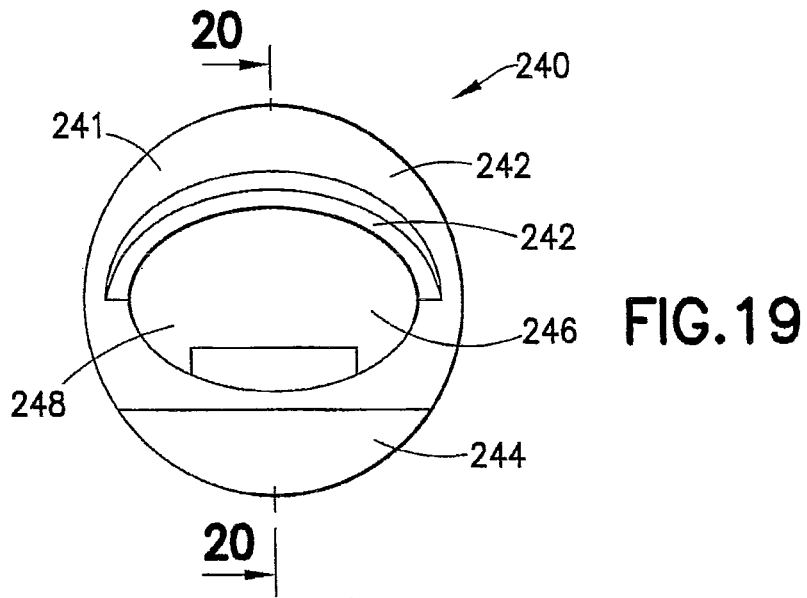
FIG. 19 is a front view of the mechanical separator of FIG. 15.

In accordance with another embodiment, as shown in FIGS. 14-20, the mechanical separator 240 includes a separator body 241 having a float 242 and a ballast 244 with a through-hole 246 defined within the float 242, as discussed above. In this configuration, the through-hole 246 may have a substantially elliptical cross-section, as specifically shown in FIGS. 18-19. In one embodiment, the major axis $M_1$ of the ellipse, shown in FIG. 18, is oriented perpendicular to the through-axis T, shown in FIG. 17. By extending the major axis $M_1$ of the ellipse perpendicular to the through-axis T, the float 242 may be adapted for increased elongation in the direction of the minor axis $M_2$ (shown in FIG. 18) of the ellipse upon application of rotational force, as will be discussed herein.

In this configuration, the curvature of the first extended tab 252 and the curvature of the second extended tab 254 are elongated to substantially mimic at least a portion of the elliptical first opening 248 and second opening 250 of the through-axis T, respectively. In another embodiment, the first extended tab 252 is at least partially curved in shape, such as having a convex shape, and is provided adjacent the upper portion of the first opening 248 of the through-hole 246. The second extended tab 254 may also be at least partially curved in shape, such as having a convex shape, and may be provided adjacent the upper portion of the second opening 250 of the through-hole 246.

Figure 20:
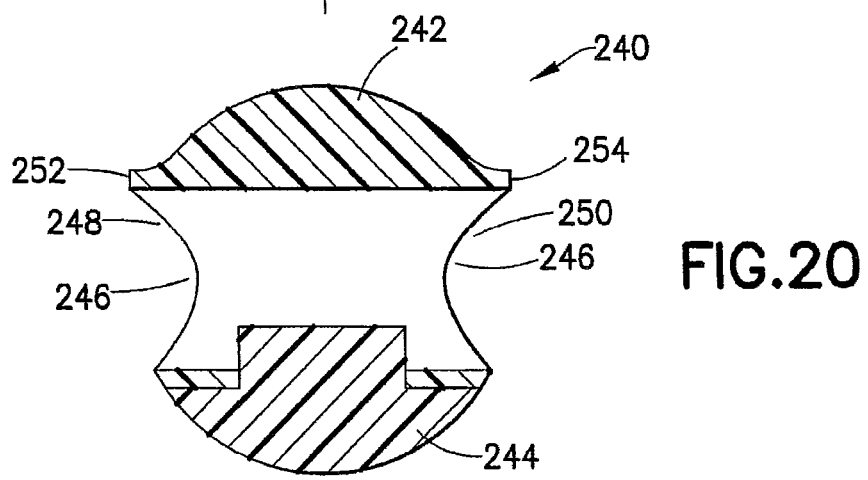
FIG. 20 is a cross-sectional view of the mechanical separator of FIG. 15 taken along line F-F of FIG. 19.
Figure 20A:
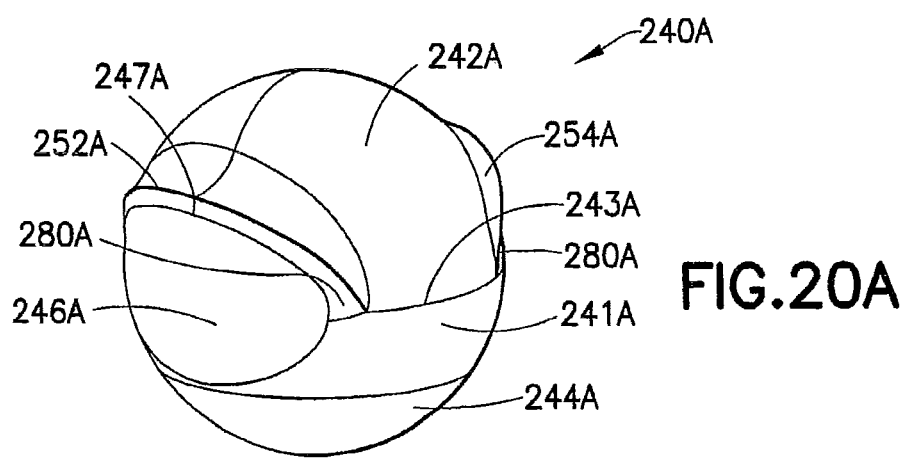
FIG. 20A is a perspective view of a mechanical separator having a spheroid shaped body and a reduced separation between the first extended tab and the second extended tab in accordance with an embodiment of the present invention.

As shown in FIG. 20A, the mechanical separator 240A includes a separator body 241A having a float 242A and a ballast 244A with a through-hole 246A defined within the float 242A, as discussed above. In this configuration, the first extended tab 252A and the second extended tab 254A may have an elliptical profile that is substantially coincident to the diameter 243A of the separator body 241A at the edges of the through-hole 246A, and slightly offset from the diameter 243A at the apex 247A of the first and second extended tabs 252A, 254A. In this configuration, the first extended tab 252A and the second extended tab 254A may include enlarged fillets 280A positioned at the edges of the first and second extended tabs 252A, 254A adjacent the through-hole 246A to assist in the formation of a barrier against a portion of the tube wall in the sealing position, as described herein. The enlarged fillets 280A may function to facilitate the shedding of cells around the mechanical separator during application of applied rotational force, as described herein. The enlarged fillets 280A may also include a region of the first and second extended tabs 252A, 254A having an increased thickness and/or diameter, such as a widened taper adjacent the ends of the first and second extended tabs 252A, 254A and extending along at least a portion of the through-hole 246A.

Figure 21:
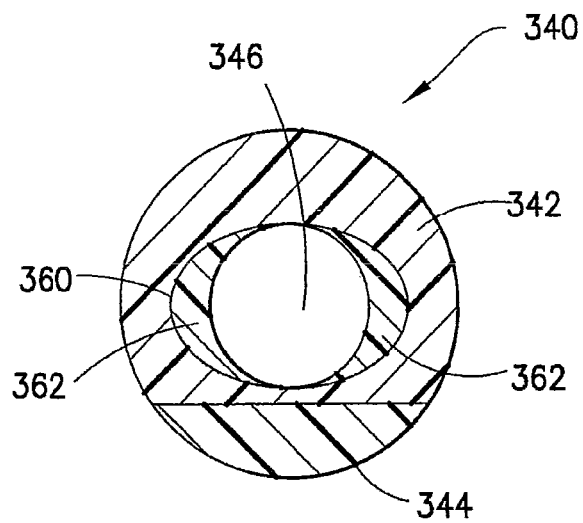
FIG. 21 is a cross-sectional view of an alternative mechanical separator having an elliptical interior taken along a similar cross-sectional line as that shown in FIG. 18.
Figure 22:
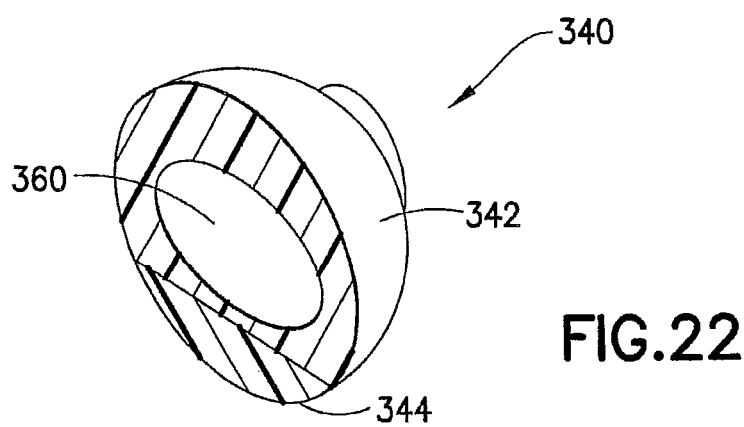
FIG. 22 is a partial perspective view of the mechanical separator having an elliptical interior as shown in FIG. 21.
Figure 23:
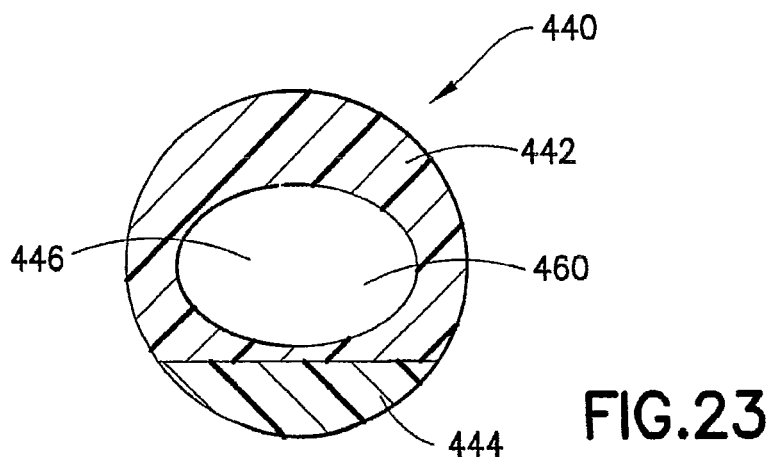
FIG. 23 is a cross-sectional view of an alternative mechanical separator having an elliptical through-hole taken along a similar cross-sectional line as that shown in FIG. 18.
Figure 24:
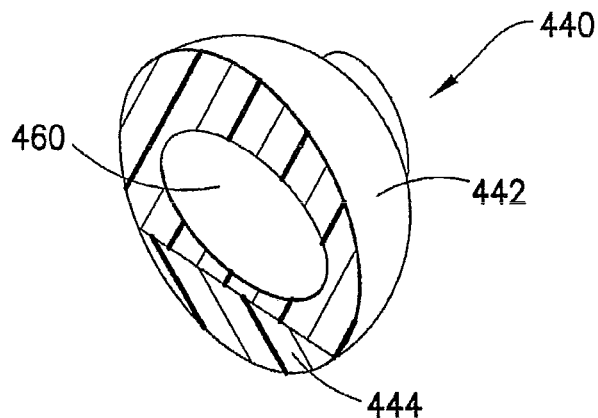
FIG. 24 is a partial perspective view of the mechanical separator having an elliptical through-hole as shown in FIG. 23.
Figure 25:
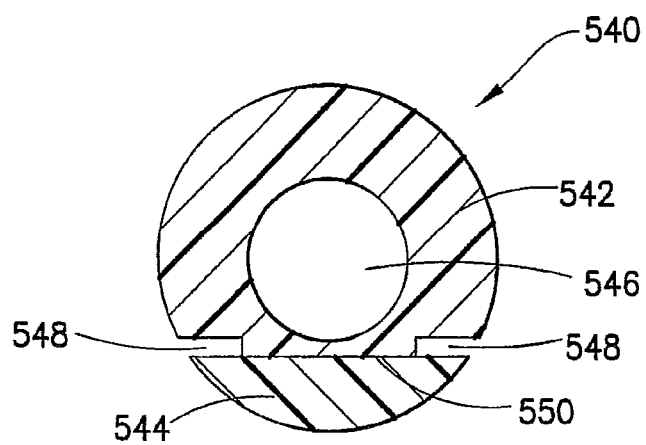
FIG. 25 is a cross-sectional view of an alternative mechanical separator having a substantially round interior and side-cuts taken along a similar cross-sectional line as that shown in FIG. 18.
Figure 26:
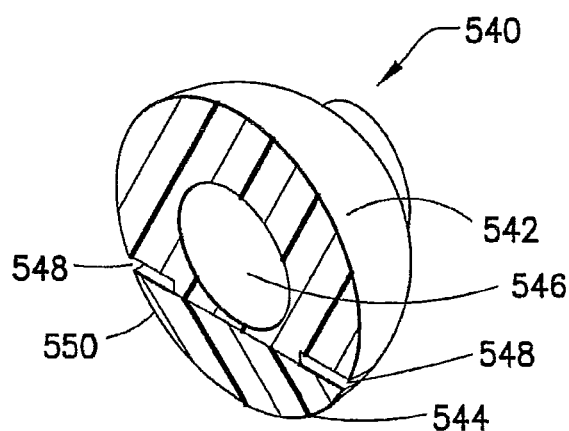
FIG. 26 is a partial perspective view of the mechanical separator having a substantially round interior and side-cuts as shown in FIG. 25.

As shown in FIGS. 21-22, a mechanical separator 340 of the present invention includes a float 342 and a ballast 344, and may include an elliptical interior 360 defining a substantially cylindrical through-hole 346. In this configuration, the elliptical interior 360 may include a filler material 362 dimensioned to fill the elliptical interior 360 leaving a substantially cylindrical though-hole 346. In one embodiment, the filler material 362 may be a TPE material or other sufficiently flexible material. Alternatively, as shown in FIGS. 23-24, a mechanical separator 440 of the present invention, including a float 442 and a ballast 444, may include an elliptical interior 460 defining an elliptical through-hole 446. In yet another configuration, a mechanical separator 540 of the present invention, including a float 542 and a ballast 544, may include a through-hole 546 having a circular cross-section and a cylindrical shape. Optionally, the float 542 may also include a slit 548 or plurality of slits 548, such as adjacent an interface 550 with the ballast 544. The inclusion of a slit 548 or a plurality of slits 548 defined within the float 542 may provide for increased elongation of the float 542 upon application of rotational force, as will be discussed herein.

Figure 27:
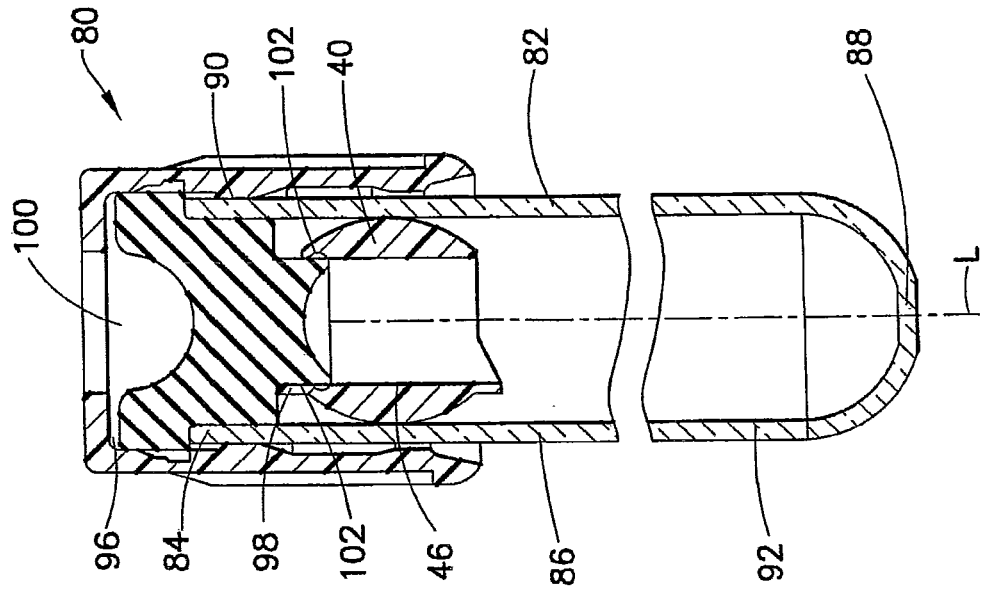
FIG. 27 is a partial cross-sectional side view of a mechanical separator of the present invention affixed to a closure in accordance with an embodiment of the present invention.

As shown in FIG. 27, the mechanical separator 40 of the present invention may be provided as a portion of a separation assembly 80 for separating a fluid sample into first and second phases within a collection container 82 having a closure 84. Specifically, the collection container 82 may be a sample collection tube, such as a proteomics, molecular diagnostics, chemistry sample tube, blood, or other bodily fluid collection tube, coagulation sample tube, hematology sample tube, and the like. Desirably, collection container 82 is an evacuated blood collection tube. In one embodiment, the collection container 82 may contain additional additives as required for particular testing procedures, such as protease inhibitors, clotting agents, and the like. Such additives may be in particle or liquid form and may be sprayed onto the cylindrical sidewall 86 of the collection container 82 or located at the bottom of the collection container 82. The collection container 82 includes a closed bottom end 88, an open top end 90, and a cylindrical sidewall 92 extending therebetween. The cylindrical sidewall 92 includes an inner surface 94 with an inside diameter extending substantially uniformly from the open top end 90 to a location substantially adjacent the closed bottom end 88 along the longitudinal axis L of the collection container 82.

The collection container 82 may be made of one or more than one of the following representative materials: polypropylene, polyethylene terephthalate (PET), glass, or combinations thereof. The collection container 82 can include a single wall or multiple wall configurations. Additionally, the collection container 82 may be constructed in any practical size for obtaining an appropriate biological sample. For example, the collection container 82 may be of a size similar to conventional large volume tubes, small volume tubes, or microtainer tubes, as is known in the art. In one particular embodiment, the collection container 82 may be a standard 13 ml evacuated blood collection tube, as is also known in the art.

The open top end 90 is structured to at least partially receive the closure 84 therein to form a liquid impermeable seal. The closure 84 includes a top end 96 and a bottom end 98 structured to be at least partially received within the collection container 82. Portions of the closure 84 adjacent the top end 90 define a maximum outer diameter which exceeds the inside diameter of the collection container 82. In one embodiment, the closure 84 includes a pierceable resealable septum 100 penetrable by a needle cannula (not shown). Portions of the closure 84 extending downwardly from the bottom end 98 may taper from a minor diameter which is approximately equal to, or slightly less than, the inside diameter of the collection container 82 to a major diameter that is greater than the inside diameter of the collection container 82 at the top end 96. Thus, the bottom end 98 of the closure 84 may be urged into a portion of the collection container 82 adjacent the open top end 90. The inherent resiliency of closure 84 can insure a sealing engagement with the inner surface 94 of the cylindrical sidewall 86 of the collection container 82. In one embodiment, the closure 84 can be formed of a unitarily molded elastomeric material, having any suitable size and dimensions to provide sealing engagement with the collection container 82. Optionally, the closure 84 may be at least partially surrounded by a shield, such as a Hemogard® Shield commercially available from Becton, Dickinson and Company.

Figure 29:
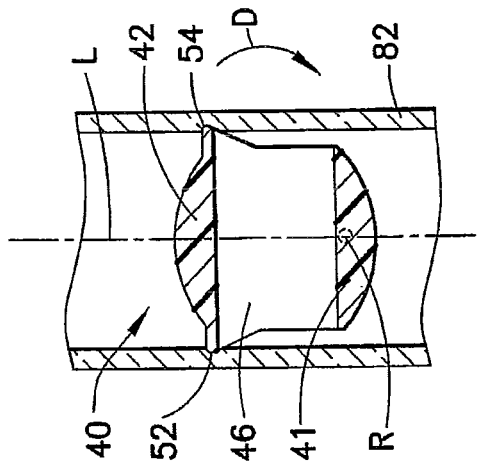
FIG. 29 is a partial cross-sectional side view of a mechanical separator disposed within a collection container as shown in FIG. 28 in a sealing position for establishing a barrier between lighter and denser phases within a collection container after application of rotational force in accordance with an embodiment of the present invention.
Figure 28:
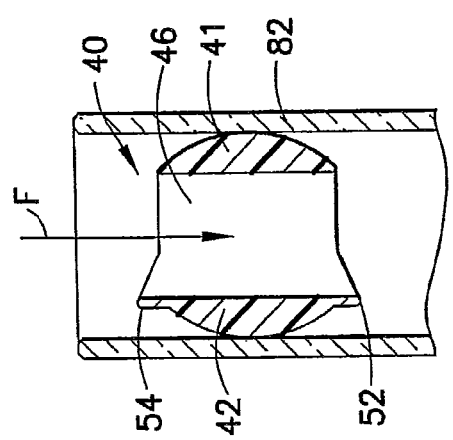
FIG. 28 is a partial cross-sectional side view of a mechanical separator disposed within a collection container in an initial position for allowing fluid to pass through the through-hole in accordance with an embodiment of the present invention.

As shown in FIG. 27, the mechanical separator 40 of the present invention may be oriented within the collection container 82 in an initial position in which the through-hole 46 of the mechanical separator 40 is aligned with the open top end 90 of the collection container 82. In the initial position, the through-hole 46 is adapted for allowing fluid to pass therethrough, such as from a needle cannula (not shown) which has pierced the pierceable septum 100 of the closure 84 and is provided in fluid communication with the interior of the collection container 82. The mechanical separator 40 may also be releasably engaged with a portion of the closure 84 such that the separator body 41 may transition from the initial position, as shown in FIGS. 27-28, to a sealing position, as shown in FIG. 29. In the initial position, the through-hole 46 is oriented in an open position for allowing fluid to pass therethrough in the direction indicated in FIG. 28 by flow arrow F. Referring to FIG. 27, the initial open position of the through-hole 46 is substantially aligned with the longitudinal axis L of the collection container 82. Referring to FIG. 29, upon application of rotational force, such as during centrifuge, the mechanical separator 40 deforms sufficiently to disengage from engagement with the closure 84 and rotate in the direction shown by directional arrow D of FIG. 29 to the sealing position in which the through-hole 46 is in a substantially closed position. In the substantially closed position, the float 42 including the first extended tab 52 and the second extended tab 54 form a sealing engagement with the inner surface 94 of the collection container 82 substantially preventing fluid from being received through the through-hole 46 or around the separator body 41.

In one configuration, the through-hole 46 is substantially aligned with the open top end 90 of the collection container 82 along at least a portion of the longitudinal axis L in the open position, and the through-hole 46 is substantially aligned perpendicular to the longitudinal axis in the closed position. It is noted that transition of the through-hole 46 from the open position to the closed position coincides with the rotation of the mechanical separator 40 from a first initial position to a second closed position. In another configuration, the mechanical separator 40 is engaged with a portion of the closure 84 in the first initial position, and the mechanical separator 40 is engaged with a portion of the sidewall 86 of the collection container 82 in the second sealing position. Referring again to FIG. 27, the closure 84 may include an engagement boss 102 for engagement with the mechanical separator 40. In one configuration, the engagement boss 102 is disposed within a portion of the through-hole 46 when the separator body 41 is in the first initial position for forming a fluid seal between a portion of the separator body 41 and the closure 84.

Figure 30:
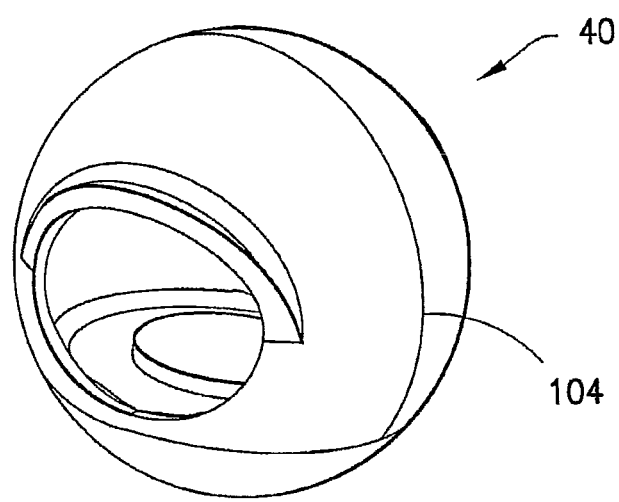
FIG. 30 is a perspective view of a mechanical separator in accordance with an embodiment of the present invention having a seal line for engagement with a collection container in an initial position.

In the initial position, the mechanical separator 40 may be attached to the closure 84 be means of a mechanical snap created by an undercut in the through-hole 46 which controls the release load of the mechanical separator 40. When the mechanical separator 40 is attached to the closure 84, it forms a seal with the sidewall 86 of the collection container 82 along a first sealing perimeter 104 as shown in FIG. 30. During specimen draw into the collection container 82, the first sealing perimeter 104 prevents the accumulation of blood between the mechanical separator 40 and the closure 84. This reduces the formation of clots and/or fibrin strands which may disrupt function of the mechanical separator 40. Upon application of rotational force and transition of the mechanical separator 40 as shown in FIG. 29, the mechanical separator 40 experiences a rotational moment while still attached to the closure 84 and, after release from the closure 84, rotates approximately 90° to become oriented with the ballast 44 facing the bottom end 88 of the collection container 82.

Figure 31:
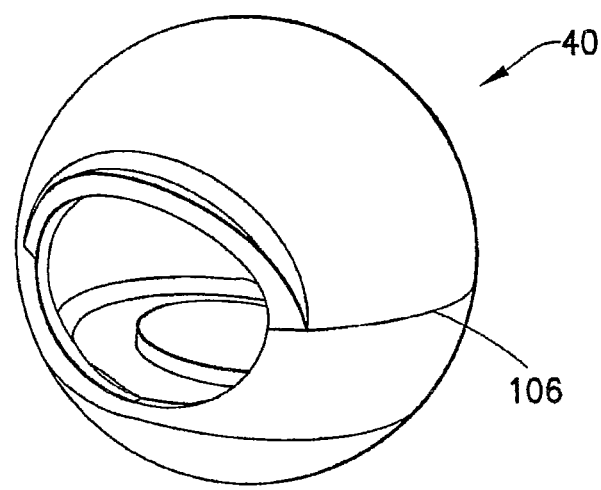
FIG. 31 is a perspective view of the mechanical separator of FIG. 30 having a seal line for engagement with a collection container in a sealing position.

Once the mechanical separator 40 contacts the fluid contained within the collection container 82, air that occupies the through-hole 46 is progressively displaced by the fluid as the device submerges. When the mechanical separator 40 is submerged in the fluid, the float 42 has a greater buoyancy than the ballast 44, which generates a differential force across the mechanical separator. During centrifugation, the differential force causes the float 42 component to elongate and contract away from the sidewall 86 of the collection container 82, thereby reducing the effective diameter and opening a communicative pathway for the flow of fluid, such as higher and lower density phase components, past the separator body 41. It is noted that the float 42 may be adapted for deformation in a direction substantially perpendicular to the through-hole 46. As the applied rotational force is removed, the float 42 recovers and the sealing area defined by the float 42 and the first extended tab 52 and the second extended tab 54 re-expands to seal against the inner surface 94 of the collection container along a second sealing perimeter 106, as shown in FIG. 31. Accordingly, the mechanical separator 40 is adapted to prevent fluid from passing between or around the separator body 41 and the collection container 82, and also prevents fluid from passing through the through-hole 46, effectively establishing a barrier. The second sealing perimeter 106 establishes a barrier between higher and lower density phases within the sample.

Figure 31A:
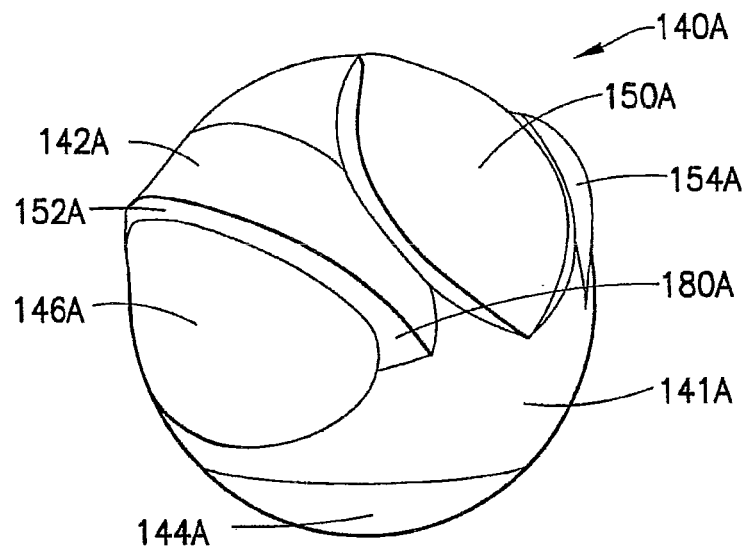
FIG. 31A is a perspective view of a mechanical separator having a partially scalloped surface in accordance with an embodiment of the present invention.
Figure 31B:
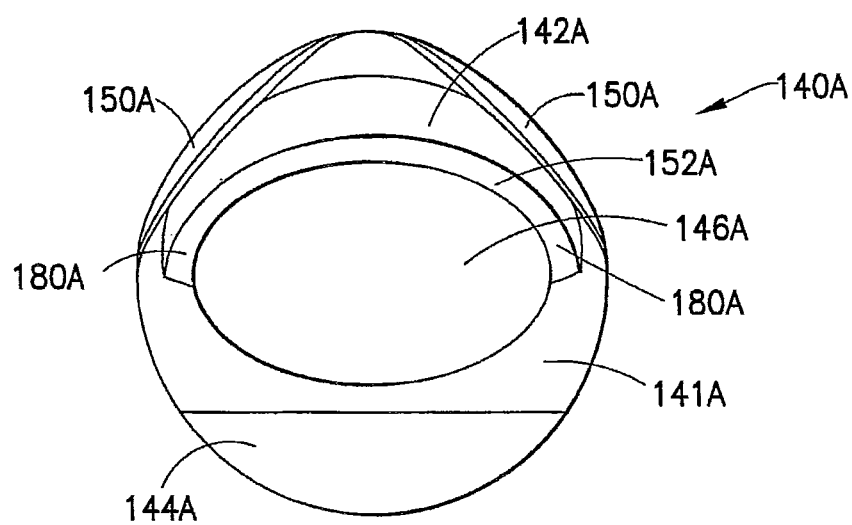
FIG. 31B is a front view of the mechanical separator of FIG. 31A.
Figure 31C:
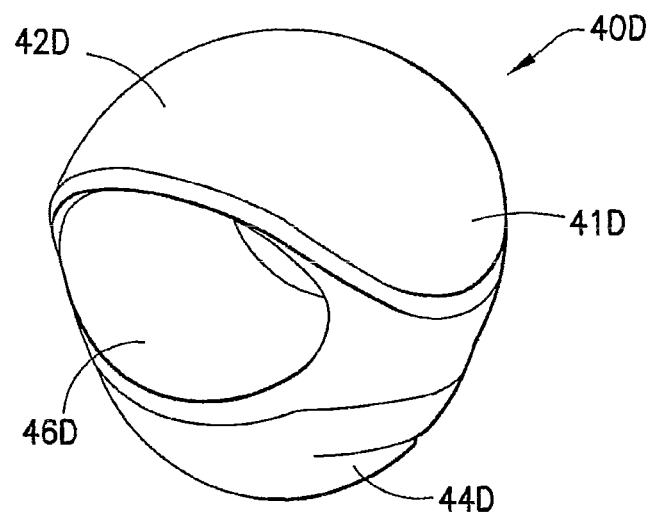
FIG. 31C is a perspective view of a mechanical separator in accordance with an embodiment of the present invention.

As shown in FIGS. 31A-31B, the mechanical separator 140A includes a separator body 141A having a float 142A and a ballast 144A with a through-hole 146A defined within the float 142A, as discussed above. In this configuration, the float 142A may include a partially scalloped region 150A for providing a surface to improve surface shedding of debris during use. As discussed herein, when the separator 140A is submerged within a fluid sample, such as blood, certain blood constituents, such as fibrin or cells, may adhere to or become otherwise trapped on the upper surface of the float 142A. In accordance with the present embodiment, the float 142A may include a scalloped region 150A for increasing the surface shedding. In another embodiment, the float 142A may include opposing scalloped regions 150A, such as shown in FIG. 31B. The scalloped region 150A may include any curved shape suitable to increase the surface shedding of the float, such as elliptical, oval, curved, and the like.

In this configuration, the separator body 141A may also include the first extended tab 152A and the second extended tab 154A having enlarged fillets 180A positioned at the edges of the first and second extended tabs 152A, 154A adjacent the through-hole 146A to assist in the formation of a barrier against a portion of the tube wall in the sealing position, as described herein. The enlarged fillets 180A may include a region of the first and second extended tabs 152A, 154A having an increased thickness and/or diameter, such as a widened taper adjacent the ends of the first and second extended tabs 152A, 154A and extending along at least a portion of the through-hole 146A. In one configuration, the enlarged fillets 180A may facilitate shedding of cells around the mechanical separator body 141A during application of applied rotational force, as described herein.

Figure 68:
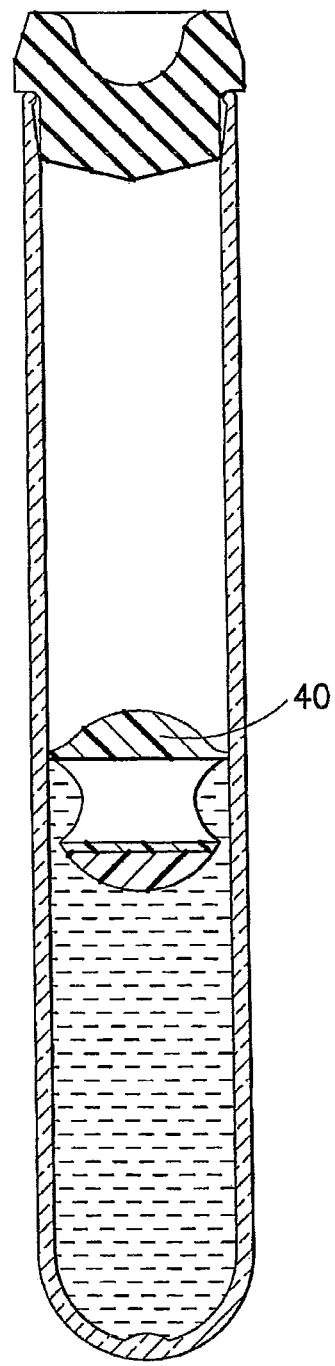
FIG. 68 is a cross-sectional side view of the separation assembly of FIG. 67 having a mechanical separator in a sealing position illustrating the carrier in the fully dissolved state after application of rotational force in accordance with an embodiment of the present invention.

In accordance with a further embodiment of the present application, as shown in FIGS. 31C-31I, the mechanical separator 40D includes a separator body 41D having a float 42D and a ballast 44D with a through-hole 46D defined within the float 42D, as discussed above. In this configuration, the separator body 41D may have a substantially egg-shaped outer perimeter for improving the barrier seal between the mechanical separator 40D and the sidewall of the collection container in the sealing position, such as is shown in FIGS. 29 and 68.

Figure 31D:
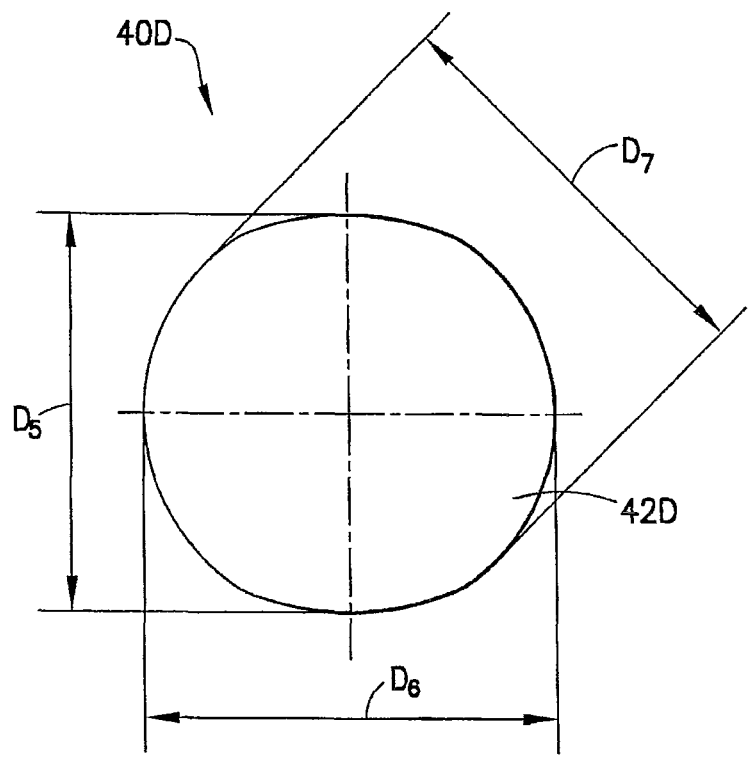
FIG. 31D is a top view of the mechanical separator of FIG. 31C.
Figure 31E:
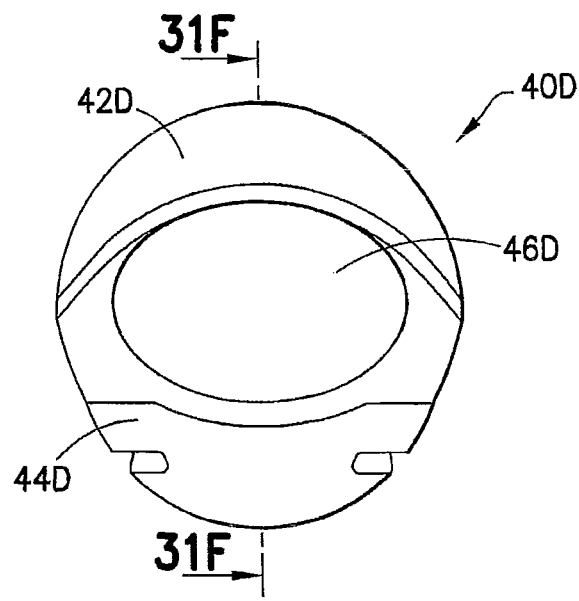
FIG. 31E is a front view of the mechanical separator of FIG. 31C.
Figure 31F:
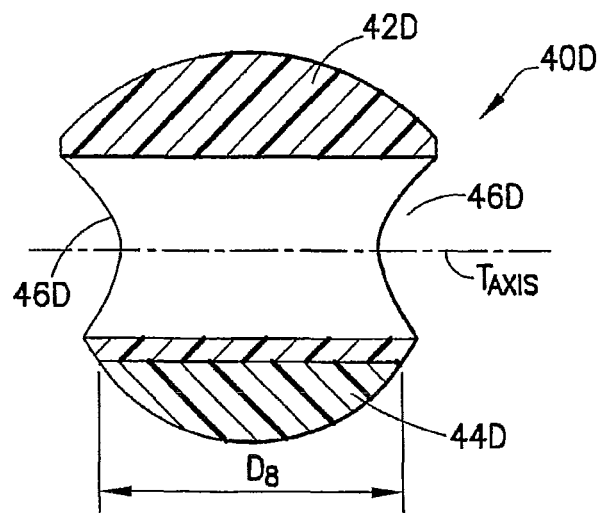
FIG. 31F is a cross-sectional view of the mechanical separator of FIG. 31C taken along line 31F-31F of FIG. 31E.
Figure 31G:
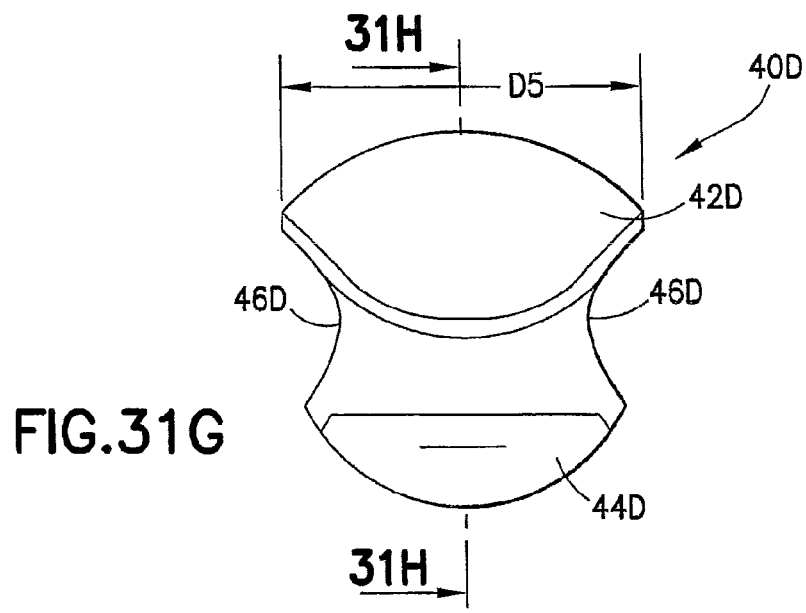
FIG. 31G is a side view of the mechanical separator of FIG. 31C.
Figure 31H:
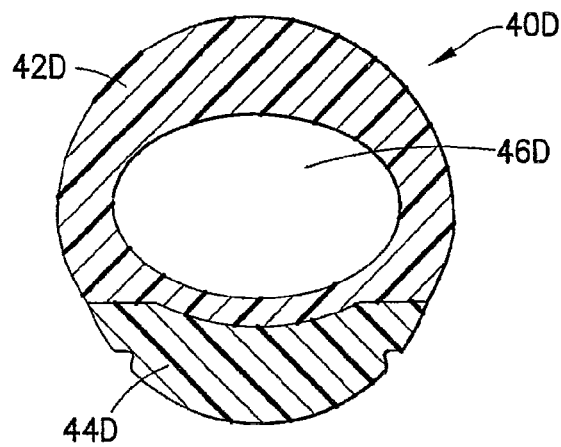
FIG. 31H is a cross-sectional view of the mechanical separator of FIG. 31C taken along line 31H-31H of FIG. 31G.
Figure 31I:
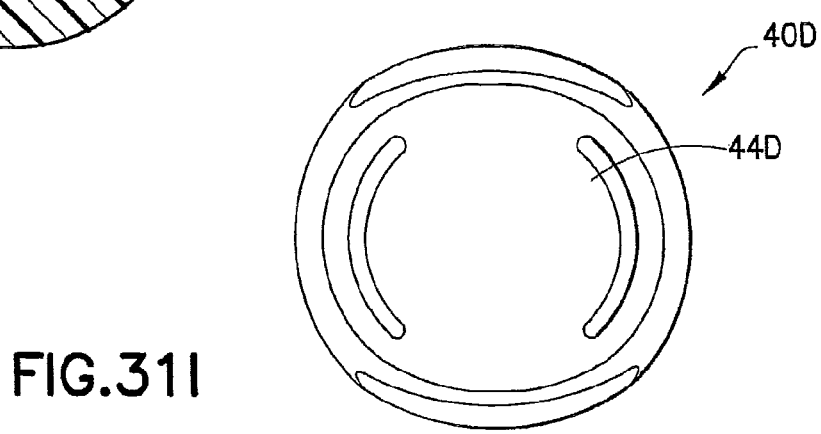
FIG. 31I is a bottom view of the mechanical separator of FIG. 31C.
Figure 32:
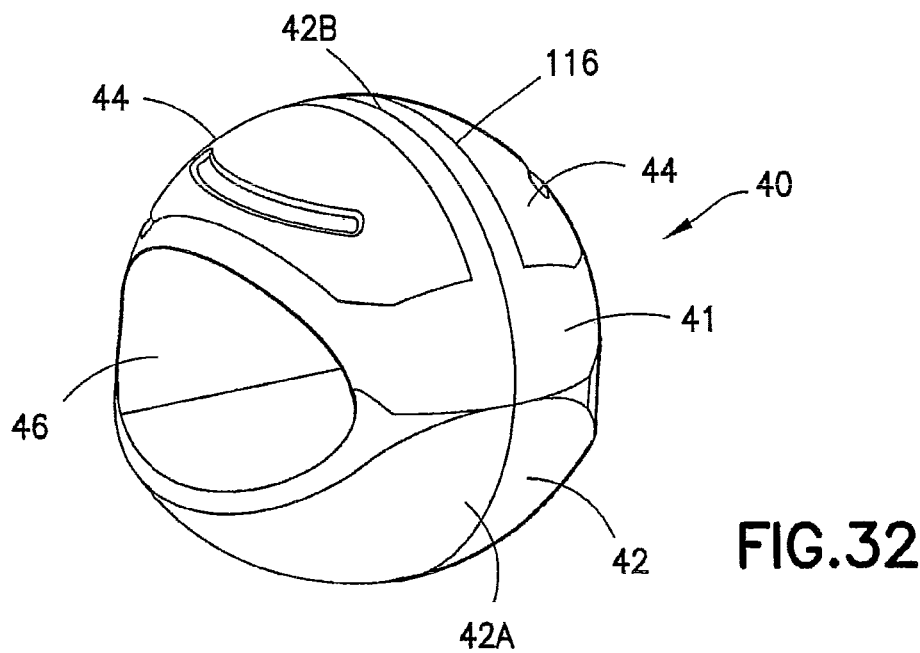
FIG. 32 is a perspective view of a mechanical separator having an initial engagement band in accordance with an embodiment of the present invention.

In this configuration, the diameter $D_5$ of the separator body 41D, specifically the float 42D as shown in FIGS. 31D and 31G, taken across the float 42D in the direction along the through-axis $T_{axis}$ of the through hole 46D, as shown in FIG. 31F, may be less than the diameter $D_6$ of the separator body 41D, specifically the float 42D as shown in FIG. 31D, taken across the float 42D in the direction perpendicular to the through-axis $T_{axis}$ of the through hole 46D, as shown in FIG. 31F. In this configuration, the diameter $D_7$ of the separator body 41D, specifically the float 42D as shown in FIG. 31D, taken across the float 42D at an angle of 45° to the through-axis $T_{axis}$ may be larger than the through-hole 46D, or may be greater than the diameters $D_5$ and $D_6$ of the separator body 41D. Also in this configuration, the diameter $D_8$ of the ballast 44D taken across the ballast 44D along the through-axis $T_{axis}$ of the through-hole 46D, as shown in FIG. 31F, may be less than any of the diameters $D_5$, $D_6$, or $D_7$ of the separator body 41D.

Figure 33:
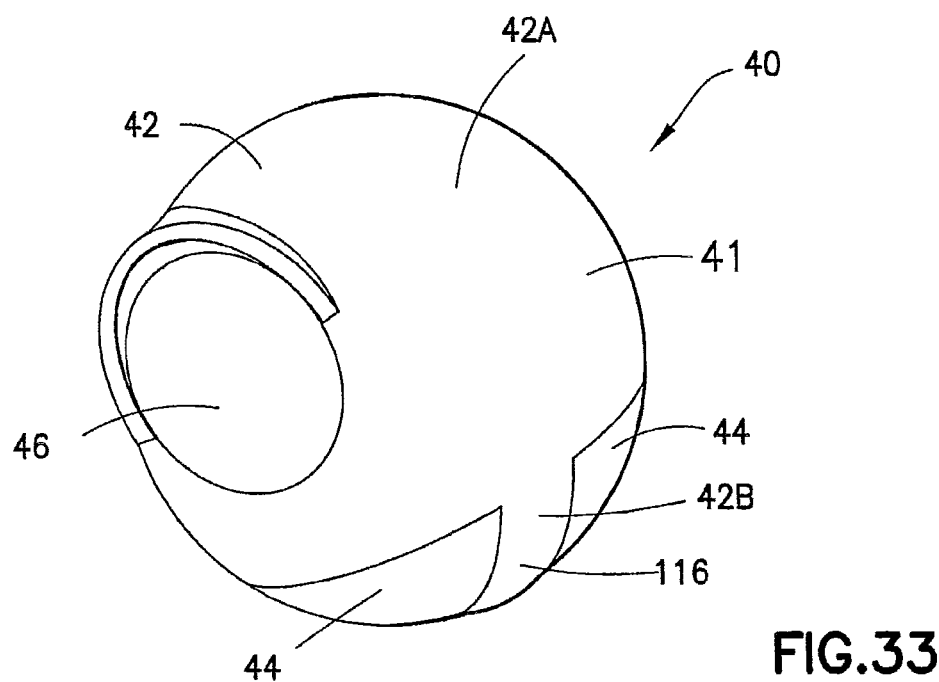
FIG. 33 is an alternative perspective view of a mechanical separator having an initial engagement band as shown in FIG. 32.
Figure 34:
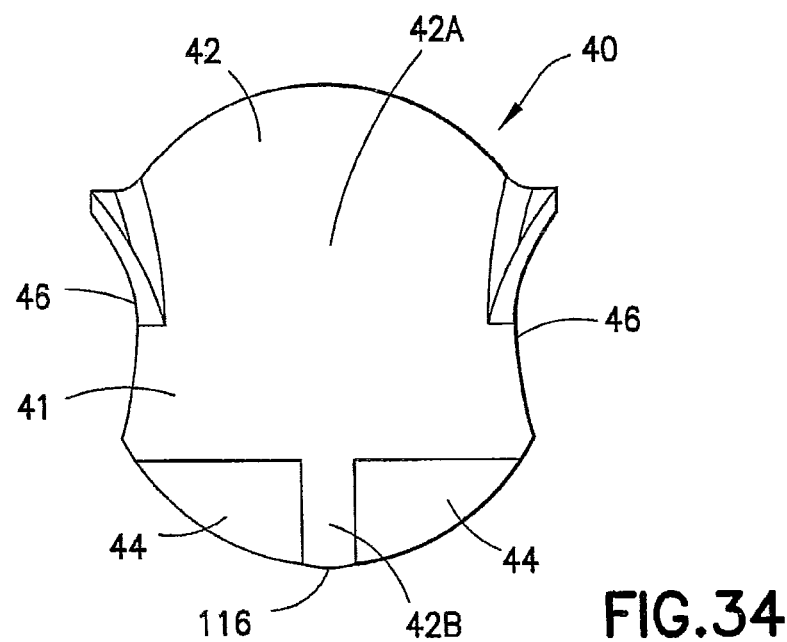
FIG. 34 is a side view of the mechanical separator having an initial engagement band as shown in FIG. 33.

The provision of a float 42D having an increased diameter with respect to the ballast 44D may provide for a mechanical separator 40D having an increased volume of lower density material, such as TPE, for displacing against a sealing surface as described herein. This embodiment may also include an extended tab band, as discussed below with respect to FIGS. 35A-35E, and/or an initial engagement band, as discussed below with respect to FIGS. 33-35.

Referring to FIGS. 32-35, in a further configuration, the mechanical separator 40 may further include an initial engagement band 116 circumferentially disposed about the separator body 41. In a further configuration, the initial engagement band 116 may be disposed about the separator body 41 in a direction substantially perpendicular to the through-hole 46. The initial engagement band 116 may be continuously provided about the separator body 41, or may optionally be provided in segments about the separator body 41. In yet a further configuration, the float 42 and the initial engagement band 116 may be formed from the same material, such as TPE. The initial engagement band 116 may be provided such that a first portion 42A of the float 42 forms the initial engagement band 116, and a second portion 42B substantially bisects the ballast 44.

Figure 35:
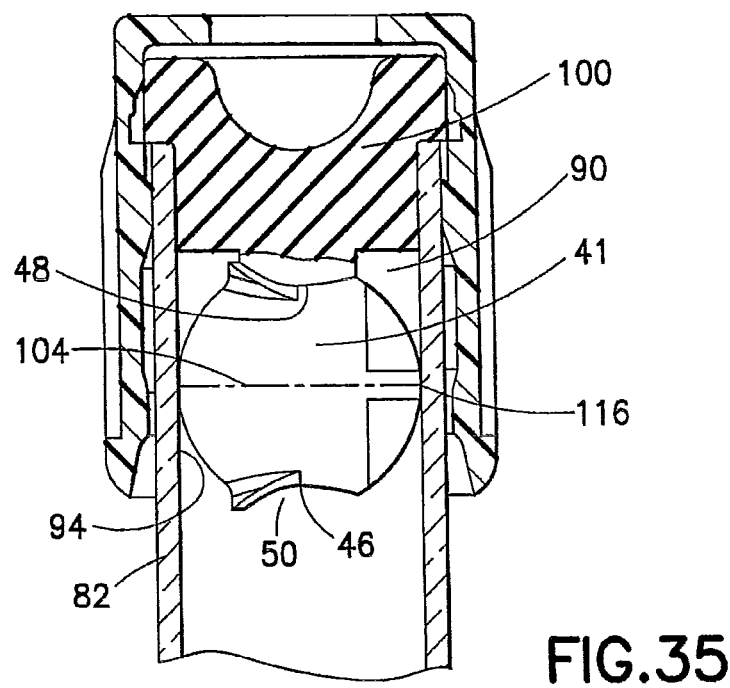
FIG. 35 is a partial cross-sectional side view of the mechanical separator having an initial engagement band of FIG. 33 engaged with a portion of the sidewall of a collection container and closure in accordance with an embodiment of the present invention.
Figure 35A:
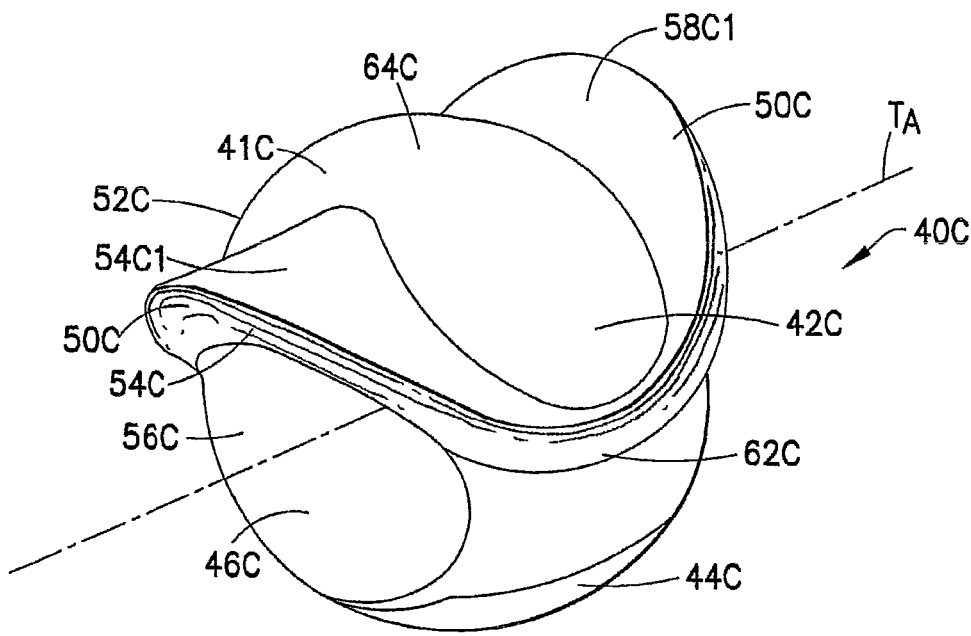
FIG. 35A is a perspective view of a mechanical separator having an extended tab band in accordance with an embodiment of the present invention.

As shown specifically in FIG. 35, the initial engagement band 116 provides an interference engagement between the separator body 41 and the inner surface 94 of the collection container 82. In this configuration, a first sealing perimeter 104 about the separator body 41 is inline with the initial engagement band 116. This first sealing perimeter 104 assists in maintaining the separator body 41 in proper alignment with the open top end 90 of the collection container 82, such that fluid entering the collection container 82 from a cannula (not shown) disposed through the pierceable septum 100 will pass through the first opening 48 of the separator body 41, through the through-hole 46, and out the second opening 50.

In accordance with yet another embodiment of the present invention, as shown in FIGS. 35A-35E, the mechanical separator 40C includes a separator body 41C having a float 42C and a ballast 44C. The separator body 41C includes a through-hole 46C defined therein, such as defined entirely within the float 42C. In this configuration, the float 42C may include an extended tab band 50C disposed about an outer surface 52C of the float 42C. In one embodiment, the extended tab band 50C may include a first extended portion 54C adjacent a first opening 56C of the through-hole 46C, and a second extended portion 58C adjacent the second opening 60C of the through-hole 46C. In this configuration, the first extended portion 54C and the second extended portion 58C may be provided substantially adjacent to at least a portion of the first opening 56C and the second opening 60C, respectively. The first extended portion 54C and the second extended portion 58C may each have a generally concave downwardly-directed orientation.

The first extended portion 54C and the second extended portion 58C may also be provided substantially about a portion of the through-hole 46C, such as in an outwardly-extending arcuate shape about an upper portion of the through-hole 46C. A portion of the first extended portion 54C and a portion of the second extended portion 58C may extend outwardly from the float 42C in a direction substantially parallel to the through axis $T_A$ of the separator body 41C, such that the first extended portion 54C and the second extended portion 58C may have substantially the same shape and curvature.

The extended tab band 50C may also include joining portions 62C disposed between and connecting the first extended portion 54C and the second extended portion 58C on both sides of the separator body 41C. The joining portions 62C may each have a generally concave upwardly-directed orientation. In one embodiment, the joining portions 62C, the first extended portion 54C, and the second extended portion 58C are continuous therewith, forming a generally "rope-like" appearance wrapped around a portion of the float 42C. In a further embodiment, the joining portions 62C, the first extended portion 54C, and the second extended portion 58C form a continuous sine function shape about a portion of the outer surface 52C of the float 42C. In another embodiment, the extended tab band 50C may be co-formed with the float 42C, forming a portion of the float 42C itself. In an alternative embodiment, the extended tab band 50C may be separately formed and subsequently joined with the float 42C. In certain configurations, both the float 42C and the extended tab band 50C are made of a lower density material, such as TPE, and the ballast 44C may be formed of a higher density material, such as PET.

Figure 35B:
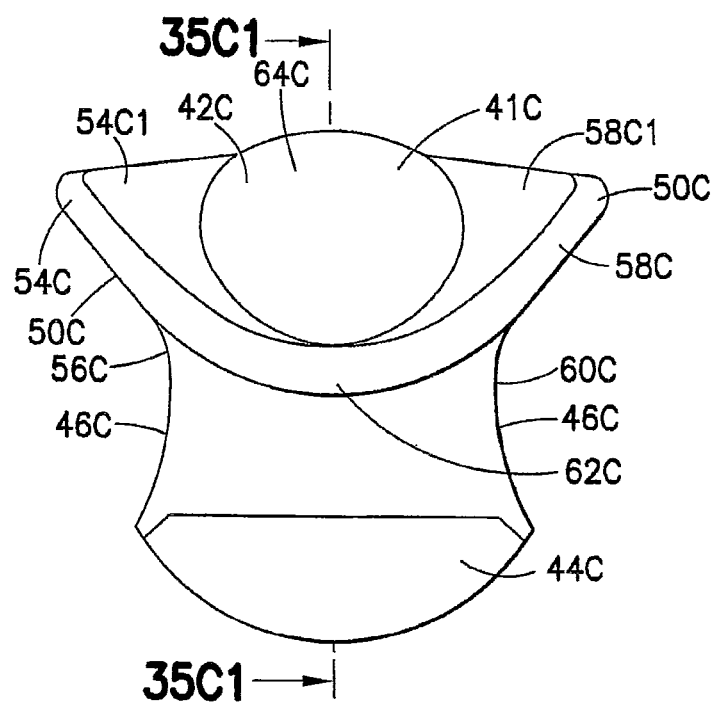
FIG. 35B is a left side view of the mechanical separator of FIG. 35A.
Figure 35C:
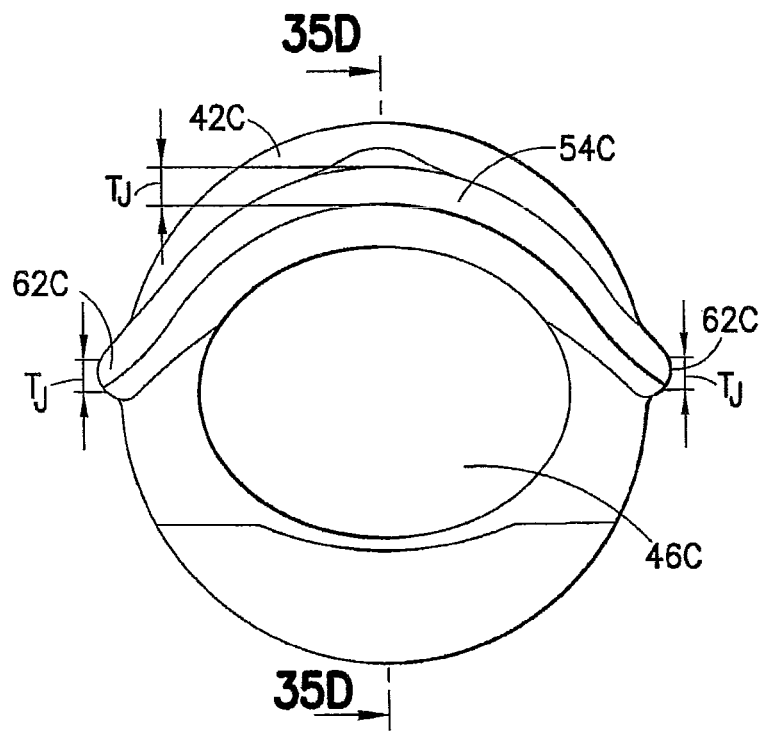
FIG. 35C is a front view of the mechanical separator of FIG. 35A.
Figure 35D:
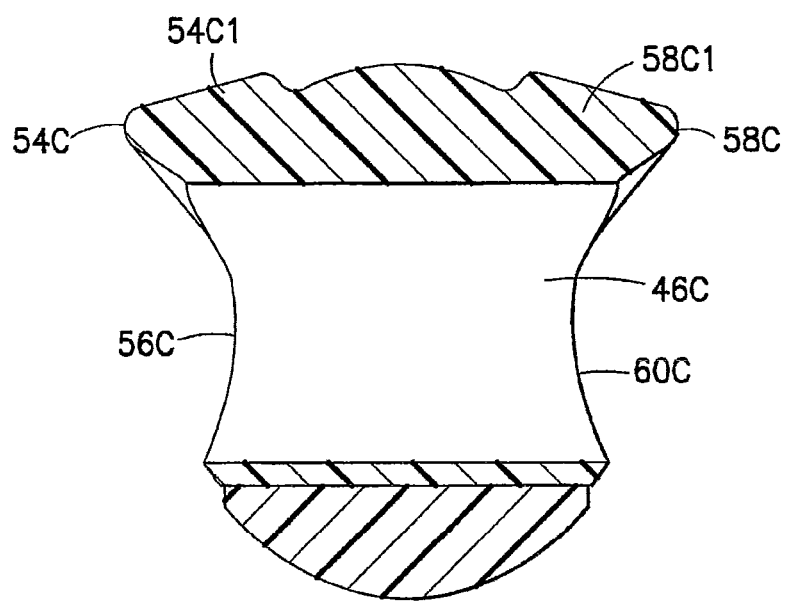
FIG. 35D is a cross-sectional view of the mechanical separator of FIG. 35A taken along line 35D-35D of FIG. 35C.

In one embodiment, shown specifically in FIGS. 35C and 35C1, the joining portions 62C may each have approximately the same thickness $T_J$. In another embodiment, the first extended portion 54C and the second extended portion 58C may also have approximately the same thickness $T_J$. The cross-section of the extended tab band 50C may have any suitable sealing shape such as rounded, squared, ribbed, or the like. It is also contemplated herein, that multiple extended tab bands 50C may be disposed about the outer surface 52C of the float 42C. Referring to FIGS. 35B and 35D, the first extended portion 54C and the second extended portion 58C may include a thickened shelf region, 54C1 and 58C1, respectively, defining a generally spline or saddle shape with the upper portion 64C of the float 42C. The upper portion 64C of the float 42C and the extended tab band 50C may be particularly configured to maximize the surface shedding of debris during use. As discussed herein, when the separator 40C is submerged within a fluid sample, such as blood, certain blood constituents, such as fibrin or cells, may adhere to or become otherwise trapped on the upper surface of the float 42C. The specific shaping of the extended tab band 50C is intended to minimize the trapping of debris during use.

Figure 35E:
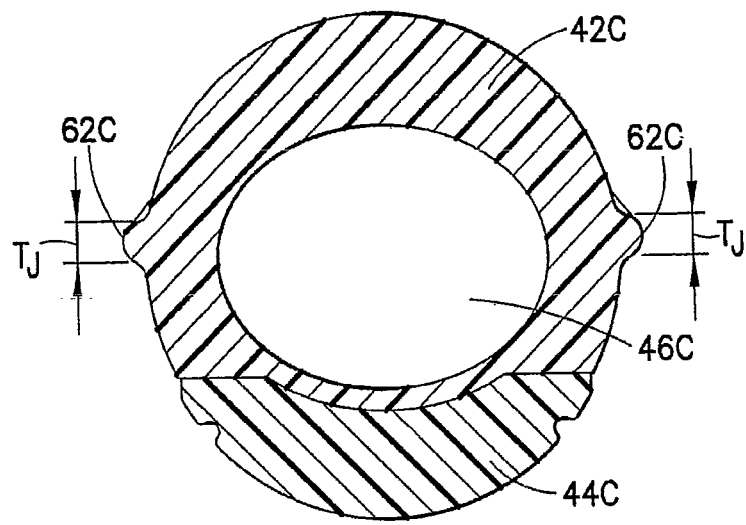
FIG. 35E is a perspective view of a mechanical separator having an alternative extended tab band in accordance with an embodiment of the present invention.
Figure 35E:
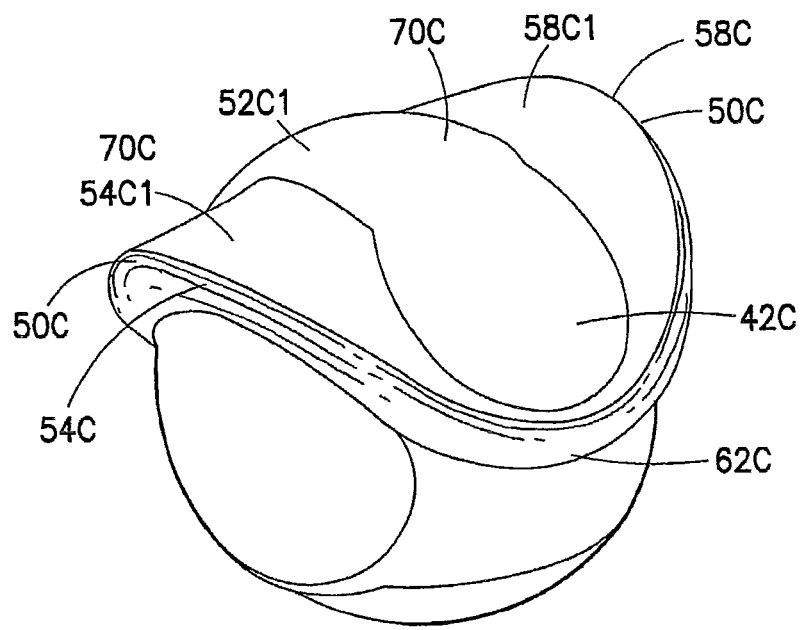

In yet another embodiment, as shown in FIG. 35E, the extended tab band 50C may include a first extended portion 54C, a second extended portion 58C, and joining portions 62C connecting the first extended portion 54C and the second extended portion 58C on both sides of the float 42C so as to form a continuous structure about the outer surface 52C of the float 42C. In this configuration, the thickened shelf region 54C1 of the first extended portion 54C and the thickened shelf region 58C1 of the second extended portion 58C have a truncated profile 54C2 and 58C2, respectively, to improve surface shedding of debris during use and to provide additional structural support to the first extended portion 54C and the second extended portion 58C during sealing with a collection container (not shown) in the sealing position.

When the mechanical separator 40C of the present embodiment is in use, the extended tab band 50C provides a robust sealing surface against a portion of the collection container wall (not shown), similar to the seal defined by the first extended tab and the second extended tab described above with reference to FIGS. 1-8. In certain embodiments, the extended tab band 50C may provide additional sealing and minimize leakage between the mechanical separator 40C and the collection container. In addition, in the configurations in which the float 42C is formed of TPE, the extended tab band 50C provides a mechanism for enhanced sealing in that TPE does not appreciably deform under conventional applied rotational forces but rather displaces to another location. The location of the arcuate extended tab band 50C about an outer surface 52C of the float 42C allows for the TPE to displace uniformly against a sidewall of the collection container in a sealing position, as described herein. As the extended tab band 50C may be provided in an alternating concave upwardly-directed and concave downwardly-directed orientation, the sealing surface of the mechanical separator 40C may be located at various heights about the outer surface 52C of the float 42C corresponding to the location of the extended tab band 50C.

In an additional configuration, it is intended herein that the mechanical separator 40C having an extended tab band 50C may be suitable for use in collection containers having a tilted orientation due to the enhanced sealing between the extended tab band 50C and the collection container (as described above) in the sealing position. It is also intended herein that the mechanical separator 40C may include an initial engagement band 116, as similarly described with reference to FIG. 35 above.

Figure 35F:
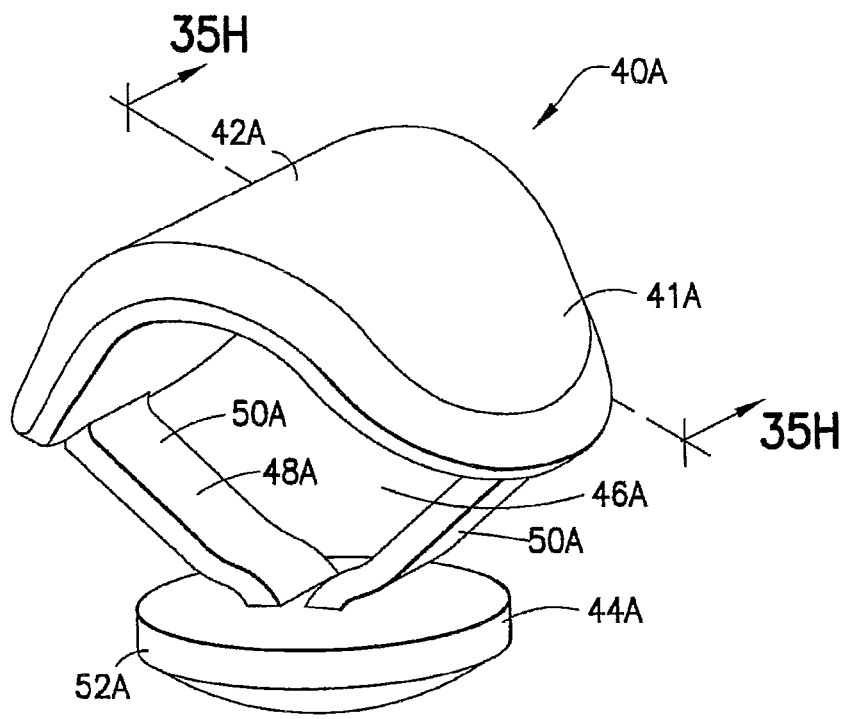
FIG. 35F is a perspective view of a mechanical separator having a joining structure in accordance with an embodiment of the present invention.
Figure 35G:
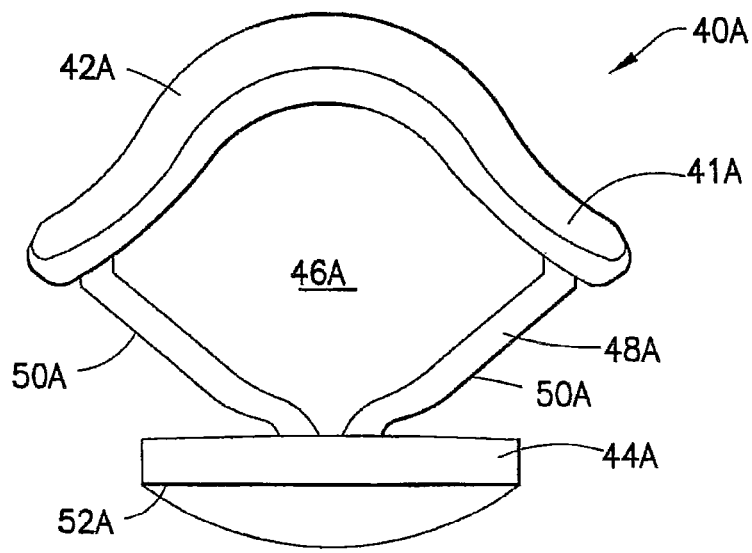
FIG. 35G is a front view of the mechanical separator of FIG. 35F.

In accordance with yet another embodiment of the present invention, as shown in FIGS. 35F-35G, the mechanical separator 40A includes a separator body 41A having a float 42A and a ballast 44A. The separator body 41A includes a through-hole 46A defined therein. In this configuration, the ballast 44A may include a base portion 52A and a joining structure 48A, such as a plurality of arms 50A for engaging a portion of the float 42A. The ballast 44A, specifically the joining structure 48A, may be provided in permanent engagement with a portion of the float 42A, such as by co-molding, two-shot molding, welding, or other adhesive joining means. In one configuration, the float 42A may be formed of a lower density material, such as TPE, and the ballast 44A may be formed of a higher density material, such as PET. In a further configuration, the mechanical separator 40A may be dimensioned such that the overall density of the separator body 41A is between the density of higher and lower density constituents of a blood sample, such as serum and red blood cells. In yet a further embodiment, the overall density of the separator body 41A is 1.45 g/cm$^3$.

Figure 35H:
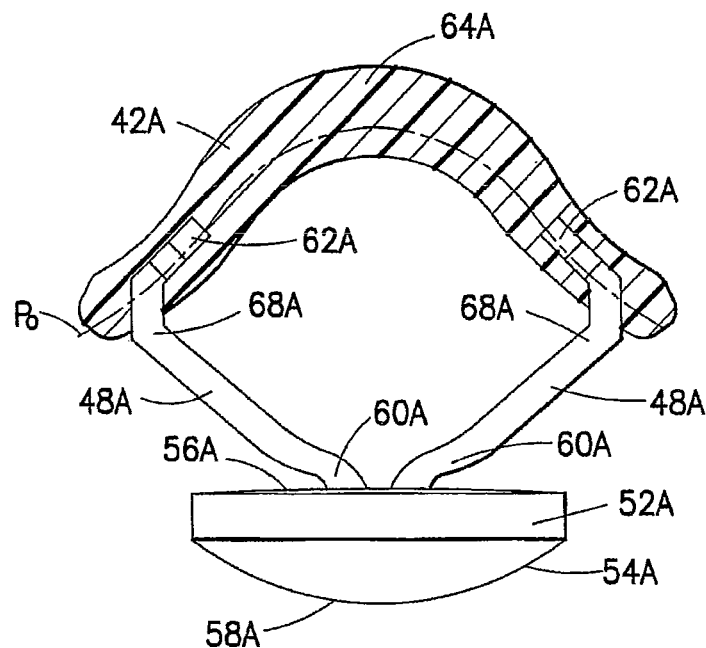
FIG. 35H is a cross-sectional view of the mechanical separator of FIG. 35G taken along line 35H-35H of FIG. 35F.

As shown in FIG. 35H, the ballast 44A may include a base portion 52A having a contact surface 54A and a joining surface 56A. In one configuration, the contact surface 54A may include an at least partially curved surface 58A corresponding to an inner curvature of a collection container (not shown). The joining surface 56A may include an attachment between the base portion 52A and the joining structure 48A. In one configuration, the joining surface 56A and the joining structure 48A are co-formed. In another configuration, the joining surface 56A and the joining structure 48A are separately formed and subsequently provided in permanent attachment through mechanical or adhesive locking means.

Figure 35I:
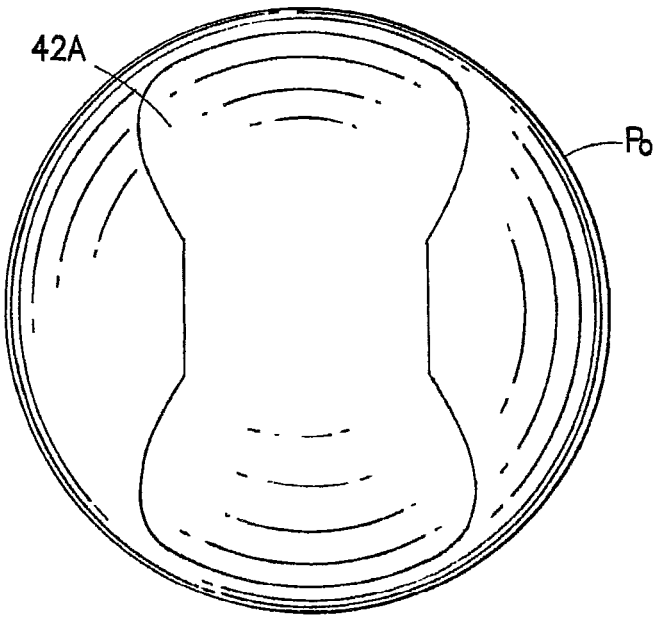
FIG. 35I is a top view of the mechanical separator of FIG. 35F.

The joining structure 48A may include a first end 60A for engaging the base portion 52A of the ballast 44A and a second end 62A for engaging a portion of the float 42A. The top view of the float 42A may have a substantially circular outer perimeter $P_O$, as shown in FIG. 35I, and the float 42A may have a substantially curved cross-sectional side view, such as a substantially concave down cross-section as shown in FIG. 35H. In a further embodiment, the float 42A may have a substantially concave down cross-section adjacent an apex 64A of the float 42A, and a slight concave upward curvature adjacent the perimeter $P_O$ of the float 42A, such as at a location at which the second end 62A of the joining structure 48A is attached to the float 42A. In one configuration, the second end 62A of the joining structure 48A is molded first and the float 42A is subsequently molded onto the second end 62A of the joining structure 48A to form a bond therewith. In another embodiment, the second end 62A of the joining structure 48A is inserted within, or provided adjacent to, a portion of the float 42A and subsequently bonded or otherwise adhered thereto.

In one configuration, the joining structure 48A may provide flexure between the float 42A and the base portion 52A. The flexure may be provided by at least one of the attachment between the first end 60A of the joining structure 48A and the base portion 52A, the attachment between the second end 62A of the joining structure 48A and the float 42A, and the pivot points 68A of the joining structure 48A.

Figures 35J, 35K:
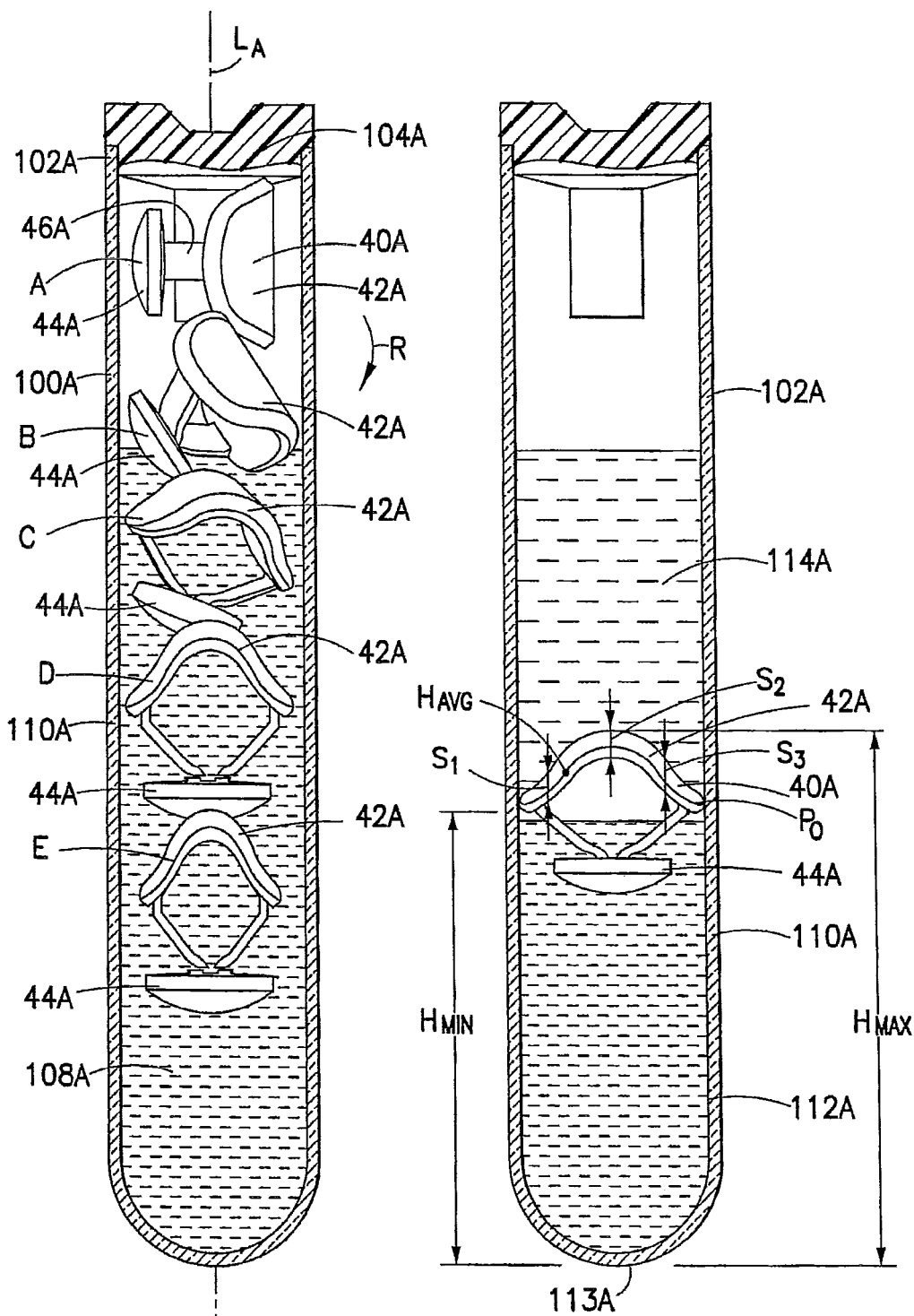
FIG. 35J is a schematic front view of the mechanical separator of FIG. 35F disposed within a collection container in various states of descent within the collection container in accordance with an embodiment of the present invention.
FIG. 35K is a schematic front view of the mechanical separator of FIG. 35J in a sealing position in accordance with an embodiment of the present invention.

Referring to FIG. 35J, the mechanical separator 40A may be provided within a collection container 100A, such as adjacent an upper end 102A of the collection container 100A in an initial position. The mechanical separator 40A may be provided in engagement with a portion of a stopper 104A, such that a portion of the stopper 104A extends through the through-hole 46A of the mechanical separator 40A, as described elsewhere herein. In accordance with another embodiment of the present invention, the mechanical separator 40A may be provided such that a portion of the float 42A and a portion of the base portion 52A of the ballast 44A engage an inner surface of the collection container 100A to restrain the mechanical separator 40A within the upper end 102A of the collection container 100A such that the through-hole 46A of the mechanical separator 40A is aligned with the longitudinal axis $L_A$ of the collection container 100A.

Referring again to FIG. 35J, a fluid specimen 108A, such as blood, is introduced into the collection container 100A, such as through the stopper 104A and aligned with through-hole 46A of the mechanical separator 40A when the mechanical separator 40A is oriented in the initial position as shown by reference character A. As rotational force is applied, the float 42A flexes and initiates a flexure between the float 42A and the ballast 44A, as described above. The resulting flexure deforms the through-hole 46A and the mechanical separator 40A disengages from the stopper 104A and begins to rotate in the direction shown by arrow R, as shown by reference character B.

As the mechanical separator 40A becomes submerged within the fluid specimen 108A, the float 42A begins to orient in an upward direction and the ballast 44A simultaneously begins to orient in a downwards direction, as shown by reference character C. During the continued application of rotational force, the ballast 44A pulls in a downwards direction and the float 42A flexes away from the sidewall 110A of the collection container, as shown by reference character D. Subsequently, as shown by reference character E, the float 42A is deformed to allow for the passage of higher and lower density phase constituents between the float 42A and the sidewall 110A of the collection container 100A. This allows for separation of the higher and lower density phase constituents within the fluid sample 108A, as well as for the separation of higher and lower density phase constituents within the fluid sample 108A present within the through-hole 46A of the mechanical separator 40A.

Referring to FIG. 35K, once the application of rotational force has ceased, the mechanical separator 40A becomes oriented between the separated higher density phase 112A and the separated lower density phase 114A in a sealing position. At the same time, the flexure between the float 42A and the ballast 44A ceases, causing the float 42A to return to its initial position, as shown in FIG. 35I, thereby forming a seal between the outer perimeter $P_O$ and the interior circumference of the sidewall 110A of the collection container 100A. The float 42A has an outer perimeter $P_O$ having an outer circumference that is at least slightly larger than the interior circumference of the sidewall 110A of the collection container 100A, thereby forming a robust seal therebetween.

Referring yet again to FIG. 35K, once the mechanical separator 40A has been transitioned to the sealing position, a sealing perimeter is established along the outer perimeter $P_O$ between at least a portion of the interior circumference of the sidewall 110A and the mechanical separator 40A. As shown in FIG. 35K, the sealing perimeter along the outer perimeter $P_O$ has a varying position about the interior circumference of the sidewall 110A as measured from the closed bottom end 113A of the collection container 100A. In one configuration, the sealing perimeter along the outer perimeter $P_O$ includes various sealing heights at each localized sealing location, $S_1$, $S_2$, $S_3$, etc. corresponding to the overall height of the seal between the mechanical separator 40A, specifically, the float 42A, and the sidewall 110A. The sealing perimeter accordingly has a height which varies slightly at each localized sealing location $S_1$, $S_2$, $S_3$, etc. The sealing perimeter also defines an average sealing height $H_{Avg}$ which corresponds to the average height of each localized sealing location $S_1$, $S_2$, $S_3$, etc., i.e., $H_{Avg}$=Avg [$S_1$, $S_2$, $S_3$, etc.]. The mechanical separator 40A also has a maximum height $H_{Max}$ and a minimum height $H_{Min}$ within the collection container. The maximum height $H_{Max}$ corresponds to the distance between the highest seal point along the outer perimeter $P_O$ and the closed bottom end 113A of the collection container 100A. The minimum height $H_{Min}$ corresponds to the lowest seal point along the outer perimeter $P_O$ and the closed bottom end 113A of the collection container 100A. In accordance with an aspect of the present invention, the average sealing height $H_{Avg}$ is less than the difference between the maximum seal height $H_{Max}$ and the minimum seal height $H_{Min}$, i.e., $H_{Avg} < H_{Max} - H_{Min}$.

Figure 35L:
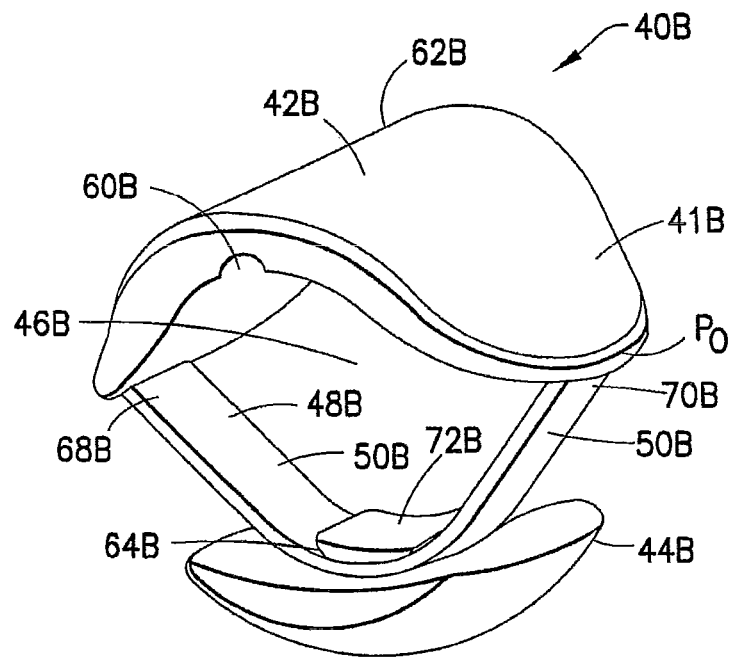
FIG. 35L is a perspective view of a mechanical separator having an alternative joining structure in accordance with an embodiment of the present invention.
Figure 35M:
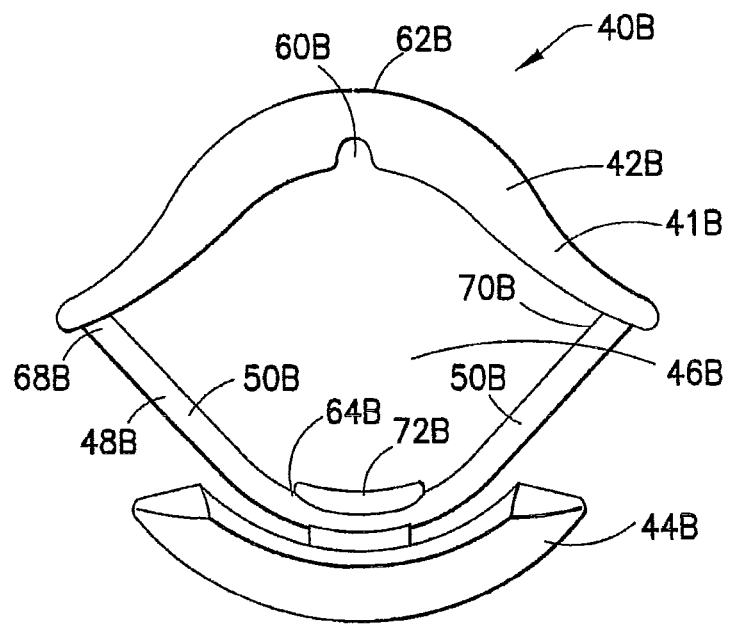
FIG. 35M is a front view of the mechanical separator of FIG. 35L.

In accordance with another embodiment of the present invention, as shown in FIGS. 35L-35M, the mechanical separator 40B includes a separator body 41B having a float 42B and a ballast 44B. The separator body 41B includes a through-hole 46B defined therein. In this configuration, the float 42B may include a joining structure 48B, such as a plurality of arms 50B for engaging a portion of the ballast 44B. As similarly described above, the joining structure 48B may be provided in permanent engagement with a portion of the ballast 44B, such as by co-molding, two-shot molding, welding, or other adhesive joining means. In this configuration, the joining structure 48B may exhibit increased flexibility allowing for easier transition from an initial position to a sealing position, as described herein.

Referring again to FIGS. 35L-35M, in one configuration, the float 42B may include a cut-out 60B within the float 42B. In one embodiment, the cut-out 60B may be positioned at the apex 62B of the float 42B and does not extend into the outer perimeter $P_O$. The cut-out 60B may provide for increased flexibility to allow passage of higher and lower density phase constituents thereby during use, such as shown in FIG. 35J with reference to reference character E. In yet a further configuration, the joining structure 48B may include an opening 64B therein adapted to allow a portion of the ballast 44B to pass therethrough and be secured therein, such as by way of a mechanical interlock. In one embodiment, the joining structure 48B includes a continuous arm 50B connected to the float 42B at a first end 68B and a second end 70B. The joining structure 48B may include an opening 64B having a locking portion 72B of the ballast 44B extending therethrough. In one embodiment, the opening 64B may be disposed within the continuous arm 50B at a location opposed from the apex 62B of the float 42B. In another embodiment, the ballast 44B, such as the locking portion 72B, and the float 42B may be provided in permanent engagement so as to minimize separation of the float 42B and the ballast 44B.

Figure 35N:
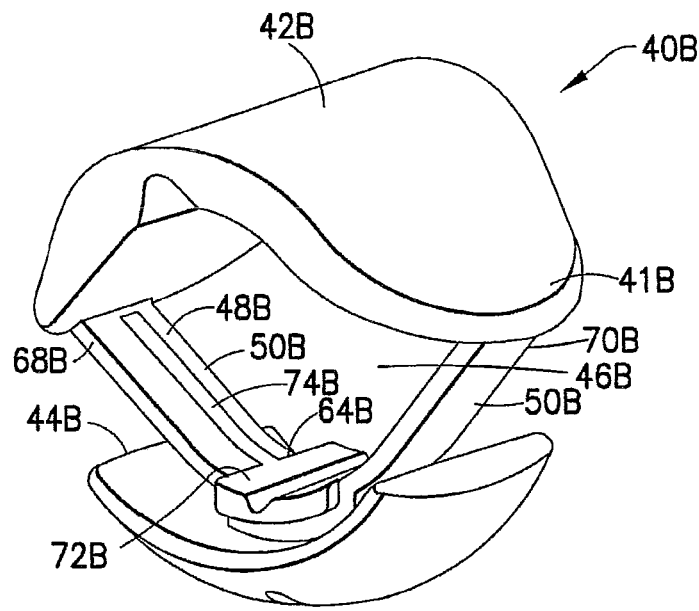
FIG. 35N is a perspective view of a mechanical separator having an alternative joining structure in accordance with an embodiment of the present invention.
Figure 35O:
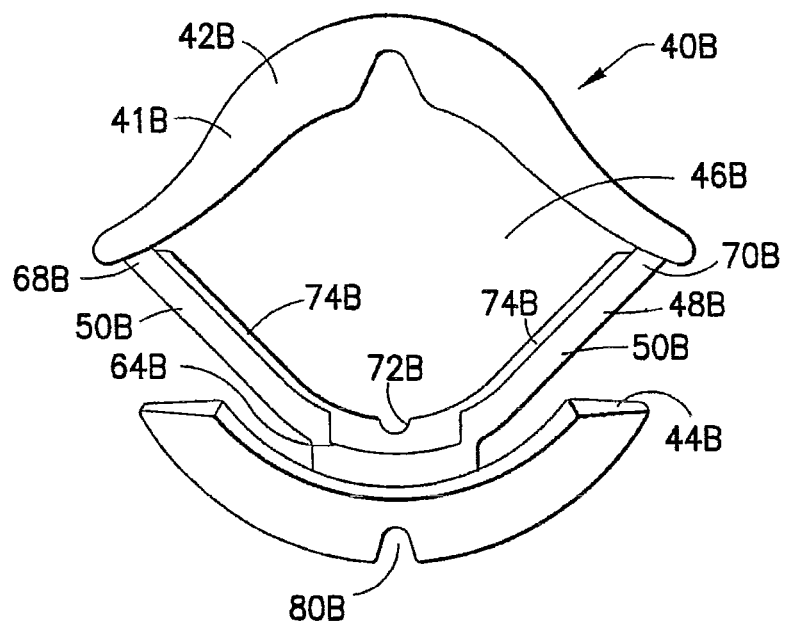
FIG. 35O is a front view of the mechanical separator of FIG. 35N.

Referring to FIGS. 35N-35O, in a further embodiment of the present invention, the mechanical separator 40B includes a separator body 41B having a float 42B and a ballast 44B. The separator body 41B includes a through-hole 46B defined therein. In this configuration, the float 42B may include a joining structure 48B, such as a plurality of arms 50B for engaging a portion of the ballast 44B. As similarly described above, the joining structure 48B may include a continuous arm 50B connected to the float 42B at a first end 68B and a second end 70B. The joining structure 48B may include an opening 64B having a locking portion 72B of the ballast 44B extending therethrough in permanent engagement so as to minimize separation of the float 42B and the ballast 44B. The ballast 44B may also include a support structure 74B adjacent and connected to the joining structure 48B of the float 42B. In one embodiment, the support structure 74B of the ballast 44B may be co-formed or otherwise permanently engaged with the joining structure 48B of the float 42B. In a further embodiment, the joining structure 48B may define a recess adapted to at least partially surround the support structure 74B. In yet a further embodiment, the support structure 74B and the joining structure 48B allow the float 42B and ballast 44B to at least partially flex with respect to each other, as described herein. In certain configurations, a ballast cut-out 80B may be provided within the base portion 52B to lessen shrinkage of the ballast 44B during formation.

Figure 36:
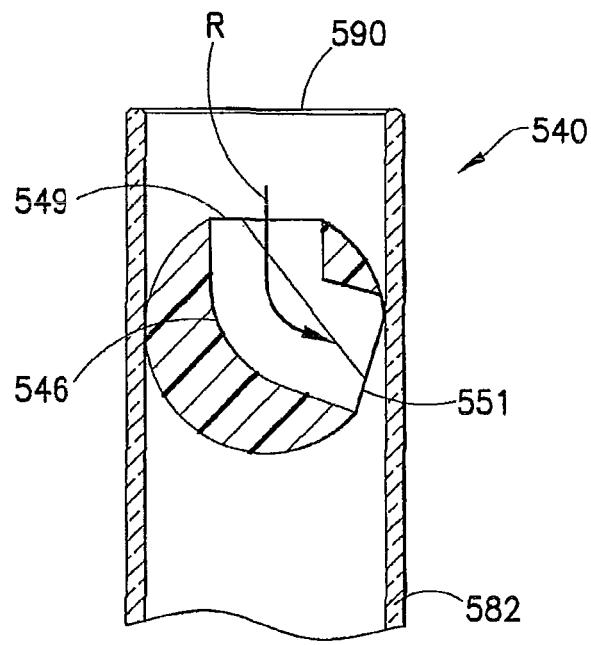
FIG. 36 is a partial cross-sectional side view of a mechanical separator having a circuitous though-hole in an initial position in accordance with an embodiment of the present invention.
Figure 37:
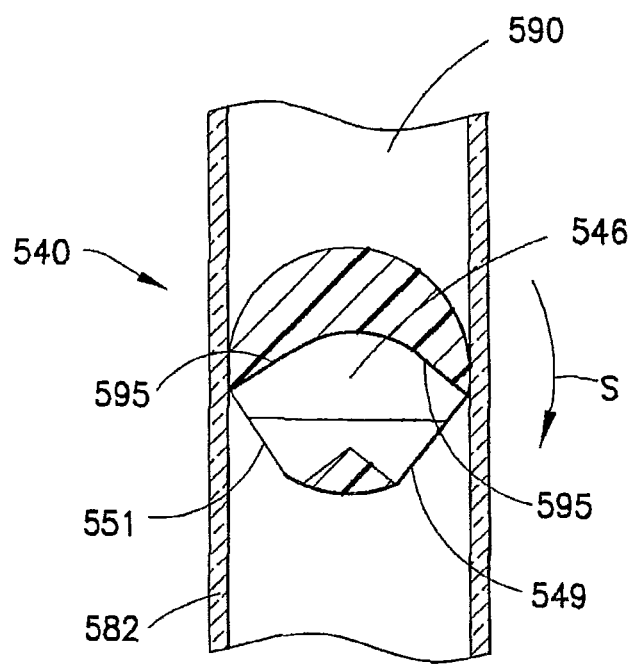
FIG. 37 is a partial cross-sectional side view of the mechanical separator of FIG. 36 having a circuitous though-hole in a sealing position in accordance with an embodiment of the present invention.

Although the through-hole of the mechanical separator of the present invention has been shown herein as a straight bore having a spherical or elliptical cross-section, it is also contemplated herein that the through-hole 546, as shown in FIGS. 36-37, may define a serpentine or circuitous path for receiving liquid therethrough. In this configuration, the mechanical separator 540 includes a through-hole 546 having a first opening 549 and a second opening 551 that are offset with respect to each other. Specifically, the first opening 549 and the second opening 551 may be offset, such as at 60° or 90° angles with respect to each other. As shown in FIG. 36, in the initial position, the first opening 549 is aligned with the top open end 590 of the collection container 582, represented herein in section. Fluid is directed through the through-hole 546 in the direction as shown by directional arrow R. In this configuration, at least one surface of the second opening 551 contacts the sidewall of the collection container 582, while another surface of the second opening 551 remains free within the interior of the collection container 582. Accordingly, a gap is provided between the sidewall of the collection container 582 and the second opening 551 of the through-hole 546 to allow fluid to exit the through-hole 546 and pass into the interior of the collection container 582.

Upon application of rotational force, the mechanical separator 540 will transition from the initial position, as shown in FIG. 36, to a sealing position, as shown in FIG. 37, along directional arrow S, due to the moment of the float and ballast components as described herein. In this configuration, both the first opening 549 and the second opening 551 of the through-hole 546 are provided out of alignment with the top open end 590 of the collection container 582 and are adapted such that fluid is not directed into the through-hole 546. A second sealing perimeter 595 is also established about the mechanical separator 540 such that fluid cannot pass between the mechanical separator 540 and the collection container 582 or through the through-hole 546 of the mechanical separator 540, effectively establishing a barrier.

Figure 38:
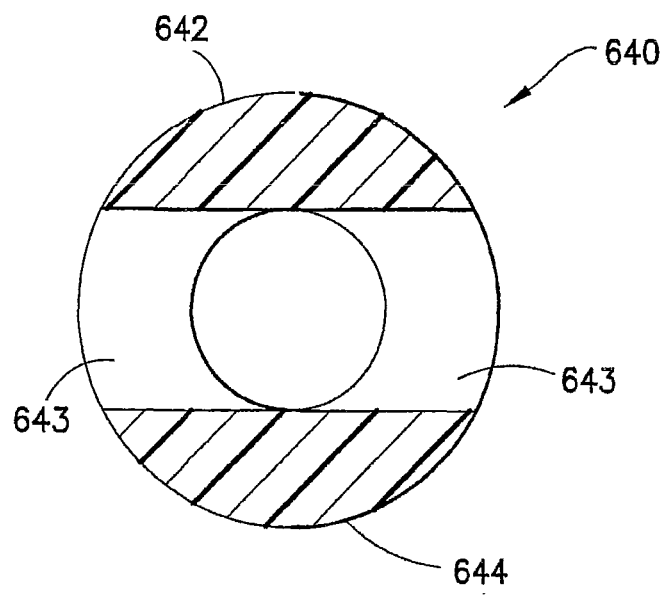
FIG. 38 is a representational cross-section of a mechanical separator having a float and a ballast separated by a thermoplastic elastomer section defining a through-hole in an initial resting position in accordance with yet another embodiment of the present invention.
Figure 39:
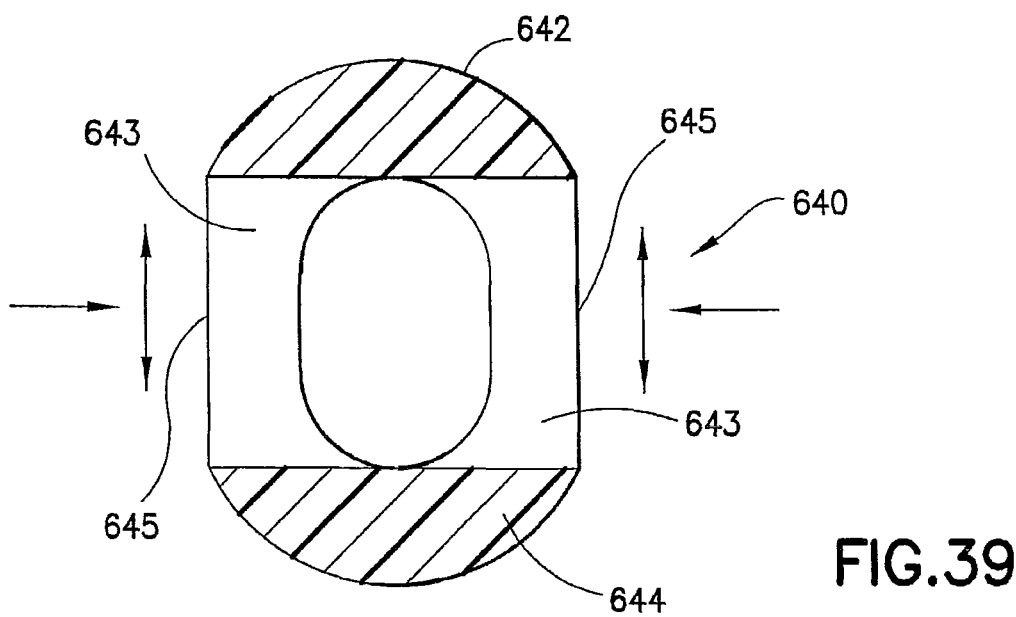
FIG. 39 is a representational cross-section of the mechanical separator of FIG. 38 having a float and a ballast separated by a thermoplastic elastomer section defining a through-hole in an activated position during application of rotational force.

In yet another configuration, as shown in FIGS. 38-39, the elongation of the mechanical separator 640 during application of rotational force is exemplified. In this configuration, the mechanical separator 640 may include a float 642 and a ballast 644 with a third section 643 joining the float 642 and the ballast 644. It is contemplated herein, that in this configuration, both the float 642 and the ballast 644 may be made of a substantially rigid material with the float 642 having a density that is less than the density of the ballast 644. In order to provide for an elongation between these components, the third section 643 formed of a flexible material, such as TPE, may be provided therebetween. During centrifugation, the third section 643 elongates, as shown in FIG. 39, in a manner similarly described with respect to the elongation of the float above. During elongation of the third section 643, higher and lower density phases of a fluid may pass adjacent the fluid passage surfaces 645, as shown in FIG. 39 as in a direction extending into the page.

Figure 40:
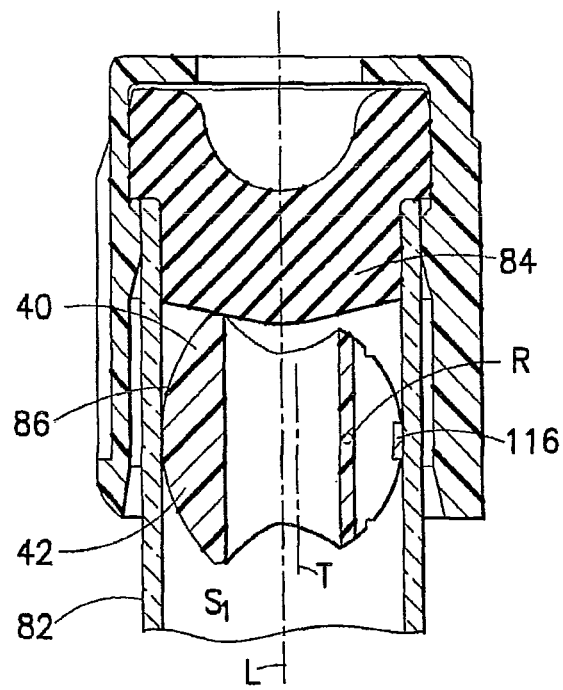
FIG. 40 is a cross-sectional side view of a separation assembly having a mechanical separator engaged with a portion of a collection container having a closure engaged therewith in accordance with an embodiment of the present invention.
Figure 41:
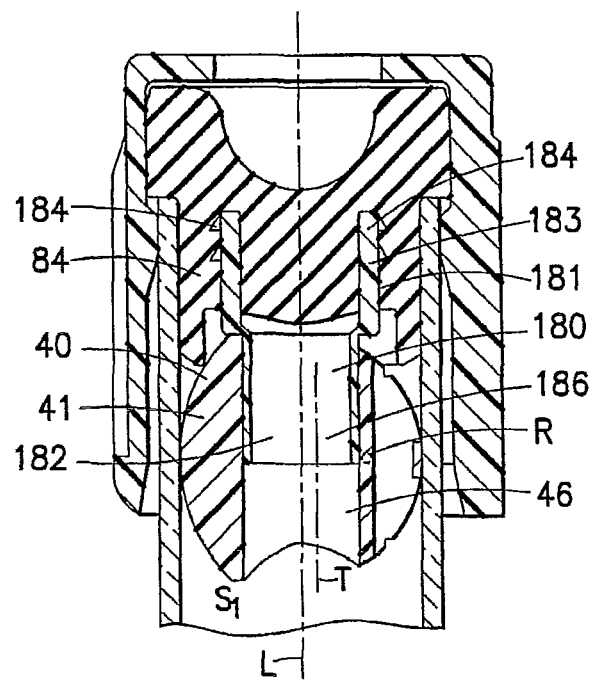
FIG. 41 is a cross-sectional side view of an alternative separation assembly having a mechanical separator engaged with a post which is engaged with an undercut of closure in accordance with an embodiment of the present invention.
Figure 42:
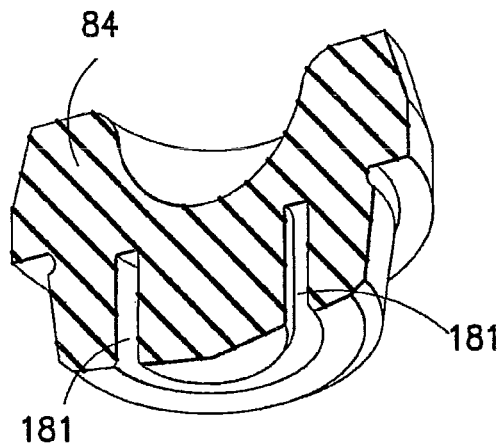
FIG. 42 is a partial cross-sectional perspective of the closure of FIG. 41.
Figure 43:
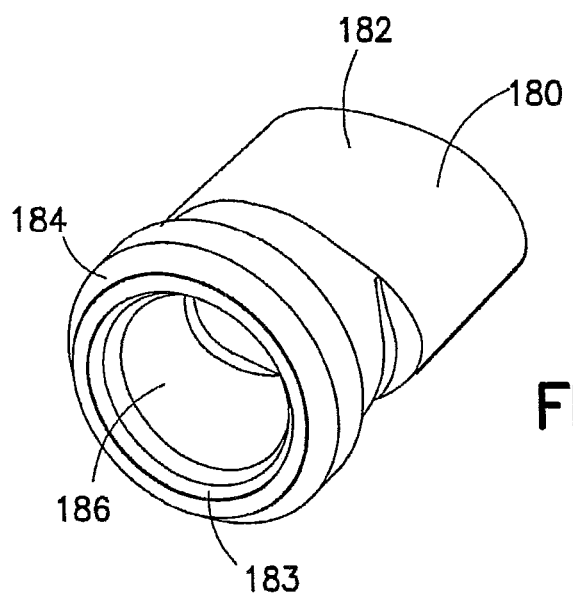
FIG. 43 is a perspective front view of the post of FIG. 41.
Figure 44:
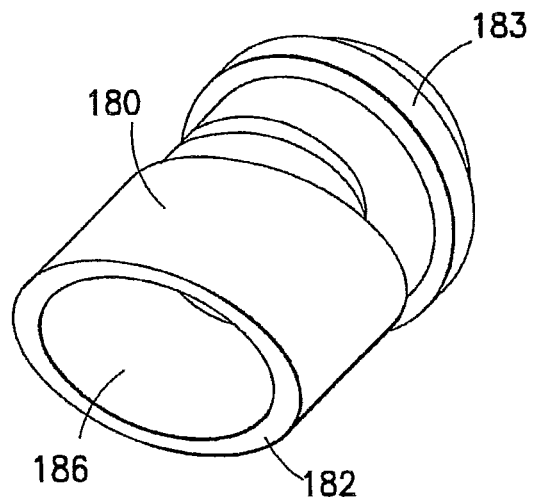
FIG. 44 is a perspective rear view of the post of FIG. 41.

With reference again to FIG. 2 and FIGS. 40 and 41, the separator body 41 may include a center of mass R that is offset from the through-axis T, shown in FIG. 2, of the separator body 41. In this configuration, the mechanical separator 40 is transitionable from a first position (such as shown in FIGS. 40-41) in which the mechanical separator 40 is engaged with a portion of the closure 84 (shown in FIG. 41) or a portion of the sidewall 86 of the collection container 82 (shown in FIG. 40) and the center of mass R is oriented on a first side $S_1$ of the longitudinal axis L of the collection container 82, to a second position, such as shown in FIG. 29, in which the mechanical separator 40 is disengaged from the closure or initial engagement position with the collection container, and the center of mass R is oriented across the longitudinal axis L of the collection container 82. At some point, during the transition of the center of mass R across the longitudinal axis L of the collection container 82, the float 42 of the mechanical separator 40 must deform in a direction substantially perpendicular to the through-axis T of the separator body 41 in order to allow for transition of the mechanical separator 40 from the initial first position to the second sealing position. During elongation of the float 42, the higher and lower density phases of the specimen may pass between the mechanical separator 40, specifically the elongated float 42, and the sidewall 86 of the collection container 82 in which the mechanical separator is in an intermediate position. From the intermediate position, the mechanical separator may subsequently transition to the sealing position, in which a portion of the float 42 forms a sealing engagement with a portion of the interior of the collection container, upon termination of applied rotational force.

Accordingly, the mechanical separator of the present invention may be considered to transition between three phases of operation: the initial phase in which a specimen is provided through the through-hole of the separator body; the intermediate phase in which the separator has disengaged from the initial position and the float 42 is elongated to allow passage of higher and lower density phases thereby; and the sealing position in which the float 42 forms a barrier with a portion of the collection container. During this sequence of phases, the mechanical separator may be considered as "open-open-closed" wherein an "open" phase is defined as a state in which the mechanical separator does not form a staling barrier with the collection container preventing the passage of fluid therethrough and therearound. In contrast, a "closed" phase is defined as a state in which mechanical separator 40 does form a sealing barrier with the collection container preventing the passage of fluid therethrough and therearound.

The mechanical separator of the present invention is also intended for use with various closure arrangements in the initial phase. Referring to FIG. 40, the mechanical separator 40 may be maintained in the initial position by the interference between the float 42 and the initial engagement band 116 and the sidewall 86 of the collection container 82. In this configuration, the mechanical separator 40 is not restrained by any portion of the closure 84.

In another configuration, as shown in FIGS. 41-44, the separation assembly includes a closure 84 and a post 180 engaged within a recess 181 of the closure 84. The post 180 may include a separator receiving end 182 and a closure engagement end 183. The closure engagement end 183 may be adapted for positioning within the recess 181 of the closure 84 and may optionally include at least one barb 184 for securing the post 180 within the closure 84. The separator receiving end 182 may have any suitable profile such that it may be at least partially disposed within the through-hole 46 of the separator body 41. In one embodiment, the separator receiving end 182 has a substantially circular cross-section. In another embodiment, the separator receiving end 182 has a substantially elliptical cross-section. The separator receiving end 182 is dimensioned to snugly fit within the through-hole 46 to provide a releaseable engagement with the mechanical separator 40. The post 180 is also adapted for positioning within the interior of the collection container 82 and includes a post through-hole 186 aligned along the longitudinal axis of the collection container 82. When the mechanical separator 40 is engaged with the post 180, a fluid path is formed between the through-hole 46 of the mechanical separator 40 and the post through-hole 186 of the post 180. This effectively forms a "sealed" fluid path for the direction of the fluid sample into the collection container 82. Upon application of rotational force, the mechanical separator experiences a slight longitudinal movement prior to the axial rotation as the mechanical separator is pulled downward off the post 180 during applied rotation.

Referring to FIGS. 45-46, an alternative separation assembly is shown including a collection container 782 having a first region 783 having an open top end 784 and a first sidewall 785 defining a first interior 786 and a first exterior 787. The collection container 782 also includes a second region 788 having a closed bottom end 789 and a second sidewall 790 defining a second interior 791 and a second exterior 792. In this configuration, the first region 783 and the second region 788 are aligned along a longitudinal axis $L_A$ such that the first interior 786 and the second interior 791 are provided in fluid communication. The first interior 786 includes a first diameter $D_F$ and the second interior 791 includes a second diameter $D_S$, with the first diameter $D_F$ being greater than the second diameter $D_S$. The collection container 782 also includes at least one fluid flute 793 extending between the first region 783 and the second region 788 to allow passage of fluid therethrough from the first region 783 to the second region 788. In this configuration, the first exterior 787 of the first region 783 may have a profile that corresponds to a 16 mm collection tube, and the second exterior 792 of the second region 788 may have a profile that corresponds to a 13 mm collection tube.

The first interior 786 of the first region 783 may be dimensioned to accommodate a mechanical separator 40 therein in any of the configurations described herein. The second interior 791 is dimensioned to at least partially restrain a portion of the mechanical separator 40 from passing therein in the initial position and absent applied rotational force. During application of rotational force, the float portion 42 of the mechanical separator 40 may elongate thereby decreasing the effective diameter of the mechanical separator 40 and allowing passage of the mechanical separator into the second interior 791. In this configuration, the orientation of the through-hole 46 of the mechanical separator 40 is irrelevant as the introduction of fluid sample into the collection container 782 occurs around the separator body 41 as opposed to through the through-hole 46. Specifically, fluid is introduced into the collection container 782 into the first interior 786 and around the mechanical separator 40. The sample then passes into the second interior 791 by way of the fluid flutes 793. Accordingly, the initial orientation of the mechanical separator 40 is irrelevant to the function of the separator in this embodiment.

In accordance with a further embodiment of the present invention, as shown in FIG. 46A, a mechanical separator, as described herein, may be used with a collection container 782A having a slight taper along a portion of the sidewall 783A extending between an open top end 784A and a closed bottom end 785A. In this configuration, the collection container 782A includes a first region indicator section A of FIG. 46A. First region indicator section A is disposed along a portion of the sidewall 783A at a distance 786A from the open top end 784A. The collection container 782A may also include a second region indicator section B of FIG. 46A. Second region indicator section B is disposed along a portion of the sidewall 783 at a distance 788A from the open top end 784A. In one configuration, the region defined between the first region indicator section A and the second region indicator B may have substantially no taper. In another configuration, the region defined between the first region indicator section A and the second region indicator B may have substantially may have a slight inward taper. In a further embodiment, the region defined between the first region indicator section A and the second region indicator B may be about the expected separation transition between the separated higher and lower density phases of a liquid to be separated.

Figure 47:
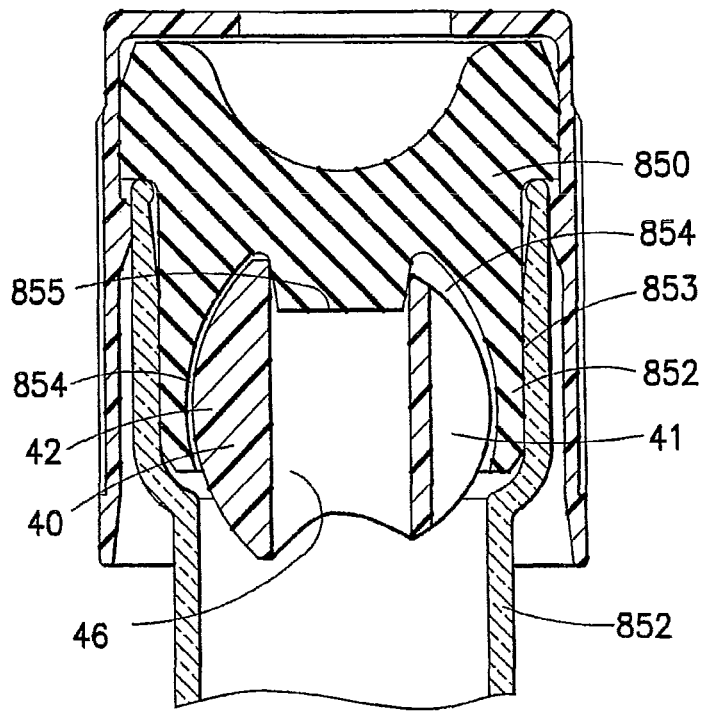
FIG. 47 is a cross-sectional side view of an alternative separation assembly having a mechanical separator engaged within a portion of a closure in accordance with an embodiment of the present invention.
Figure 48:
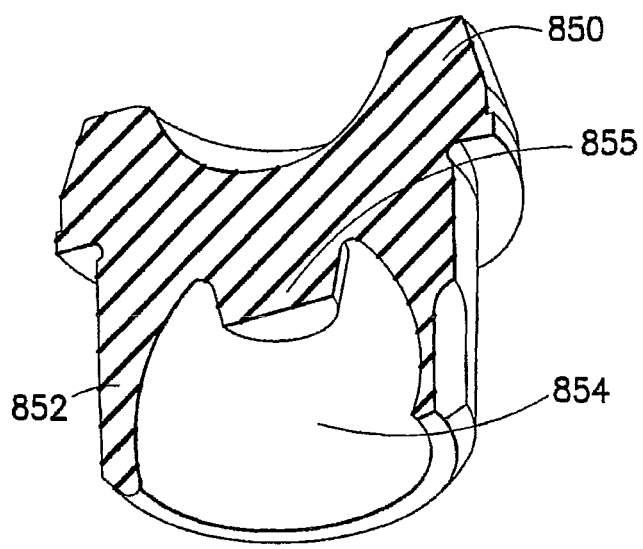
FIG. 48 is a partial cross-sectional perspective of the closure of FIG. 47.

In yet another embodiment, shown in FIGS. 47-48, the separation assembly includes a closure 850 adapted for sealing engagement with the collection container 852. The closure 850 includes a receiving end 842 for positioning within the open end 853 of the collection container 852. The receiving end 842 defines an interior cavity 854 and includes an undercut protrusion 855 extending into the interior cavity 854. The undercut protrusion 855 of the closure 850 is at least partially disposed within the through-hole 46 of the mechanical separator 40 in the initial position. Also in the initial position, at least a portion of the separator body 41 is disposed within the interior cavity 854. The positioning of the mechanical separator 40 within the interior cavity 854 ensures that the mechanical separator 40 remains captured in the closure 850 during assembly of the closure 850 with the collection container 852. This configuration may be utilized with the collection container having a first region and a second region, as described above. During application of rotational force, the float 42 of the mechanical separator 40 elongates allowing the mechanical separator 40 to disengage from the closure 850.

Figure 49:
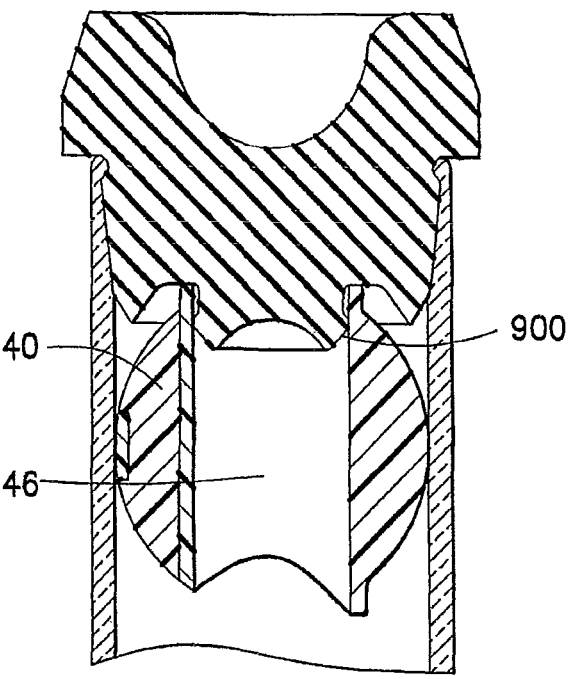
FIG. 49 is a cross-sectional side view of a separation assembly having a mechanical separator engaged with a closure having an engagement boss in accordance with an embodiment of the present invention.
Figure 50:
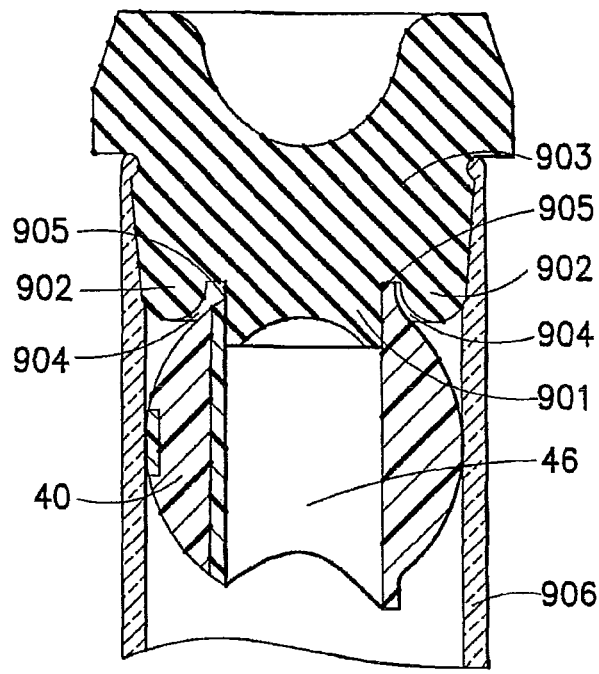
FIG. 50 is a cross-sectional side view of an alternative separation assembly having a mechanical separator engaged with a closure having an alternative engagement boss in accordance with an embodiment of the present invention.

Referring now to FIGS. 49-59, various other engagements between the mechanical separator 40 and the closure 84 are also contemplated herein. As shown in FIG. 49, the mechanical separator 40 may include an angled engagement boss 900 disposed within the through-hole 46 in the initial position. As shown in FIG. 50, the mechanical separator 40 may include a substantially cylindrical engagement boss 901 disposed within the through-hole 46 in the initial position. A flanking portion 902 of the closure 903 may be provided adjacent an exterior surface 904 of the mechanical separator 40 adjacent the first opening 905 for further securing the mechanical separator 40 with the closure 903 and establishing a "sealed" fluid path into the collection container 906 therethrough.

Figure 51:
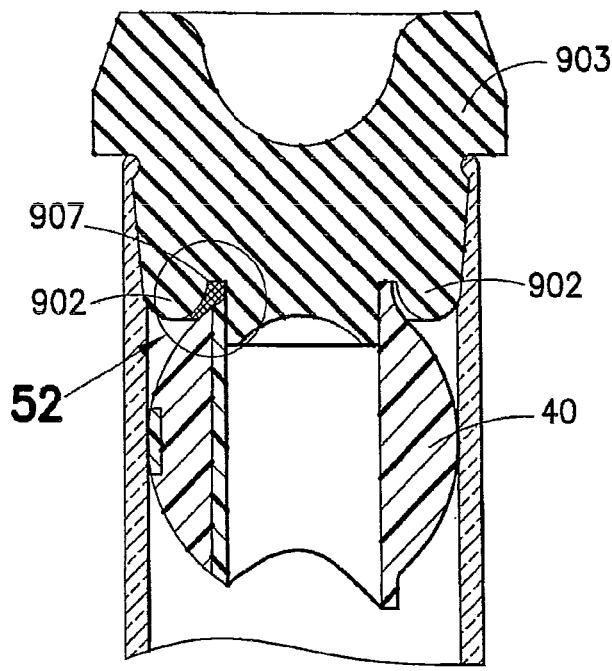
FIG. 51 is a cross-sectional side view of the separation assembly of FIG. 50 having a sealant disposed between a portion of the mechanical separator and a portion of the closure in accordance with an embodiment of the present invention.
Figure 52:
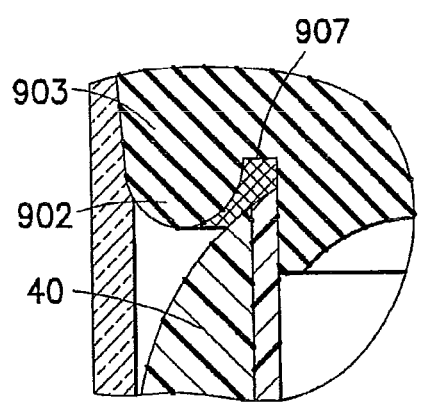
FIG. 52 is a close-up sectional view of the sealant shown in FIG. 51.

Referring to FIGS. 51-52, a sealant 907 may be provided adjacent the flanking portion 902, as described above, for further securing the mechanical separator 40 and the closure 903. The sealant 907 may be sufficiently tacky to retain the mechanical separator 40 in place in the initial position, yet weak enough to permit release of the mechanical separator 40 from the closure 903 upon application of rotational force.

Figure 53:
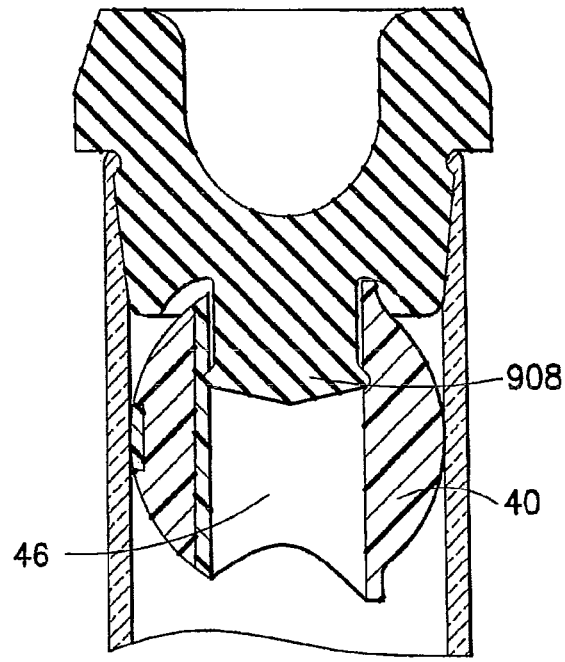
FIG. 53 is a cross-sectional side view of an alternative separation assembly having a mechanical separator engaged with a closure having an alternative engagement boss in accordance with an embodiment of the present invention.
Figure 54:
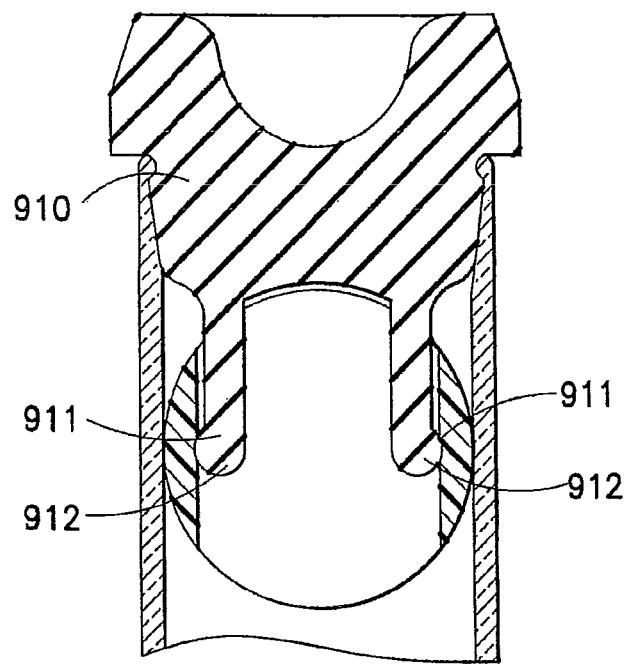
FIG. 54 is a cross-sectional side view of an alternative separation assembly having a mechanical separator engaged with a closure having an alternative engagement boss in accordance with an embodiment of the present invention.
Figure 55:
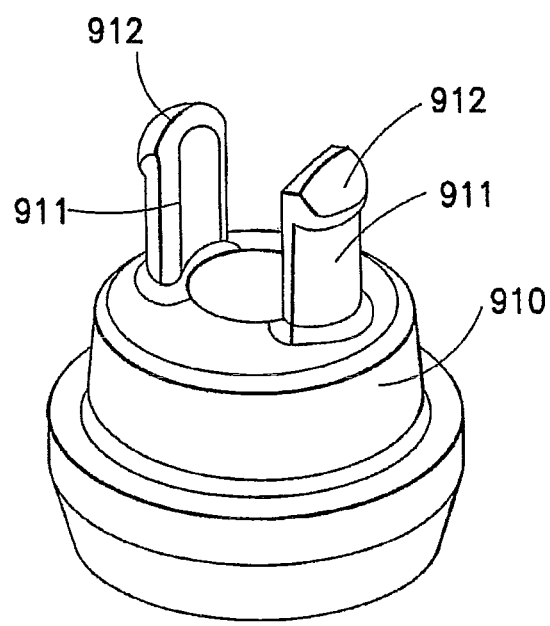
FIG. 55 is a perspective view of the closure of FIG. 54 having an engagement boss including a plurality of depending feet.

Referring to FIG. 53, yet another alternative angled engagement boss 908 may be disposed within the through-hole 46 in the initial position. Referring to FIGS. 54-55, the closure 910 may include at least one, such as two, depending arms 911 for engagement with the mechanical separator 40. In one configuration, each depending arm 911 includes a contact protrusion 912 for engaging a portion of the mechanical separator 40 within the through-hole 46 in the initial position. The interference between the contact protrusion 912 and the mechanical separator 40 may be sufficient to restrain the mechanical separator 40 with the closure 910 in the initial position, yet allow for disengagement of the mechanical separator 40 from the closure 910 upon application of rotational force.

Figure 56:
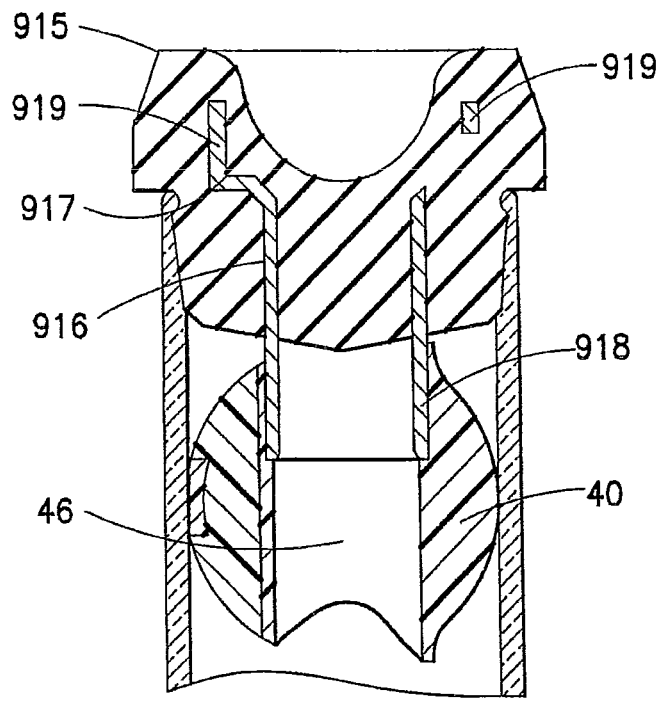
FIG. 56 is a cross-sectional side view of an alternative separation assembly having a mechanical separator engaged with a molding insert in accordance with an embodiment of the present invention.
Figure 57:
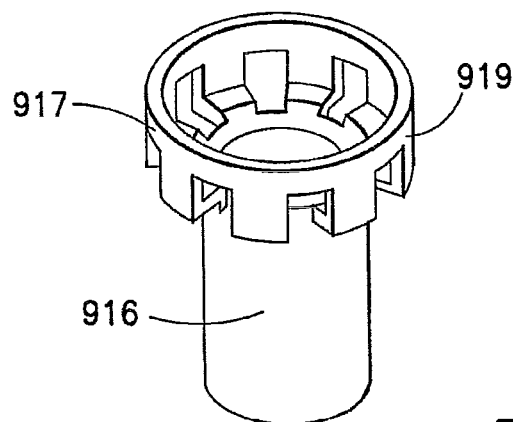
FIG. 57 is a perspective view of the molding insert of FIG. 56.
Figure 58:
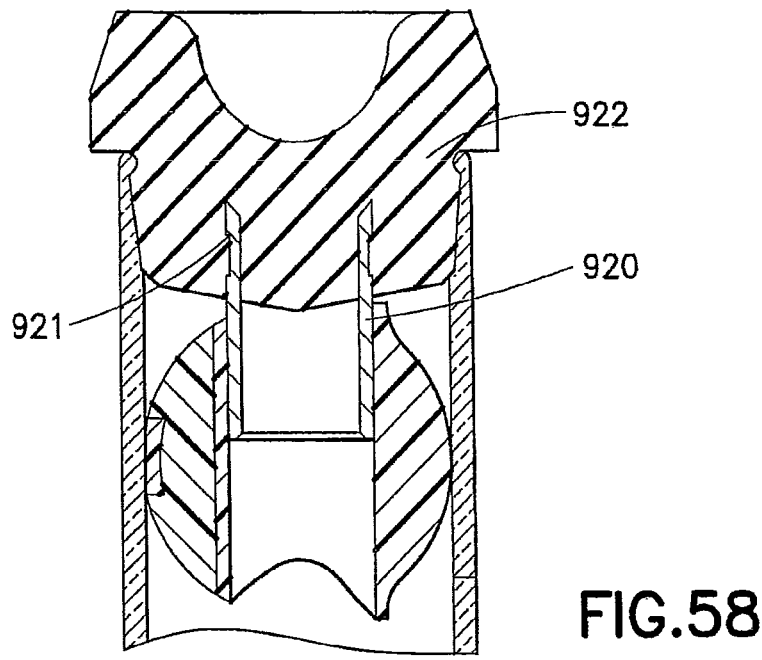
FIG. 58 is a cross-sectional side view of an alternative separation assembly having a mechanical separator engaged with a molding insert in accordance with an embodiment of the present invention.
Figure 59:
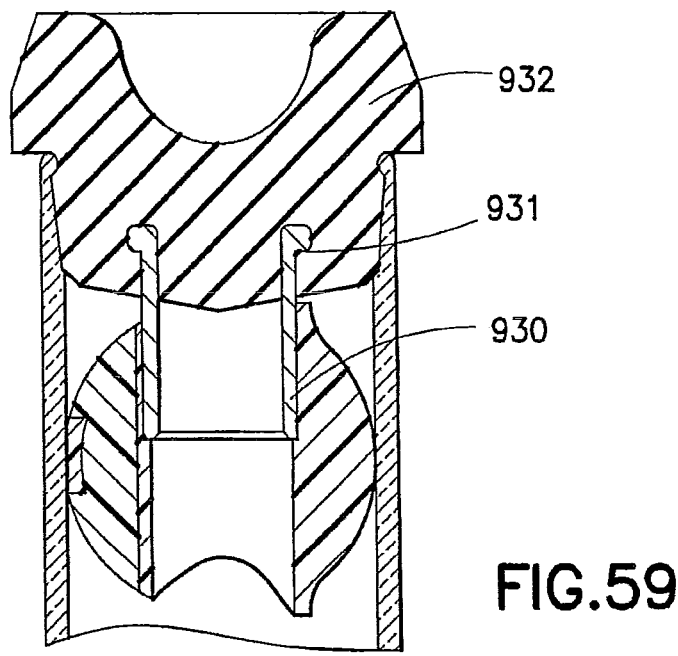
FIG. 59 is a cross-sectional side view of an alternative separation assembly having a mechanical separator engaged with a molding insert in accordance with an embodiment of the present invention.
Figure 63:
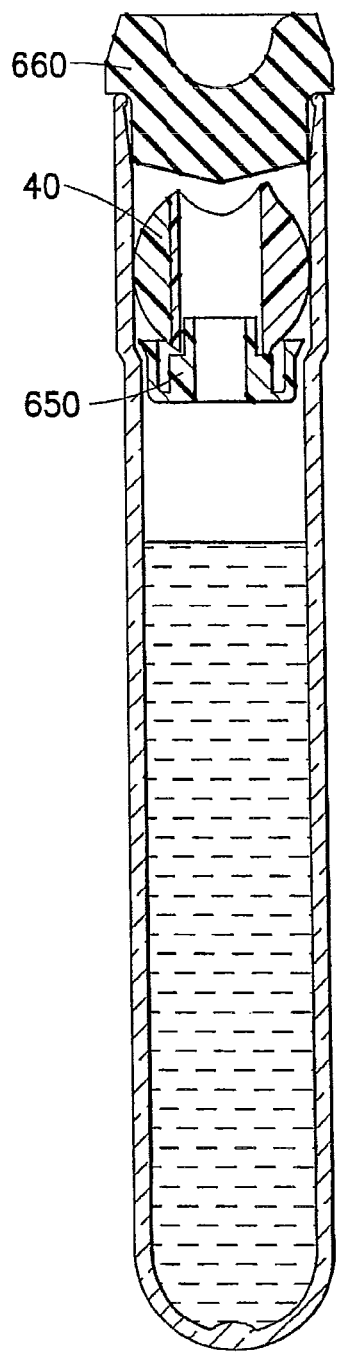
FIG. 63 is a cross-sectional side view of a separation assembly having a mechanical separator engaged with a carrier in an initial position in accordance with an embodiment of the present invention.
Figure 64:
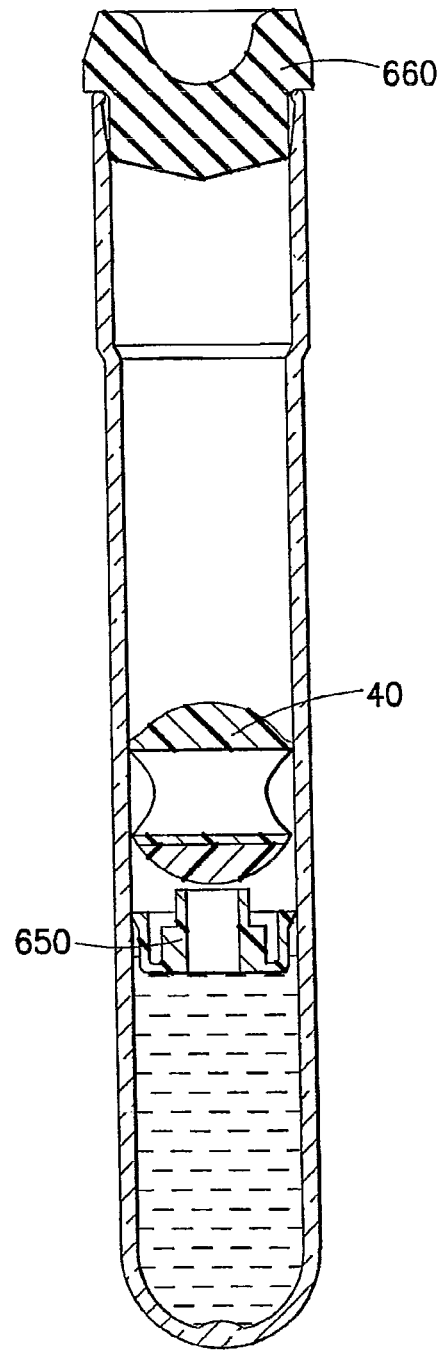
FIG. 64 is a cross-sectional side view of the separation assembly of FIG. 63 having a mechanical separator in a sealing position disengaged from the carrier after application of rotational force in accordance with an embodiment of the present invention.
Figure 65:
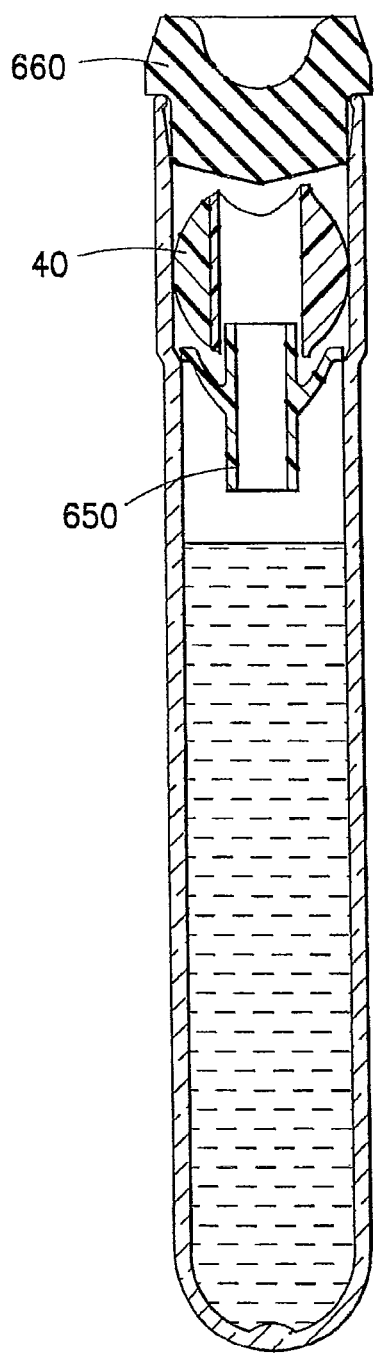
FIG. 65 is a cross-sectional side view of an alternative separation assembly having a mechanical separator engaged with an alternative carrier in an initial position in accordance with an embodiment of the present invention.
Figure 66:
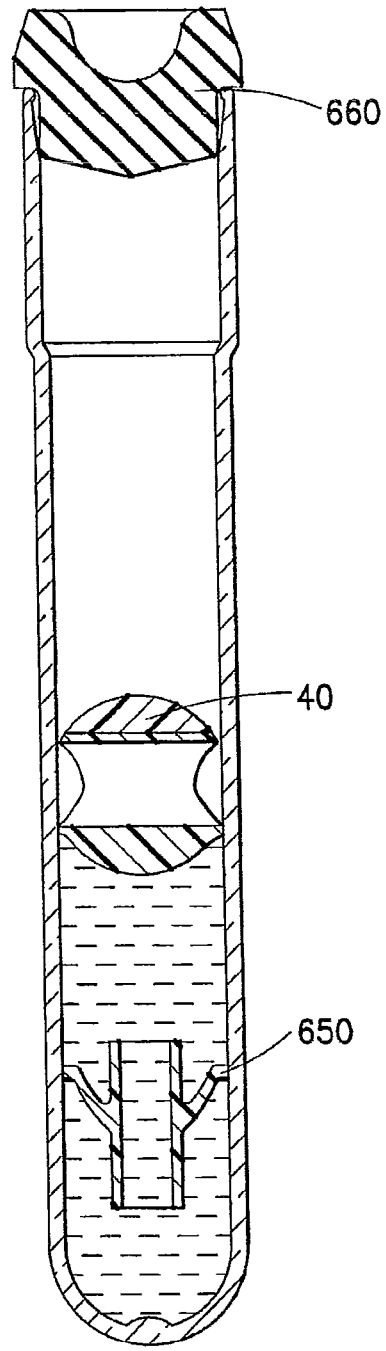
FIG. 66 is a cross-sectional side view of the separation assembly of FIG. 65 having a mechanical separator in a sealing position disengaged from the carrier after application of rotational force in accordance with an embodiment of the present invention.

Referring to FIGS. 56-57, the closure 915 may include a molding insert 916 having a wedging basket 917 for further securing the molding insert 916 with the closure 915. As described above, the molding insert 916 may include a separator receiving end 918 for engaging the mechanical separator 40 through the through-hole 46, and a closure engagement end 919, as described above. Referring to FIG. 58, another molding insert 920 may include at least one barb 921 for further securing the molding insert 920 with the closure 922. Referring to FIG. 59, yet another molding insert 930 may include at least one protrusion 931 for securing the molding insert 930 with the closure 932.

Referring to FIGS. 60-68, the separation assemblies described herein may also include a carrier 650 releasably engaged with a portion of the mechanical separator 40 in the initial position. In each of these configurations, the carrier 650 disengages from the mechanical separator 40 upon application of rotational force and enters the fluid phase disposed below the mechanical separator 40 for the purpose of preventing clots or fibrin strands from interfering with the operation of the mechanical separator 40.

As shown in FIG. 60, the carrier 650 may include a closure engagement portion 651 for releasable engagement with a portion of the closure 652, and a depending portion 653 for releasable engagement with a portion of the mechanical separator 40, such as through the through-hole 46. As shown in FIG. 61, the carrier 650 may include a closure engagement portion 651 having a plurality of flanges 654. The carrier 650 may also include a bowed separator engagement portion 655 for engaging a portion of the mechanical separator 40, such as within the through-hole 46. Upon application of rotational force, the mechanical separator 40 disengages from the initial position and rotates as described herein. Upon rotation of the mechanical separator 40, the bowed separator engagement portion 655 contracts and allows the mechanical separator 40 to separate from the carrier 650.

Figure 67:
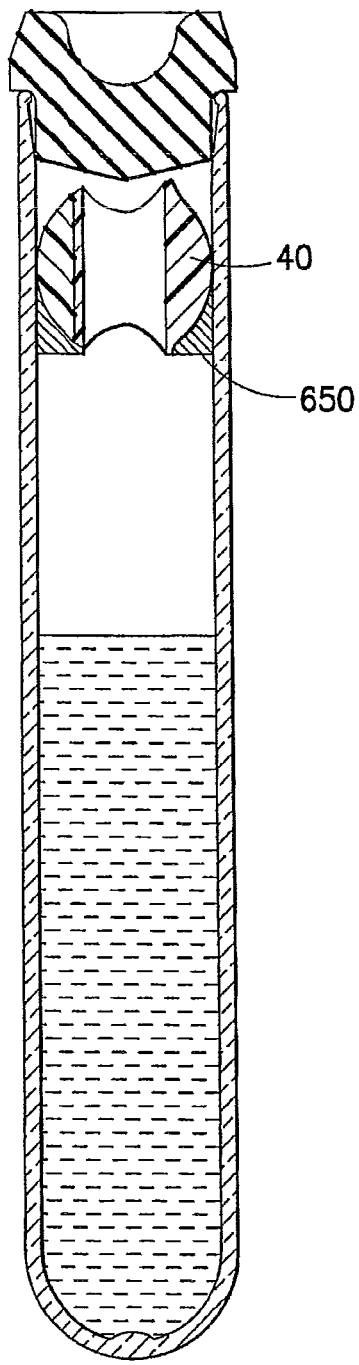
FIG. 67 is a cross-sectional side view of an alternative separation assembly having a mechanical separator engaged with a dissolvable carrier in an initial position in accordance with an embodiment of the present invention.

Referring to FIGS. 63-66, the carrier 650 may also be releasably connected to the mechanical separator 40 in a direction opposed from the closure 660. Referring to FIGS. 67-68, the carrier 650 may optionally consist of a dissolvable material which diffuses into the sample when contact is made, as shown in FIG. 68.

One of the significant benefits of the mechanical separator of the present invention is that it does not require penetration by a needle cannula in order to permit entry of a fluid sample into a collection container. In each of the above-described embodiments, when the assembly is subjected to an applied rotational force, such as centrifugation, the respective phases of the specimen, such as blood, will begin to separate into a denser phase displaced toward the bottom of the collection container, and a less dense phase displaced toward the top of the collection container. The applied rotational force will urge the ballast of the mechanical separator toward the closed bottom end and the float toward the top end of the collection container. This movement of the ballast will generate a longitudinal deformation of the float. As a result, the float will become longer and narrower and will be spaced concentrically inward from the inner surface of the cylindrical sidewall of the collection container. Accordingly, lighter phase components of the blood will be able to slide past the float and travel upwards, and likewise, heavier phase components of the blood will be able to slide past the float and travel downwards.

As noted above, the mechanical separator of the present invention typically has an overall density between the densities of the separated phases of the blood. Consequently, the mechanical separator will stabilize in a position within the collection container such that the heavier phase components will be located between the mechanical separator and the closed bottom end of the collection container, while the lighter phase components will be located between the mechanical separator and the top end of the collection container.

After this stabilized state has been reached, the centrifuge will be stopped and the float will resiliently return to its unbiased state and into sealing engagement with the interior of the cylindrical sidewall of the collection container. The formed liquid phases may then be accessed separately for analysis. In one embodiment, the assembled mechanical separator of the present invention may be scaled to fit within a 13 mm collection tube.

In use, the mechanical separator of the present invention minimizes device pre-launch and eliminates the need for cannula puncture which substantially eliminates sample pooling under the closure. Additionally, the reduced clearance of the mechanical separator minimizes the loss of trapped fluid phases, such as serum and plasma.

While the present invention is described with reference to several distinct embodiments of a mechanical separator assembly and method of use, those skilled in the art may make modifications and alterations without departing from the scope and spirit. Accordingly, the above detailed description is intended to be illustrative rather than restrictive.

The invention claimed is:

1. A mechanical separator for separating a liquid sample into first and second phases within a collection container, comprising:
   a separator body having a through-hole defined therein, the through-hole defining a through-axis and adapted for allowing liquid to pass therethrough, the separator body comprising:
   a float, having a first density; and
   a ballast, having a second density different than the first density, wherein a portion of the float is connected to a portion of the ballast,
   wherein the float defines an upper exterior surface of the separator, the ballast defines a lower exterior surface of the separator, and the through-axis is disposed within a plane angled with respect to a plane extending vertically from an apex of the upper exterior surface of the float to an apex of the lower exterior surface of the ballast and bisecting the separator into a first half and a second half, the first half including a first opening of the through-hole and the second half including a second opening of the through-hole, and
   wherein the apex of the float and the apex of the ballast are aligned along a central longitudinal axis of the separator.

2. The mechanical separator of claim 1, wherein at least a portion of the mechanical separator has a spheroid shape.

3. The mechanical separator of claim 2, wherein the float comprises an exterior surface and a joining surface, and the ballast comprises a contact surface connected to the joining surface of the float and an exterior surface, wherein the exterior surface of the float and the exterior surface of the ballast taken together form the spheroid shape.

4. The mechanical separator of claim 1, wherein the float defines the through-hole adapted for allowing liquid to pass therethrough.

5. The mechanical separator of claim 1, wherein the through-hole has a circular cross-section.

6. The mechanical separator of claim 1, wherein the through-hole has an elliptical cross-section.

7. The mechanical separator of claim 1, wherein the through-hole is defined along a through-axis and the float is adapted for deformation in a direction perpendicular to the through-axis upon applied rotational force.

8. The mechanical separator of claim 1, wherein the float further comprises a first extended tab adjacent a first opening of the through-hole and a second extended tab adjacent the second opening of the through-hole.

9. The mechanical separator of claim 8, wherein the first extended tab and the second extended tab are provided at least partially above and about the through-hole and extend radially outwardly from a portion of the float in a direction parallel to the through-axis of the separator body.

10. The mechanical separator of claim 8, wherein the first extended tab, an upper surface of the float, and the second extended tab form an at least partially convex upper float surface.

11. The mechanical separator of claim 1, wherein the separator body further comprises an extended tab band disposed about a portion of an outer surface of the float.

12. The mechanical separator of claim 11, wherein a first portion of the extended tab band is disposed adjacent a first opening of the through-hole and a second portion of the extended tab band is disposed adjacent a second opening of the through-hole.

13. The mechanical separator of claim 12, wherein at least one of the first portion and the second portion of the extended tab band have a concave downwardly-directed orientation.

14. The mechanical separator of claim 12, wherein at least one of the first portion and the second portion of the extended tab band are oriented in an outwardly-extending arcuate shape about an upper portion of at least one of the first opening and second opening of the through-hole.

15. The mechanical separator of claim 14, wherein at least one of the first portion and the second portion of the extended tab band extend radially outwardly from the float.

16. The mechanical separator of claim 12, wherein at least a portion of the first extended portion and at least a portion of the second extended portion of the extended tab band have the same shape and curvature.

17. The mechanical separator of claim 12, wherein the extended tab band further comprises a joining portion disposed between and connecting the first extended portion and the second extended portion disposed on each connecting side of the separator body.

18. The mechanical separator of claim 17, wherein the first extended portion and the second extended portion of the extended tab band have a concave downwardly-directed orientation, and the joining portions of the extended tab band have a concave upwardly-directed orientation.

19. The mechanical separator of claim 11, wherein the float comprises the extended tab band.

20. The mechanical separator of claim 11, wherein the float and the extended tab band are formed of TPE and the ballast is formed of PET.

21. The mechanical separator of claim 1, further comprising an initial engagement band circumferentially disposed about at least a portion of the separator body.

22. The mechanical separator of claim 21, wherein the initial engagement band is at least one of continuous and at least partially segmented.

23. The mechanical separator of claim 21, wherein the initial engagement band and the float are formed of the same material.

24. The mechanical separator of claim 21, wherein the initial engagement band bisects at least a portion of the ballast.

25. The mechanical separator of claim 1, wherein the ballast comprises a base portion and a joining structure for engaging a portion of the float.

26. The mechanical separator of claim 25, wherein the joining structure comprises a plurality of arms for engaging a portion of the float.

27. The mechanical separator of claim 25, wherein the joining structure provides flexure between the float and the ballast.

28. The mechanical separator of claim 25, wherein at least a portion of the float has a circular outer perimeter, and at least a portion of the float has a curved cross-section perpendicular to the through-hole.

29. The mechanical separator of claim 28, wherein the joining structure comprises a plurality of arms for engaging a portion of the ballast.

30. The mechanical separator of claim 28, wherein the joining structure provides flexure between the float and the ballast.

31. The mechanical separator of claim 1, wherein the float comprises a joining structure for engaging a portion of the ballast.

32. The mechanical separator of claim 1, wherein the through-axis is disposed within a plane that is perpendicular to a plane extending vertically from the apex of the upper exterior surface of the float to the apex of the lower exterior surface of the ballast and bisecting the separator into the first half and the second half.

33. The mechanical separator of claim 1, wherein the central longitudinal axis of the separator extends perpendicular to the through-axis.

* * * * *